US009526723B2

(12) United States Patent
Moss et al.

(10) Patent No.: US 9,526,723 B2
(45) Date of Patent: Dec. 27, 2016

(54) TREATMENT WITH OPIOID ANTAGONISTS AND MTOR INHIBITORS

(71) Applicant: THE UNIVERSITY OF CHICAGO, Chicago, IL (US)

(72) Inventors: Jonathan Moss, Chicago, IL (US); Patrick A. Singleton, Chicago, IL (US)

(73) Assignee: THE UNIVERSITY OF CHICAGO, Chicago, IL (US)

(*) Notice: Subject to any disclaimer, the term of this patent is extended or adjusted under 35 U.S.C. 154(b) by 0 days.

(21) Appl. No.: 14/179,095

(22) Filed: Feb. 12, 2014

(65) Prior Publication Data

US 2014/0163059 A1 Jun. 12, 2014

Related U.S. Application Data

(63) Continuation of application No. 12/933,784, filed as application No. PCT/US2009/037825 on Mar. 20, 2009, now Pat. No. 8,685,995.

(60) Provisional application No. 61/038,577, filed on Mar. 21, 2008.

(51) Int. Cl.
| | |
|---|---|
| *A61K 31/165* | (2006.01) |
| *A61K 31/436* | (2006.01) |
| *A61K 31/451* | (2006.01) |
| *A61K 31/485* | (2006.01) |
| *A61K 45/06* | (2006.01) |

(52) U.S. Cl.
CPC .......... *A61K 31/485* (2013.01); *A61K 31/165* (2013.01); *A61K 31/436* (2013.01); *A61K 31/451* (2013.01); *A61K 45/06* (2013.01)

(58) Field of Classification Search
CPC .. A61K 31/165; A61K 31/436; A61K 31/451; A61K 31/585; A61K 45/06
See application file for complete search history.

(56) References Cited

U.S. PATENT DOCUMENTS

| | | |
|---|---|---|
| 3,723,440 A | 3/1973 | Freter et al. |
| 3,854,480 A | 12/1974 | Zaffaroni |
| 3,937,801 A | 2/1976 | Lippmann |
| 4,115,400 A | 9/1978 | Zimmerman |
| 4,176,186 A | 11/1979 | Goldberg et al. |
| 4,311,833 A | 1/1982 | Namikoshi et al. |
| 4,316,885 A | 2/1982 | Rakhit |
| 4,322,426 A | 3/1982 | Hermann et al. |
| 4,377,568 A | 3/1983 | Chopra et al. |
| 4,385,078 A | 5/1983 | Onda et al. |
| 4,427,676 A | 1/1984 | White et al. |
| 4,452,775 A | 6/1984 | Kent |
| 4,457,907 A | 7/1984 | Porter et al. |
| 4,462,839 A | 7/1984 | McGinley et al. |
| 4,518,433 A | 5/1985 | McGinley et al. |
| 4,556,552 A | 12/1985 | Porter et al. |
| 4,581,456 A | 4/1986 | Barnett |
| 4,606,909 A | 8/1986 | Bechgaard et al. |
| 4,615,885 A | 10/1986 | Nakagame et al. |
| 4,650,803 A | 3/1987 | Stella et al. |
| 4,670,287 A | 6/1987 | Tsuji et al. |
| 4,675,189 A | 6/1987 | Kent et al. |
| 4,689,332 A | 8/1987 | McLaughlin et al. |
| 4,719,215 A | 1/1988 | Goldberg |
| 4,730,048 A | 3/1988 | Portoghese |
| 4,806,556 A | 2/1989 | Portoghese |
| 4,836,212 A | 6/1989 | Schmitt et al. |
| 4,857,533 A | 8/1989 | Sherman et al. |
| 4,861,781 A | 8/1989 | Goldberg |
| 4,863,928 A | 9/1989 | Atkinson et al. |
| 4,888,346 A | 12/1989 | Bihari et al. |
| 4,891,379 A | 1/1990 | Zimmerman et al. |
| 4,912,114 A | 3/1990 | Revesz |
| 4,965,269 A | 10/1990 | Brandstrom et al. |
| 4,987,136 A | 1/1991 | Kreek et al. |
| 5,023,263 A | 6/1991 | Von Burg |
| 5,023,264 A | 6/1991 | Caufield et al. |
| 5,100,883 A | 3/1992 | Schiehser |
| 5,102,887 A | 4/1992 | Goldberg |
| 5,118,677 A | 6/1992 | Caufield |
| 5,118,678 A | 6/1992 | Kao et al. |
| 5,120,842 A | 6/1992 | Failli et al. |
| 5,133,974 A | 7/1992 | Paradissis et al. |
| 5,159,081 A | 10/1992 | Cantrell et al. |
| 5,162,333 A | 11/1992 | Failli et al. |
| 5,177,203 A | 1/1993 | Failli et al. |
| 5,202,159 A | 4/1993 | Chen et al. |
| 5,221,670 A | 6/1993 | Caufield |
| 5,233,036 A | 8/1993 | Hughes |

(Continued)

FOREIGN PATENT DOCUMENTS

| | | |
|---|---|---|
| CA | 2064373 | 9/1992 |
| CA | 1315689 | 4/1993 |

(Continued)

OTHER PUBLICATIONS

Yuan, The Annals of Pharmacotherapy, Jun. 2007, Sage Publications, vol. 41, pp. 984-993.*
Aballay, A. et al., "Caenorhabditis elegans as a host for the study of host-pathogen interactions," Curr. Opin. Microbiol. (2002) 5:97-101.
Aepfelbacher, M. et al., "Bacterial toxins block endothelial wound repair. Evidence that Rho GTPases control cytoskeletal rearrangements in migrating endothelial cells," Arterioscler. Thromb. Vasc. Biol. (1997) 17(9):1623-1629.
Akinbami, M.A. et al., Effect of a peripheral and a central acting opioid antagonist on the testicular response to stress in rats. Neuroendocrinology. Apr. 1994;59(4):343-8.
Aliaga, L. et al., "A clinical index predicting mortality with Pseudomonas aeruginosa bacteraemia," J. Med. Microbiol. (2002) 51:615-619.

(Continued)

*Primary Examiner* — Sarah Pihonak
(74) *Attorney, Agent, or Firm* — Michael Best & Friedrich LLP

(57) ABSTRACT

Embodiments of the invention provide methods of treating a disorder or disease characterized by cellular proliferation and migration by co-administering a synergistically effective amount of an mTOR inhibitor and a μ-opioid receptor antagonist.

5 Claims, 12 Drawing Sheets

(56) References Cited

U.S. PATENT DOCUMENTS

| | | |
|---|---|---|
| 5,250,542 A | 10/1993 | Cantrell et al. |
| 5,256,790 A | 10/1993 | Nelson |
| 5,258,389 A | 11/1993 | Goulet et al. |
| 5,260,300 A | 11/1993 | Hu |
| 5,262,423 A | 11/1993 | Kao |
| 5,270,328 A | 12/1993 | Cantrell et al. |
| 5,302,584 A | 4/1994 | Kao et al. |
| 5,362,718 A | 11/1994 | Skotnicki et al. |
| 5,373,014 A | 12/1994 | Failli et al. |
| 5,378,836 A | 1/1995 | Kao et al. |
| 5,385,908 A | 1/1995 | Nelson et al. |
| 5,385,909 A | 1/1995 | Nelson et al. |
| 5,385,910 A | 1/1995 | Ocain et al. |
| 5,389,639 A | 2/1995 | Failli et al. |
| 5,391,372 A | 2/1995 | Campbell |
| 5,391,730 A | 2/1995 | Skotnicki et al. |
| 5,407,686 A | 4/1995 | Patel et al. |
| 5,411,967 A | 5/1995 | Kao et al. |
| 5,426,112 A | 6/1995 | Zagon et al. |
| 5,434,171 A | 7/1995 | Frank et al. |
| 5,434,260 A | 7/1995 | Skotnicki et al. |
| 5,463,048 A | 10/1995 | Skotnicki et al. |
| 5,472,943 A | 12/1995 | Crain et al. |
| 5,480,988 A | 1/1996 | Failli et al. |
| 5,480,989 A | 1/1996 | Kao et al. |
| 5,489,680 A | 2/1996 | Failli et al. |
| 5,491,231 A | 2/1996 | Nelson et al. |
| 5,504,091 A | 4/1996 | Molnar-Kimber et al. |
| 5,512,578 A | 4/1996 | Crain et al. |
| 5,536,507 A | 7/1996 | Abramowitz et al. |
| 5,563,145 A | 10/1996 | Failli et al. |
| 5,567,423 A | 10/1996 | Ying et al. |
| 5,591,433 A | 1/1997 | Michael et al. |
| 5,597,564 A | 1/1997 | Ying et al. |
| 5,609,871 A | 3/1997 | Michael et al. |
| 5,614,219 A | 3/1997 | Wunderlich et al. |
| 5,614,222 A | 3/1997 | Kaplan et al. |
| 5,626,875 A | 5/1997 | Ballester Rodes et al. |
| 5,629,001 A | 5/1997 | Michael et al. |
| 5,656,290 A | 8/1997 | Kelm et al. |
| 5,665,772 A | 9/1997 | Cottens et al. |
| 5,736,152 A | 4/1998 | Dunn |
| 5,767,125 A | 6/1998 | Crain et al. |
| 5,780,462 A | 7/1998 | Lee et al. |
| 5,804,595 A | 9/1998 | Portoghese et al. |
| 5,811,451 A | 9/1998 | Minoia et al. |
| 5,821,219 A | 10/1998 | Grandy et al. |
| 5,866,154 A | 2/1999 | Bahal et al. |
| 5,866,164 A | 2/1999 | Kuczynski et al. |
| 5,958,452 A | 9/1999 | Oshlack et al. |
| 5,972,954 A | 10/1999 | Foss et al. |
| 5,981,185 A | 11/1999 | Matson et al. |
| RE36,547 E | 2/2000 | Crain et al. |
| 6,025,154 A | 2/2000 | Li et al. |
| 6,096,756 A | 8/2000 | Crain et al. |
| 6,096,763 A | 8/2000 | Hoffman et al. |
| 6,096,764 A | 8/2000 | Bryant et al. |
| 6,136,780 A | 10/2000 | Zagon et al. |
| 6,153,620 A | 11/2000 | Kornetsky |
| 6,194,382 B1 | 2/2001 | Crain et al. |
| 6,261,599 B1 | 7/2001 | Oshlack et al. |
| 6,274,591 B1 | 8/2001 | Foss et al. |
| 6,277,384 B1 | 8/2001 | Kaiko et al. |
| 6,353,004 B1 | 3/2002 | Farrar et al. |
| 6,359,111 B1 | 3/2002 | Meyer et al. |
| 6,384,044 B1 | 5/2002 | Bihari |
| 6,395,705 B2 | 5/2002 | Crain et al. |
| 6,419,959 B1 | 7/2002 | Walter et al. |
| 6,426,094 B1 | 7/2002 | Piver et al. |
| 6,451,806 B2 | 9/2002 | Farrar |
| 6,455,537 B1 | 9/2002 | Cooper |
| 6,469,030 B2 | 10/2002 | Farrar et al. |
| 6,479,500 B1 | 11/2002 | Fukushima et al. |
| 6,559,158 B1 | 5/2003 | Foss et al. |
| 6,608,075 B2 | 8/2003 | Foss et al. |
| 6,693,125 B2 | 2/2004 | Borisy et al. |
| 6,696,066 B2 | 2/2004 | Kaiko et al. |
| 6,720,336 B2 | 4/2004 | Liras |
| 6,723,712 B2 | 4/2004 | Bourhis et al. |
| 6,756,364 B2 | 6/2004 | Barbier et al. |
| 6,777,534 B1 | 8/2004 | Klagsbrun et al. |
| 6,794,370 B2 | 9/2004 | Achterrath |
| 6,800,639 B2 | 10/2004 | Giles et al. |
| 6,833,349 B2 | 12/2004 | Xia et al. |
| 6,838,469 B2 | 1/2005 | Sumegi |
| 6,884,879 B1 | 4/2005 | Baca et al. |
| 6,900,234 B1 | 5/2005 | Fossa |
| 6,946,556 B1 | 9/2005 | Likhotvorik et al. |
| 6,960,596 B2 | 11/2005 | Bissery |
| 6,967,016 B2 | 11/2005 | van Gemen et al. |
| 6,984,403 B2 | 1/2006 | Hagen et al. |
| 6,989,383 B1 | 1/2006 | Rosen et al. |
| 6,992,106 B2 | 1/2006 | Morinaga et al. |
| 7,012,100 B1 | 3/2006 | Edwards et al. |
| 7,074,825 B2 | 7/2006 | Mo et al. |
| 7,094,775 B2 | 8/2006 | Strugnell et al. |
| 7,129,265 B2 | 10/2006 | Mason |
| 7,132,554 B2 | 11/2006 | Rose |
| 7,141,554 B2 | 11/2006 | Rochat et al. |
| 7,160,913 B2 | 1/2007 | Schneider |
| 7,183,269 B2 | 2/2007 | Kreutz |
| 7,196,115 B2 | 3/2007 | Khanuja et al. |
| 7,259,233 B2 | 8/2007 | Dodd et al. |
| 7,501,434 B2 | 3/2009 | Shah |
| 7,662,365 B2 | 2/2010 | Bentley et al. |
| 8,685,995 B2 | 4/2014 | Moss et al. |
| 2001/0010919 A1 | 8/2001 | Grandy et al. |
| 2001/0018413 A1 | 8/2001 | Crain et al. |
| 2001/0033865 A1 | 10/2001 | Oshlack et al. |
| 2001/0036469 A1 | 11/2001 | Gooberman |
| 2001/0036476 A1 | 11/2001 | Oshlack |
| 2001/0036951 A1 | 11/2001 | Farrar et al. |
| 2001/0046968 A1 | 11/2001 | Zagon et al. |
| 2001/0047005 A1 | 11/2001 | Farrar |
| 2002/0028825 A1 | 3/2002 | Foss et al. |
| 2002/0064771 A1 | 5/2002 | Zhong et al. |
| 2002/0068712 A1 | 6/2002 | Stevens |
| 2002/0173466 A1 | 11/2002 | Crain et al. |
| 2002/0188005 A1 | 12/2002 | Farrar et al. |
| 2003/0022909 A1 | 1/2003 | Moss et al. |
| 2003/0026801 A1 | 2/2003 | Weiner et al. |
| 2003/0039689 A1 | 2/2003 | Chen et al. |
| 2003/0065003 A1 | 4/2003 | Foss et al. |
| 2003/0124086 A1 | 7/2003 | Bentley et al. |
| 2003/0144312 A1 | 7/2003 | Schoenhard |
| 2003/0158220 A1 | 8/2003 | Foss et al. |
| 2003/0191147 A1 | 10/2003 | Sherman et al. |
| 2003/0219406 A1 | 11/2003 | Schroit et al. |
| 2004/0024006 A1 | 2/2004 | Simon |
| 2004/0162306 A1 | 8/2004 | Foss et al. |
| 2004/0162308 A1 | 8/2004 | Foss et al. |
| 2004/0167148 A1 | 8/2004 | Foss et al. |
| 2004/0242523 A1 | 12/2004 | Weichselbaum et al. |
| 2004/0254156 A1 | 12/2004 | Le Bourdonnec et al. |
| 2004/0254208 A1 | 12/2004 | Weber et al. |
| 2004/0259898 A1 | 12/2004 | Moss |
| 2004/0259899 A1 | 12/2004 | Sanghvi et al. |
| 2004/0266806 A1 | 12/2004 | Sanghvi et al. |
| 2005/0004029 A1 | 1/2005 | Garcia |
| 2005/0004155 A1 | 1/2005 | Boyd et al. |
| 2005/0011468 A1 | 1/2005 | Moss |
| 2005/0048117 A1 | 3/2005 | Foss et al. |
| 2005/0085514 A1 | 4/2005 | Cosford et al. |
| 2005/0124885 A1 | 6/2005 | Abend et al. |
| 2005/0187255 A1 | 8/2005 | Lee et al. |
| 2006/0115424 A1 | 6/2006 | Gray |
| 2006/0128742 A1 | 6/2006 | Edwards et al. |
| 2006/0154952 A1* | 7/2006 | Moore ............... A61K 31/436 514/291 |
| 2006/0204512 A1 | 9/2006 | Krasnoperov et al. |
| 2006/0205753 A1 | 9/2006 | Israel |
| 2006/0258696 A1 | 11/2006 | Moss et al. |
| 2007/0020261 A1 | 1/2007 | Sliwkowski et al. |
| 2007/0037887 A1 | 2/2007 | Santen et al. |

(56) References Cited

U.S. PATENT DOCUMENTS

| | | | |
|---|---|---|---|
| 2007/0060501 A1 | 3/2007 | Jhamandas et al. | |
| 2007/0071761 A1 | 3/2007 | Seon | |
| 2007/0082044 A1 | 4/2007 | Yeum | |
| 2007/0099946 A1 | 5/2007 | Doshan | |
| 2007/0265293 A1 | 11/2007 | Boyd et al. | |
| 2008/0194611 A1 | 8/2008 | Alverdy et al. | |
| 2008/0274119 A1 | 11/2008 | Moss et al. | |
| 2009/0047279 A1* | 2/2009 | Perez | C07D 489/08 514/282 |

FOREIGN PATENT DOCUMENTS

| | | | |
|---|---|---|---|
| CA | 2312234 | 5/1999 | |
| DE | 4303214 | 8/1994 | |
| DE | 19651551 | 6/1998 | |
| EP | 0278821 | 8/1988 | |
| EP | 0289070 | 11/1988 | |
| EP | 0306575 | 3/1989 | |
| EP | 0352361 | 1/1990 | |
| EP | 0506468 | 9/1992 | |
| EP | 0643967 | 3/1995 | |
| EP | 0760661 | 12/1998 | |
| EP | 1047726 | 7/1999 | |
| IE | WO 2008122967 A2 * | 10/2008 | A61K 9/5015 |
| JP | 1068376 | 3/1989 | |
| NZ | 222911 | 12/1987 | |
| WO | WO 83/03197 | 2/1983 | |
| WO | WO 88/05297 | 7/1988 | |
| WO | WO 94/10202 | 5/1994 | |
| WO | WO 95/31985 | 11/1995 | |
| WO | WO 96/14058 | 5/1996 | |
| WO | WO 97/33566 | 9/1997 | |
| WO | WO 97/33608 | 9/1997 | |
| WO | WO 98/02441 | 1/1998 | |
| WO | WO 98/25613 | 6/1998 | |
| WO | WO 99/15530 | 4/1999 | |
| WO | WO 99/22737 | 5/1999 | |
| WO | WO 99/36470 | 7/1999 | |
| WO | WO 01/13909 | 3/2001 | |
| WO | WO 01/14387 | 3/2001 | |
| WO | WO 01/19828 | 3/2001 | |
| WO | WO 01/32180 | 5/2001 | |
| WO | WO 01/37785 | 5/2001 | |
| WO | WO 01/41705 | 6/2001 | |
| WO | WO 01/42207 | 6/2001 | |
| WO | WO 01/70031 | 9/2001 | |
| WO | WO 01/85257 | 11/2001 | |
| WO | WO 02/40000 | 5/2002 | |
| WO | WO 02/060870 | 8/2002 | |
| WO | WO 02/080975 | 10/2002 | |
| WO | WO 02/098422 | 12/2002 | |
| WO | WO 03/020296 | 3/2003 | |
| WO | WO 03/032990 | 4/2003 | |
| WO | WO 03/037340 | 5/2003 | |
| WO | WO 2004/004598 | 1/2004 | |
| WO | WO 2004/014291 | 2/2004 | |
| WO | WO 2004/043964 | 5/2004 | |
| WO | WO 2004/080996 | 9/2004 | |
| WO | WO 2004/091623 | 10/2004 | |
| WO | WO 2004091622 A1 * | 10/2004 | A61K 9/0031 |
| WO | WO 2005/027972 | 3/2005 | |
| WO | WO 2005/027973 | 3/2005 | |
| WO | WO 2005/047289 | 5/2005 | |
| WO | WO 2005/049021 | 6/2005 | |
| WO | WO 2005/082411 | 9/2005 | |
| WO | WO 2005/097107 | 10/2005 | |
| WO | WO 2006/002365 | 1/2006 | |
| WO | WO 2006/057951 | 6/2006 | |
| WO | WO 2006/065780 | 6/2006 | |
| WO | WO 2006/096626 | 9/2006 | |
| WO | WO 2006/125540 | 11/2006 | |
| WO | WO 2006/127899 | 11/2006 | |
| WO | WO 2006/128660 | 12/2006 | |
| WO | WO 2006/132963 | 12/2006 | |
| WO | WO 2007/041544 | 4/2007 | |
| WO | WO 2007/057457 | 5/2007 | |
| WO | WO 2007/059106 | 5/2007 | |
| WO | WO 2007/061737 | 5/2007 | |
| WO | WO 2007061737 A2 * | 5/2007 | C07D 253/07 |
| WO | WO 2007/064993 | 6/2007 | |
| WO | WO 2007/080124 | 7/2007 | |
| WO | WO 2007/053194 | 8/2007 | |
| WO | WO 2007/087395 | 8/2007 | |
| WO | WO 2007/121447 | 10/2007 | |
| WO | WO 2007/124252 | 11/2007 | |
| WO | WO 2007/131689 | 11/2007 | |
| WO | WO 2007/143212 | 12/2007 | |
| WO | WO 2008/016633 | 2/2008 | |
| WO | WO 2008/019115 | 2/2008 | |
| WO | WO 2008/027013 | 3/2008 | |
| WO | WO 2009/117669 | 9/2009 | |

OTHER PUBLICATIONS

Altier, N. et al., Opioid receptors in the ventral tegmental area contribute to stress-induced analgesia in the formalin test for tonic pain. Brain Res. Apr. 29, 1996;718(1-2):203-6.

Alverdy et al., "Influence of the critically ill state on host-pathogen interactions within the intestine: gut-derived sepsis redefined," Crit. Care Med. (2003) 31(2):598-607.

Alverdy, J. et al., "Gut-derived sepsis occurs when the right pathogen with the right verulence genes meets the right host: evidence for in vivo virulence expression and Pseudomonas aeruginosa," Ann. Surg. (2000) 232(4):480-489.

Alverdy, J.C. et al., "Surgical stress, bacteria, and mucosal immune function," Eur. J. Pediatr. Surg. (1999) 9:210-213.

Amin, H.M. et al., Efficacy of methylnaltrexone versus naloxone for reversal of morphine-induced depression of hypoxic ventilatory response. Anesth Analg. Apr. 1994;78(4):701-5.

Amir, S. et al., Endorphins in endotoxin-induced hyperglycemia in mice. Arch Toxicol Suppl. 1983;6:261-5.

Amir, S., Naloxone improves, and morphine exacerbates, experimental shock induced by release of endogenous histamine by compound 48/80. Brain Res. Apr. 9, 1984;297(1):187-90.

Anderson, G.L. et al., "Assessing behavior toxicity with Caenorhabditis elegans," Environ. Toxicol. Chem. (2004) 23:1235-1240.

Angus, D.C. et al., Epidemiology of sepsis: an update, Crit. Care Med. (2001) 29(7):S109-S116.

Arai, M. et al., "Contribution of adenosine $A_2$ receptors and cyclic adenosine monophosphate to protective ischemic preconditioning of sinusoidal Ecs against storage/reperfusion injury in rat livers," Hepatology (2000) 32:297-302.

Arbo, M.D. et al., "Utility of serial rectal swab cultures for detection of ceftazidime- and imipenem-resistant gram-negative bacilli from patients in the invensive care unit," Eur. J. Clin. Microbiol. Infect. Dis. (1998) 17:727-730.

Arendt, R.M. et al., "Bidirectional effects of endogenous opioid peptides on endothelin release rates in porcine aortic endothelial cell culture: mediation by δ opioid receptor and opioid receptor antagonist-insensitive mechanisms," J. Pharmacol. Exp. Thera. (1995) 272(1):1-7.

Arerangaiah, R. et al., "Opioids induce renal abnormalities in tumor bearing mice," Nephron. Exp. Nephrol. (2007) 105:e80-e89.

Argentieri, T.M. et al., Interaction of the opiate antagonist, naltrexone methyl bromide, with the acetylcholine receptor system of the motor end-plate. Brain Res. Oct. 31, 1983;277(2):377-9.

Armstead, W.M., "Relationship between NO, the $K_{ATP}$ channel, and opioids in hypoxic pial artery dilation," Am. J. Physiol. (1998) 275:H988-H994—Abstract 3720.

Armstrong, S. et al., "The gastrointestinal activity and peripheral selectivity of alvimopan, ADL08-0011, and naloxone in mice," May 21, 2006 DDW Presentation in Los Angeles, Clinical Pharm. Therap. (2005) 77:74.

Aung, H.H. et al., Methylnaltrexone prevents morphine-induced kaolin intake in the rat. Life Sci. Apr. 16, 2004;74(22):2685-91.

(56) References Cited

OTHER PUBLICATIONS

Autar, R. et al, "Adhesion inhibition of F1C-fimbriated *Escherichia coli* and Pseudomonas aeruginosa PAK and PAO by multivalent carbohydrate ligands," Chembiochem. (2003) 4:1317-1325.

Azghani, A.O. et al., "Pseudomonas aeruginosa outer membrane protein F is an adhesin in bacterial binding to lung epithelial cells in culture," Microb. Pathog. (2002) 33(3):109-114.

Bajolet-Laudinat, O. et al., "Cytoxicity of Pseudomonas aeruginosa internal lectin PA-I to respiratory epithelial cells in primary culture," Infect. Immun. (1994) 62(10):4481-4487.

Baker, A.K. et al., Functional effects of systemically administered agonists and antagonists of mu, delta, and kappa opioid receptor subtypes on body temperature in mice. J Pharmacol Exp Ther. Sep. 2002;302(3):1253-64.

Balasubramanian, S. et al., "Morphine sulfate inhibits hypoxia-induced vascular endothelial growth factor expression in endothelial cells and cardiac myocytes," J. Mol. Cell Cardiol. (2001) 33(12):2179-2187.

Baratti, C.M. et al., Brain opioid peptides may participate in the reversal of pentylenetetrazol-induced amnesia. Meth. Find Exp Clin Pharmacol. Sep. 1990;12(7):451-6.

Barie, P.S., "Surviving sepsis," Surg. Infect. (2004) 5:1-2.

Basilisco, G. et al., Effect of loperamide and naloxone on mouth-to-caecum transit time evaluated by lactulose hydrogen breath test. Gut. Jul. 1985;26(7):700-3.

Basilisco, G. et al., Oral naloxone antagonizes loperamide-induced delay of orocecal transit, Dig. Dis. Sci. Aug. 1987; 32(8):829-832.

Becker, P.M. et al., "Differential regulation of diverse physiological responses to VEGF in pulmonary endothelial cells," Am. J. Physiol. Lung Cell Mol. Physiol. (2001) 281:L1500-L1511.

Bedingfield, J.B. et al., Methylnaltrexone attenuates taste aversion conditioned by low-dose ethanol. Alcohol. Jan. 1998;15(1):51-4.

Belcheva, M.M. et al., "μ opioid transactivation and down-regulation of the epidermal growth factor receptor in astrocytes: implications for mitogen-activated protein kinase signaling," Mol. Pharmacol. (2003) 64(6):1391-1401.

Belcheva, M.M. et al., "μ-opioid receptor-mediated ERK activation involves calmodulin-dependent epidermal growth factor receptor transactivation," J. Biol. Chem. (2001) 276(36):33847-33853.

Berkes, J. et al., "Intestinal epithelial responses to enteric pathogens: effects on the tight junction barrier, ion transport, and inflammation," Gut (2003) 52:439-451.

Bertani, I. et al., "Role of GacA, LasI, RhlI, Ppk, PsrA, Vfr and ClpXP in the regulation of the stationary-phase sigma factor rpoS/RpoS in Pseudomonas," Arch Microbiol. (2003) 180:264-271.

Bianchetti, A. et al., Quaternary derivatives of narcotic antagonists: stereochemical requirements at the chiral nitrogen for in vitro and in vivo activity. Life Sci. 1983;33 Suppl 1:415-8.

Bianchi, G. et al., Quaternary narcotic antagonists' relative ability to prevent antinociception and gastrointestinal transit inhibition in morphine-treated rats as an index of peripheral selectivity. Life Sci. May 31, 1982;30(22):1875-83.

Bickel, M., Stimulation of colonic motility in dogs and rats by an enkephalin analogue pentapeptide. Life Sci. 1983;33 Suppl 1:469-72.

Bigliardi, P.I. et al., "Different expression of μ-opiate receptor in chronic and acute wounds and the effect of β-endorphin on transforming growth factor β type II receptor and cytokeratin 16 expression," J. Invest. Dermatol. (2003) 120:145-152.

Bigliardi-Qi, M. et al., "Changes of epidermal Mu-opiate receptor expression and nerve endings in chronic atopic dermatitis," Dermatology (2005) 210:91-99.

Birukov, K.G. et al., "Magnitude-dependent regulation of pulmonary endothelial cell barrier function by cyclic stretch," Am. J. Physiol. Lung Cell Mol. Physiol. (2003)285:L785-797.

Birukova, A.A. et al., "Role of Rho GTPases in thrombin-induced lung vascular endothelial cells barrier dysfunction," Microvascular Res. (2004) 67:64-77.

Blank, M.S. et al., Central, stereoselective receptors mediate the acute effects of opiate antagonists on luteinizing hormone secretion. Life Sci. Oct. 27, 1986;39(17):1493-99.

Blebea, J. et al., "Differential effects of vascular growth factors on arterial and venous angiogenesis," J. Vasc. Surg. (2002) 35(3):532-538.

Blebea, J. et al., "Opioid growth factor modulates angiogenesis," J. Vasc. Surg. (2000) 32(2):364-373.

Bogatcheva, N.V. et al., "Molecular mechanisms of thrombin-induced endothelial cell permeability," Biochemistry (2002) 67(1):75-84.

Bolin, I. et al., "Identification of Helicobacter pylori by immunological dot blot method based on reaction of a species-specific monoclonal antibody with a surface-exposed protein," J. Clin. Mirobiol. (1995) 33:381-384.

Bonn, D., "Morphine stimulates tumour growth," Lancet Oncology (2002) 3(9):520.

Boonstra, B. et al., "Engineering novel biocatalytic routes for production of semisynthetic opiate drugs," Biomol. Eng. (2001) 18:41-47.

Bowen, C.A. et al., Antagonism of the antinociceptive and discriminative stimulus effects of heroin and morphine by 3-methoxynaltrexone and naltrexone in rhesus monkeys. J Pharmacol Exp Ther. Jul. 2002;302(1):264-73.

Bowen, S.E. et al., College on Problems of Drug Dependence 64th Annual Scientific Meeting. Jun. 8-13, 2002. Quebec City, Quebec, Canada. Abstracts. Drug Alcohol Depend. May 1, 2002;66 Suppl 1:S19, Abstract No. 65.

Braun, F. et al., "Kinetics and localization of interleukin-2, interleukin-6, heat shock protein 70, and interferon gamma during intestinal-reperfusion injury," Transplant Proc. (2004) 36:267-269.

Brix-Christensen, V. et al., "Endogenous morphine levels increase following cardiac surgery as part of the antiinflammatory response," Int. J. Cardiol. (1997) 62:191-197.

Brix-Christensen, V. et al., Endogenous morphine is produced in response to cardiopulmonary bypass in neonatal pigs. Acta Anaesthesiol Scand. Nov. 2000;44(10):1204-8.

Brown, D.R. et al., Opiate antagonists: central sites of action in suppressing water intake of the rat. Brain Res. Sep. 28, 1981;221(2):432-6.

Brown, D.R. et al., Reversal of morphine-induced catalepsy in the rat by narcotic antagonists and their quaternary derivatives. Neuropharmacology. Mar. 1983;22(3):317-21.

Brown, D.R. et al., The use of quaternary narcotic antagonists in opiate research. Neuropharmacology. Mar. 1985;24(3):181-91.

Brown, L.F. et al., "Expression of vascular permeability factor (vaxcular endothelial growth factor) by epidermal keratinocytes during wound healing," J. Exp. Med. (1992) 176:1375-1379.

Brown, T.D. et al., Techniques for mechanical stimulation of cells in vitro: a review. J Biomech. Jan. 2000;33(1):3-14.

Bruce, N.C. et al., "Microbial degradation of the morphine alkaloids: identification of morphine as an intermediate in the metabolism of morphine by Pseudomonas putida M10," Arch Microbiol. (1990) 154:465-470.

Caballero-Hernandez, D. et al., "Potentiation of rat lymphocyte proliferation by novel non-peptidic synthetic opioids," Int. Immunopharmacol. (2005) 5(7-8):1271-1278.

Cadet, M. et al., "Molecular identification and functional expression of $μ_3$, a novel alternative spliced variant of the human μ opiate receptor gene," J. Immunol. (2003) 170:5118-5123.

Cadet, P. et al., "Differential expression of the human μ opiate receptor from different primary vascular endothelial cells," Med. Sci. Monit. (2004) 10(10):BR351-355.

Calcagnetti, D.J. et al., Quaternary naltrexone reveals the central mediation of conditional opioid analgesia. Pharmacol Biochem Behav. Jul. 1987;27(3):529-31.

Calfee, M.W. et al., "Interference with pseudomonas quinolone signal synthesis inhibits virulence factor expression by pseudomonas aeruginosa," Proc. Natl. Acad. Sci. USA (2001) 98(20):11633-11637.

Cancernetwork.com, "Cancer Pain Remedy Wins Orphan Drug Status," Research Reports in Oncology (1996) 10(12):1880, 2 pages.

(56) References Cited

OTHER PUBLICATIONS

Cao, C.M. et al., "Cardioprotection of interleukin-2 is mediated via κ-opioid receptors," J. Pharmacol. Exp. Ther. (2004) 309:560-567.
Carmeliet, P. et al., "Angiogenesis in cancer and other diseases," Nature (2000) 407:249-257.
Carr, D.J.J. et al., Naltrexone antagonizes the analgesic and immunosuppressive effects of morphine in mice. J Pharmacol Exp Ther. May 1994;269(2):693-8.
Cascone, I. et al., "Tie-2-dependent activation of RhoA and Rac1 participates in endothelial cell motility triggered by angiopoietin-1," (2003) 102(7):2482-2490.
Chancey, S.T. et al., "Two-component transcriptional regulation of N-acyl-homoserine lactone production in pseudomonas aureofaciens," Appl. Environ. Microbiol. (1999) 65:2294-2299.
Chang, E.B. et al., An antiabsorptive basis for precipitated withdrawal diarrhea in morphine-dependent rats. J Pharmacol Exp Ther. Feb. 1984;228(2):364-9.
Chang, S.L. et al., "Morphine affects the brain-immune axis by modulating an interleukin-1 β dependent pathway," In: AIDS, Drugs of Abuse and the Neuroimmune Axis, New York, Plenum Publishing Corp., Friedman et al. eds. (1996) 35-42.
Chang, S.L. et al., "The association between opiates and cytokines in disease," Adv. Exp. Med. Biol. (1998) 437:4-6.
Chen, C. et al., "Catecholamines modulate *Escherichia coli* O157:H7 adherence to murine cecal mucosa," Shock (2003) 20:183-188.
Chen, C. et al., "Morphine stimulates vascular endothelial growth factor-like signaling in mouse retinal endothelial cells," Curr. Neurovas. Res. (2006) 3:171-180.
Chiu, H.H. et al., "Bacteremia and fugemia in hematological and oncological children with neutropenic fever: two-year study in a medical center," J. Microbiol. Immunol. Infect. (1998) 31:101-106.
Choi, Y.S. et al., Inhibition of chemokine-induced chemotaxis of monkey leukocytes by mu-opioid receptor agonists. In Vivo. Sep.-Oct. 1999;13(5):389-96.
Choi, Y.S. et al., Opioid antagonists: a review of their role in palliative care, focusing on use in opioid-related constipation. J Pain Symptom Manage. Jul. 2002;24(1):71-90. Review.
Cioci, G. et al., "Structural basis of calcium and galactose recognition by the lectin PA-IL of Pseudomonas aeruginosa," FEBS Lett. (2003) 555:297-301.
Clark, N.M. et al, "Antimicrobial resistance among gram-negative organisms in the intensive care unit," Curr. Opin. Crit. Care (2003) 9:413-423.
Clauser, K.R. et al., "Role of accurate mass measurement (+/− 10 ppm) in protein identification strategies employing MS or MS/MS and database searching," Anal. Chem. (1999) 71:2871-2882.
Collins, S.L. et al., "Peak plasma concentrations after oral morphine: a systematic review," J. Pain Symptom Management (1998) 16(6):388-402.
Cozzolino, D. et al., "Acute effects of β-endorphin on cardiovascular function in patients with mild to moderate chronic heart failure," Am. Heart J. (2004) 148(E13):1-7.
Culpepper-Morgan, J.A. et al., Treatment of opioid-induced constipation with oral naloxone: a pilot study. Clin Pharmacol Ther. Jul. 1992;52(1):90-5 Abstract.
Dancik, V. et al., "De novo peptide sequencing via tandem mass spectrometry," J. Comput. Biol. (1999) 6:327-342.
Davies, A.G. et al., "A central role of the BK potassium channel in behavioral responses to ethanol in C. elegans," Cell (2003) 115:655-666.
Davies, A.G. et al., "Natural variation in the npr-1 gene modifies ethanol responses of wild strains of C. elegans," Neuron. (2004) 42:731-743.
Davies, A.G. et al., "Using C. elegans to screen for targets of ethanol and behavior-altering drugs," Biol. Proced. Online (2004) 6:113-119.

De Jonge, E. et al., "Effects of selective decontamination of digestive tract on mortality and acquisition of resistant bacteria in intensive care: a randomised controlled trial," Lancet (2003) 362:1011-1016.
De Kievit, T.R. et al., "Quorum-sensing genes in pseudomonas aeruginosa biofilms: their role and expression pattern," App. Environ. Microbiol. (2001) 67:1865-1873.
De Kievit, T.R. et al., "Role of the pseudomonas aeruginosa las and rhl quorum-sensing systems in rhlI regulation," FEMS Microbiol. Lett (2002) 212:101-106.
De Ponti, F. et al., Methylnaltrexone Progenics. Curr Opin Investig Drugs. Apr. 2002;3(4):614-20. Review.
Dechelotte, A. et al., "Uptake, 3-, and 6-glucuronidation of morphine in isolated cells from stomach, intestine, colon, and liver of the guinea pig," Drug Metab. Dispos. (1993) 21:13-17.
Deziel, E. et al., "Analysis of pseudomonas aeruginosa 4-hydroxy-2-alkylquinolines (HAQs) reveals a role for 4-hydroxy-2-heptylquinoline in cell-to-cell communication," Proc. Natl. Acad. Sci USA (2004) 101:1339-1344.
Diggle, S.P. et al., "Advancing the quorum in Pseudomonas aeruginosa: MvaT and the regulation of N-acylhomoserine lactone production and virulence gene expression," J. Bacteriol. (2002) 184:2576-2586.
Diggle, S.P. et al., "The Pseudomonas aeruginosa quinolone signal molecule overcomes the cell density-dependency of the quorum sensing hierarchy, regulates rhl-dependent genes at the onset of stationary phase and can be produced in the absence of LasR," Mol. Microbiol. (2003) 50:29-43.
Doherty, M.M et al., "Route-dependent metabolism of morphine in the vascularly perfused rat small intestine preparation," Pharm. Res. (2000) 17(3):291-298.
Dudek, S.M. et al., "Cytoskeletal regulation of pulmonary ascular permeability," J. Appl. Physiol. (2001) 91:1487-1500.
Dunlap, P.V., "Quorum regulation of luminescence in vibrio fischeri," J. Mol. Microbiol. Biotechnol. (1999) 1:5-12.
Egan, T.D. et al., Prospective pharmacokinetic and pharmacodynamic validation of propofol's context sensitive T1/2. Anesthesiology. Sep. 1999;91(3A): Abstract A347.
Eisenberg, R.M., Effects of naltrexone on plasma corticosterone in opiate-naïve rats: a central action. Life Sci. Mar. 19, 1984;34(12):1185-91.
Eisenstein, K et al., "Effect of opioids on oral *Salmonella* infection and immune function," Adv. Exp. Med. Biol. (2001) 493:169-176.
El-Tawil, A.M., Medscape, "Extracolonic Motility Abnormalities," http://www.medscape.com/viewarticle/442893_4 (Nov. 6, 2007) see pp. 3-4—from Persistence of Abdominal Symptoms after Successful Surgery from South. Med. J. (2002) 95(9):1042-1046.
Epstein, A.M. et al., "Naltrexone attenuates acute cigarette smoking behavior," Pharmacology Biochem. Behavior (2004) 77(1):29-37.
Esposito, S. et al, "Bacterial infections in intensive care units: etiology and pathogenesis," Infez. Med. (1997) 5:145-159.
Essar, D.W. et al., "Identification and characterization of genes for a second anthranilate synthase in pseudomonas aeruginosa: interchangeability of the two anthranilate synthases and evolutionary implications," J. Bacteriol. (1990) 172:884-900.
Exadaktylos, A.K. et al., Can anesthetic technique for primary breast cancer surgery affect recurrence or metastatis? Anesthesiology (2006) 105:660-664.
Fagerlind, M.G. et al., "The role of regulators in the expression of quorum-sensing signals in Pseudomonas aeruginosa," J. Mol. Microbiol. Biotechnol. (2004) 6:88-100.
Farooqui, M. et al., "Mu opioid receptor stimulates a growth promoting and pro-angiogenic tumor microenvironment," Proc. Amer. Assoc. Cancer Res. (2005) 46:Abstract #4650, AACR Meeting Abstracts.
Farooqui, M. et al., "Naloxone acts as an antagonist of estrogen receptor in MCF-7 cells," Mol. Cancer Ther. (2006) 5(3):611-620.
Farthing, M.J.G. et al., New drugs in the management of the irritable bowel syndrome. Drugs. Jul. 1998;56(1):11-21.
Faura, C.C. et al., "Systematic review of factors affecting the ratios of morphine and its major metabolites," Pain (1998) 74:43-53.
Fenchel, T., "Microbial behavior in a heterogeneous world," Science (2002) 296:1068-1071.

(56) References Cited

OTHER PUBLICATIONS

Fernandez-Tome, M.P. et al., Interaction between opioid agonists or naloxone and 5-HTP on feeding behavior in food-deprived rats. Pharmacol Biochem Behav. Feb. 1998;29(2):387-92.

Fingl, E. et al., Chapter 43: Laxatives and cathartics. In Pharmacological Basis of Therapeutics. 1980: 1002-1012.

Finigan, J.H. et al., "Activated protein C mediates novel lung endothelial barrier enhancement," J. Biol. Chem. (2005) 280(17):17286-17293.

Finn, A.K. et al., "Endocytosis of the mu opioid receptor reduces tolerance and a cellular hallmark of opiate withdrawal," Neuron. (2001) 32:829-839.

Fleiszig, S.M. et al., "Pseudomonas aeruginosa-mediated cytotoxicity and invasion correlate with distinct genotypes at the loci encoding exoenzyme S," Infect. Immun. (1997) 65:579-586.

Flores, L.R. et al., Mechanisms of morphine-induced immunosuppression: effect of acute morphine administration on lymphocyte trafficking. J Pharmacol Exp Ther. Mar. 1995;272(3):1246-51.

Foss, J. et al., "Alvimopan (ENTEREG), a novel opioid antagonist, achieves active systemic concentrations," Amer. Soc. Clin. Pharma & Thera. (2005) PII-90, p. 74.

Foss, J.F. et al., "Methylnaltrexone does not antagonize the analgesic effect of morphine: a clinical study," (1995) ASA Abstracts, Annual Scientific Meeting of the American Society of Anesthesiologists, Atlanta, Georgia, Oct. 21-25, 1995, 83(3A Suppl):A361.

Foss, J.F. et al., Dose-related antagonism of the emetic effect of morphine by methylnaltrexone in dogs. J Clin Pharmacol. Aug. 1993;33(8):747-51.

Foss, J.F. et al., Effects of methylnaltrexone on morphine-induced cough suppression in guinea pigs. Life Sci. 1996;59(15):PL235-8.

Foss, J.F. et al., Enteric-coated methylnaltrexone prevents opioid-induced oral-cecal transit delay in humans. Anesth Analg. 2000;90. Abstract S409.

Foss, J.F. et al., Methylnaltrexone reduces morphine-induced postoperative emesis by 30%. Anesth Analg. 1994;78:S119.

Foss, J.F. et al., Prevention of apomorphine- or cisplatin-induced emesis in the dog by a combination of methylnaltrexone and morphine. Cancer Chemother Pharmacol. 1998;42(4):287-91.

Foss, J.F. et al., Safety and tolerance of methylnaltrexone in healthy humans: a randomized, placebo-controlled, intravenous, ascending-dose, pharmacokinetic study. J Clin Pharmacol. Jan. 1997;37(1):25-30.

Foss, J.F. et al., Subcutaneous methylnaltrexone reduces morphine-induced subjective effects in humans. Anesthesiology. 2001;95. Abstract A-817.

Foss, J.F. et al., The efficacy or oral methylnaltrexone in decreasing the subjective effects of IV morphine. Anesth Analg. 1997;84. Abstract S484.

Foss, J.F., A review of the potential role of methylnaltrexone in opioid bowel dysfunction. Am J Surg. Nov. 2001;182(5A Suppl):19S-26S.

Fox, J.G. et al., "Host and microbial constituents influence Helicobacter pylori-induced cancer in a murine model of hypergastrinemia," Gastroenterology (2003) 124:1879-1890.

France, C.P. et al., Comparison of naltrexone and quaternary naltrexone after systemic and intracerebroventricular administration in pigeons. Neuropharmacology. Jun. 1987;26(6):541-8.

France, C.P. et al., Intracerebroventricular drug administration in pigeons. Pharmacol Biochem Behav. Nov. 1985;23(5):731-6.

France, C.P. et al., Morphine, saline and naltrexone discrimination in morphine-treated pigeons. J Pharm and Exper Ther. 1987;242:195-202.

Frassdorf, J. et al., "Morphine induces late cardioprotection in rat hearts in vivo: the involvement of opioid receptors and nuclear transcription factor-κB," Anesth. Analg. (2003) 101:934-941.

French, C.E. et al., "Purification and characterization of morphinone reductase from Pseudomonas putida M10," Biochem. J. (1994) 301 (Pt. 1):97-103.

Friedman, J.D. et al., "Opioid antagonists in the treatment of opioid-induced constipation and pruritus," Ann. Pharmacother. (2001) 35(1):85-91.

Funke, C.W. et al., A proton and carbon-13 nuclear magnetic resonance study of three quaternary salts of naloxone and oxymorphone. J Chem Soc. 1986:735-8.

Furuta, G.T. et al., "Hypoxia-inducible factor 1-dependent induction of intestinal trefoil factor protects barrier function during hypoxia," J. Exp. Med. (2001) 193:1027-1034.

Gainor, J.P. et al., "Platelet-conditioned medium increases endothelia electrical resistance independently of cAMP/PKA and cGMP/PKG," Am. J. Physiol. Heart Circ. Physiol. (2001) 281:H1992-2001.

Garcia, J.G.N. et al., "Diperoxovanadate alters endothelial cell focal contacts and barrier function: role of tyrosine phosphorylation," J. Appl. Physiol. (2000) 89:2333-2343.

Garcia, J.G.N. et al., "Mechanisms of ionomycin-induced endothelial cell barrier dysfunction," Am. J. Physiol. (1997) 273:L172-L184.

Garcia, J.G.N. et al., "Spingosine 1-phosphate promotes endothelial cell barrier integrity by Edg-dependent cytoskeletal rearrangement," J. Clin. Invest. (2001) 108(5):689-701.

Gervitz, C., "Targeted approach: methylnaltrexone blocks opioid-induced constipation and other peripheral side effects," Topics in Pain Management (2005) 21(1):6-8.

Giles, T. et al., Quaternary opiate antagonists lower blood pressure and inhibit leucine-enkephalin responses. Eur J Pharmacol. Nov. 25, 1983;95(3-4):247-52.

Glick, J. et al., "The intracellular localization of Pseudomonas aeruginosa lectins," J. Gen. Microbiol. (1983) 129(Pt 10):3085-3090.

Gmerek, D.E. et al., Independent central and peripheral mediation of morphine-induced inhibition of gastrointestinal transit in rats. J Pharmacol Exp Ther. Jan. 1986;236(1):8-13.

Golden, T.R. et al., "Oxidative stress and aging: beyond correlation," Aging Cell (2002) 1:117-123.

Goodman, A.L. et al., "Analysis of regulatory networks in Pseudomonas aeruginosa by genomewide transcriptional profiling," Curr. Opin. Microbiol. (2004) 7:39-44.

Goumon, Y. et al., "Ascaris suum, an intestinal parasite, produces morphine," J. Immunol (2000) 165:339-343.

Gouvea, E.F. et al., "Outcome of infections caused by multiple drug-resistant bacteria in liver transplant recipients," Transplant Proc. (2004) 36:958-960.

Granata, F. et al., "Expression of OP4 (ORL1, NOP1) receptors in vascular endothelium," Eur. J. Pharmacol. (2003) 482:17-23.

Griffith, S.J. et al., "The epidemiology of Pseudomonas aeruginosa in oncology patients in a general hospital," J. Infect. Dis. (1989) 160:1030-1036.

Gupta, K. et al., "Angiogenesis: a curse or cure?" Postgrad Med. J. (2005) 81:236-242.

Gupta, K. et al., "Morphine exaggerates retinopathy in transgenic sickle mice," Blood (ASH Annual Meeting Abstract) (2005) 106:Abstract 209.

Gupta, K. et al., "Morphine mimics VEGF in vascular endothelium, by promoting pro-angiogenic and survival promoting signalling and angiogenesis," FASEB Journal (2002) 16(4):A207 and Annual Meeting of the Professional Research Scientists on Experimental Biology; New Orleans, Louisiana, Apr. 20-24, 2002 (Abstract only).

Gupta, K. et al., "Morphine stimulates angiogenesis by activating proangiogenic and survival-promoting signaling and promotes breast tumor growth," Cancer Res. (2002) 62(15):4491-4498.

Gupta, R.A. et al., "Activation of peroxisome proliferator-activated receptor gamma suppresses nuclear factor kappa B-mediated apoptosis induced by Helicobacter pylori in gastric epithelial cells," J. Biol. Chem. (2001) 276(33):31059-31066.

Gutstein, D.E. et al., Role of inositol 1,4,5-trisphosphate receptors in regulating apoptotic signaling and heart failure. Heart Vessels. 1997;Suppl 12:53-7.

Guy, H.R. et al., "Structural models of Na+, Ca2+, and K+ channels," Ion Channels and Genetic Diseases, Chapter 1, (1995) 1-28.

(56) References Cited

OTHER PUBLICATIONS

Hailes, A.M. et al., "Biological synthesis of the analgesic hydromorphone, an intermediate in the metabolism of morphine, by Pseudomonas putida M10," App. Environ. Microbiol. (1993) 59:2166-2170.

Hanif, K. et al., "Hypotensive effect of novel chimeric peptides of met-enkephalin and FMRFa," Regul. Pept. (2005) 125:155-161.

Hein, D.W. et al., Pharmacological analysis of the discriminative stimulus characteristics of ethylketazocine in the rhesus monkey. J Pharmacol Exp Ther. Jul. 1981;218(1):7-15.

Hellewell, S.B. et al., "A sigma-like binding site in rat pheochromocytoma (PC12) cells: decreased affinity for (+)-benzomorphans and lower molecular weight suggest a different sigma receptor form from that of guinea pig brain," Brain Res. (1990) 527:244-253.

Hendrickson, E.L. et al., "Differential roles of the Pseudomonas aeruginosa PA14 rpoN gene in pathogenicity in plants, nematodes, insects, and mice," J. Bacteriol. (2001) 183:7126-7134.

Hicks, M.E. et al., Differential effects of the novel non-peptidic opioid 4-tyrosylamido-6-benzyl-1,2,3,4 tetrahydroquinoline (CGPM-9) on in vitro rat t lymphocyte and macrophage functions. Life Sci. May 4, 2001;68(24):2685-94.

Hirota, H. et al., Loss of a gp130 cardiac muscle cell survival pathway is a critical event in the onset of heart failure during biomechanical stress. Cell. Apr. 16, 1999;97(2):189-98.

Ho, C.L. et al., Beta-endorphin: peripheral opioid activity of homologues from six species. Int J Pept Protein Res. Apr. 1987;29(4):521-4.

Ho, W.K.K. et al., Suppression of immunological functions in morphine addicted mice. NIDA Res Monogr. 1986;75:599-602.

Ho, W-Z. et al., "Methylnaltrexone antagonizes opioid-mediated enhancement of HIV infection of human blood mononuclear phagocytes," J. Pharm. Exp. Thera. (2003) 307:1158-1162.

Hoang, M.V. et al., "Rho activity critically and selectively regulates endothelial cell organization during angiogenesis," (2004) 101(7):1874-1879.

Hofmann, P. et al., Hypocalcemia during restraint stress in rats. Indication that gastric ulcer prophylaxis by exogenous calcium interferes with calcitonin release. Res Exp Med (Berl). May 30, 1979;175(2):159-68.

Hou, Y.N. et al., "A μ-receptor opioid agonist induces AP-1 and NF-κB transcription factor activity in primary cultures of rat cortical neurons," Neurosci. Lett. (1996) 212:159-162.

Howd, R.A. et al., Naloxone and intestinal motility. Experientia. Oct. 15, 1978;34(10):1310-1.

http://opioids.com/opiates.html, "Endogenous opioids," (Nov. 6, 2007) 4 pages.

Hussain, M.A. et al., Improvement of the oral bioavailability of naltrexone in dogs: a prodrug approach. J Pharm Sci. May 1987;76(5):356-8.

Hussain, M.A. et al., Naltrexone-3-salicylate (a prodrug of naltrexone): synthesis and pharmacokinetics in dogs. Pharm Res. Feb. 1988;5(2):113-5.

Iorio, M.A. et al., Narcotic agonist/antagonist properties of quaternary diastereoisomers derived from oxymorphone and naloxone. Eur J Med Chem. 1984;19(4):301-3.

Jacobs, M.A. et al., "Comprehensive transposon mutant library of Pseudomonas aeruginosa," Proc. Natl. Acad. Sci. USA (2003) 100:14339-14344.

Jalowiec, J.E. et al., Suppression of juvenile social behavior requires antagonism of central opioid systems. Pharmacol Biochem Behav. Jul. 1989;33(3):697-700.

Jankovic, B.D. et al., Quaternary naltrexone: its immunomodulatory activity and interaction with brain delta and kappa opioid receptors. Immunopharmacology. Sep.-Oct. 1994;28(2):105-12.

Jenab, S. et al., "Ethanol and naloxone differentially upregulate delta opioid receptor gene expression in neuroblastoma hybrid (NG108-15) cells," Brain Res. Mol. Brain Res. (1994) 27:95-102.

Johnson, C.E. et al., "Stability of tacrolimus with morphine sulfate, hydromorphone hydrochloride, and ceftazidime during stimulated intravenous coadministration," Am. J. Health-System Pharmacy (1999) 56(2):164-169.

Juhas, M. et al., "Global regulation of quorum sensing and virulence by VqsR in Pseudomonas aeruginosa," Microbiology (2004) 150:831-841.

Kakeji, Y. et al., "Preclinical studies of the combination of angiogenic inhibitors with cytotoxic agents," Invest. New Drugs (1997) 15:39-48.

Karhausen, J. et al., "Implications of hypoxia on mucosal barrier function," Cell Mol. Biol. (2003) 49:77-87.

Kasamatsu, K. et al., "Attenuation of aortic baroreflex responses by microinjections of endomorphin-2 into the rostral ventrolateral medullary pressor area of the rat," Am. J. Physiol. Regul. Integr. Comp. Physiol. (2005) 289:R59-R67.

Kaufman, P.N. et al., Role of opiate receptors in the regulation of colonic transit. Gastroenterology. Jun. 1988;94(6):1351-6.

Kehlet, H. et al., Review of postoperative ileus. Am J Surg. Nov. 2001;182(5A Suppl):3S-10S. Review.

Kim, C. et al., Assay for methylnaltrexone in rat brain regions and serum by high-performance liquid chromatography with coulometric electrochemical detection. Chromatographia. Oct. 1989;28(7-8):359-63.

King, A.C. et al., "Hypothalamic-pituitary-adrenocortical (HPA) axis response and biotransformation of oral naltrexone: preliminary examination of relationship to family history of alcoholism," Neuropsychopharmacology (2002) 26(6):778-788.

Kinsman, R.I. et al., Effect of naloxone on feedback regulation of small bowel transit by fat. Gastroenterology. Aug. 1984;87(2):335-7.

Kirkeby, S. et al., "Lectin interactions with alpha-galactosylated xenoantigens," Xenotransplantation (2002) 9:260-267.

Ko, M.C.H. et al., "Orphanin FQ inhibits capsaicin-induced thermal nociception in monkeys by activation of peripheral ORL1 receptors," Bri. J. Pharmacol. (2002) 135:943-950.

Koblish, M. et al., Behavioral profile of ADL 8-2698, a novel GI-restricted μ opioid receptor antagonist. Society for Neuroscience Abstracts. 2001;27(2):2407.

Kobylecki, R.J. et al., N-Methylnalorphine: definition of N-allyl conformation for antagonism at the opiate receptor. J Med Chem. Nov. 1982;25(11):1278-81.

Koch, B. et al., "Lipopeptide production in Pseudomonas sp. strain DSS73 is regulated by components of sugar beet seed exudate via the Gac two-component regulatory system," Appl. Environ, Microbiol. (2002) 68:4509-4516.

Koczka, K. et al., "Selective quarternization of compounds with morphine skeleton," Acta Chimica Academica Scien. Hung. (1967) 51(4), 393-02.

Kodani, E. et al., "δ opioid receptor-induced late preconditioning is mediated by cyclooxygenase-2 in conscious rabbits," Am. J. Physiol. Heart Circ. Physiol. (2002) 283:H1943-H1957.

Kohler et al., "Components of intestinal epithelial hypoxia activate the virulence circuitry of Pseudomonas," Amer. J. Physio. Gastrointest Liver Physiol. (2005) 288:1048-1054.

Koob, G.F. et al., Effects of opiate antagonists and their quaternary derivatives on heroin self-administration in the rat. J Pharmacol Exp Ther. May 1984;229(2):481-6.

Kosten, T.A. et al., Naltrexone and morphine alter the discrimination and plasma levels of ethanol. Behav Pharmacol. Feb. 1999;10(1):1-13.

Kostic, T., "The effect of opioid antagonists in local regulation of testicular response to acute stress in adult rats," CAS Abstract Document No. 127: 13345, 1997.

Kotake, A.N. et al., "Variations in demethylation of N-methylnaltrexone in mice, rats, dogs, and humans," Xenobiotica (1989) 19(11):1247-1254.

Kromer, W. et al., Endogenous opioids, the enteric nervous system and gut motility. Dig Dis. 1990;8(6):361-73.

Kromer, W. et al., The current status of opioid research on gastrointestinal motility. Life Sci. 1989;44(9):579-89.

(56) References Cited

OTHER PUBLICATIONS

Kropec, A. et al., "Exogenous or endogenous reservoirs of nosocomial Pseudomonas aeruginosa and *Staphylococcus aureus* infections in a surgical intensive care unit," Intensive Care Med. (1993) 19:161-165.

Kurahashi, K. et al., "Pathogenesis of septic shock in Pseudomonas aeruginosa pneumonia," J. Clin. Invest. (1999) 104:743-750.

Lai, H.P. et al., "Bacteremia in hematological and oncological children with febrile neutropenia: experience in a tertiary medical center in Taiwan," J. Microbiol. Immunol Infect. (2003) 36:197-202.

Lau, G.W. et al., "Pseudomonas aeruginosa pyocyanin is critical for lung infection in mice," Infect. Immun. (2004) 72(7):4275-4278.

Laughlin, R.S. et al., "The key role of Pseudomonas aeruginosa PA-I lectin on experimental gut-derived sepsis," Ann. Surg. (2000) 232:133-142.

Law, P.Y. et al., "Agonist activation of δ-opioid receptor but not μ-opioid receptor potentiates fetal calf serum or tyrosine kinase receptor-mediated cell proliferation in a cell-line-specific manner," Mol. Pharmacol. (1997) 51:152-160.

Law, P.Y. et al., "Properties of delta opioid receptor in neuroblastoma NS20Y: receptor activation and neuroblastoma proliferation," J. Pharmacol. Exp. Ther. (1995) 272(1):322-332.

Law, P.Y. et al., "Regulation of opioid receptor activities," J. Pharmacol. Exp. Ther. (1999) 289:607-624.

Leander, J.D., A kappa opioid effect: increased urination in the rat. J Pharmacol Exp Ther. Jan. 1983;224(1):89- 94.

Ledgham, F. et al., "Interactions of the quorum sensing regulator QscR: interaction with itself and the other regulators of Pseudomonas aeruginosa LasR and RhlR," Mol. Microbiol. (2003) 48:199-210.

Li, Y. et al., Methadone enhances human immunodeficiency virus infection of human immune cells. J Infect Dis. Jan. 1, 2002;185(1):118-22. Epub Dec. 14, 2001.

Lim, Y.J. et al., "Morphine preconditions Purkinje cells against cell death under in vitro simulated ischemia-reperfusion conditions," Anesthesiol. (2004) 100(3):562-568.

Lingen, M.W., "Endothelial Cell Migration Assay. A Quantitative Assay for Prediction of In Vivo Biology," Methods in Molecular Medicine, Wound Healing, Methods and Protocols (2003) 78:337-347.

Little, P.J.et al., ADL 8-2698, a GI restricted opioid antagonist, blocks the antisecretory and colorectal transit effects of morphine and loperamide. Society for Neuroscience Abstracts. 2001; 27(2):2407. Abstract.

Liu, Y. and Senger, D.R., "Matrix-specific activation of Src and Rho initiates capillary morphogenesis of endothelial cells," FASEB J. (2004) 18:457-468.

Livermore, D.M., "The threat from the pink corner," Ann. Med. (2003) 35:226-234.

Livingston, E.H. et al., Postoperative ileus. Dig Dis Sci. Jan. 1990;35(1):121-32.

Lopez, Y. et al., Demonstration of long-lasting blockade of experimental ileus in rats by an opioid k-agonist. Gastroenterology. 1995;108(4):A640. Abstract.

Lory, S. et al., "The multi-talented bacterial adenylate cyclases," Int. J. Med. Microbiol. (2004) 293:479-482.

Lydon, A. et al., "Intravenous methylnaltrexone attenuates intrathecal morphine induced delayed gastric emptying in rats," ESA Free Paper Prize Competition. Eur J Anaesthesiol. Apr. 2001;18 Suppl 21:92, Abstract A-327.

Lysle, D.T. et al., Modulation of immune status by a conditioned aversive stimulus: evidence for the involvement of endogenous opioids. Brain Behav Immun. Jun. 1992;6(2):179-88.

Lyte, M. et al., "Stimulation of *Staphylococcus epidermidis* growth and biofilm formation by catecholamine inotropes," Lancet (2003) 361:130-135.

Machelska, H. et al., "Selectins and integrins but not platelet-endothelial cell adhesion molecule-1 regulate opioid inhibition of inflammatory pain," Br. J. Pharmacol. (2004) 142:772-780.

Mack, D.J. et al., Paralytic ileus: response to naloxone. Br J Surg. Oct. 1989;76(10):1101.

Magazine, H.I. et al., "Morphine-induced conformational changes in human monocytes, granulocytes, and endothelial cells and in invertebrate immunocytes and microglia are mediated by nitric oxide," J. Immunol (1996) 156:4845-4850.

Magnan, J. et al., The binding spectrum of narcotic analgesic drugs with different agonist and antagonist properties. Naunyn Schmiedebergs Arch Pharmacol. Jun. 1982;319(3):197-205.

Manara, L. et al., Peripheral selectivity of quaternary narcotic antagonists: relative ability to prevent gastrointestinal transit inhibition and antinociception in morphinized rats. Adv. Endog. Exog. Opioids, 12th Proc. Int. Narc. Res. Conf., Kyoto, Japan(1981): 402-4.

Manara, L. et al., The central and peripheral influences of opioids on gastrointestinal propulsion. Annu Rev Pharmacol Toxicol. 1985;25:249-73.

Marmor, M. et al., "Coronary artery disease and opioid use," Am. J. Cardiol. (2004) 93:1295-1297.

Marshall, J.C. et al., "The ecology and immunology of the gastrointestinal tract in health and critical illness," J. Hosp. Infect. (1991) 19 Suppl. C:7-17.

Marshall, J.C. et al., "The gastrointestinal tract. The 'undrained abcess' of multiple organ failure," Ann. Surg. (1993) 218:111-119.

Matsko, N. et al., "AFM of biological material embedded in epoxy resin," J. Struct. Biol. (2004) 146:334-343.

Matta, H. et al., "An immuno-dot blot assay for detection of thermostable protease from *Pseudomonas* sp. AFT-36 of dairy origin," Lett. Appl. Microbiol. (1997) 25:300-302.

Mavrodi, D.V. et al., "Functional analysis of genes for biosynthesis of pyocyanin and phenazine-1-carboxamide from pseudomonas aeruginosa PAO1," J. Bacteriol. (2001) 183:6454-6465.

McBride, S.M. et al., "$\delta_2$ opioid receptor agonist facilitates mean arterial pressure recovery after hemorrhage in conscious rats," Shock (2005) 23(3):264-268.

McCarthy, R.N. et al., Preliminary studies on the use of plasma β-endorphin in horses as an indicator of stress and pain. J Equine Vet Sci. 1993;13(4):216-9.

McGurl, D., "From Easter Island soil to treating sarcoma-rapamycin derivatives," found at http://liddyshriversarcomaininitiative.org/newsletters/V02N02/rapamycin_derivatives.htm (Mar. 6, 2008) 3 pages).

McKnight, S.L. et al., "The pseudomonas quinolone signal regulates rhl quorum sensing in pseudomonus aeruginosa," J. Bacteriol. (2000) 182:2702-2708.

McLaughlin et al., "Opioid antagonist modulation of rat heart development," Life Sci. (1994) 54(19):1423-1431.

McQuay, H.J., "Opioid problems and morphine metabolism and excretion," taken from http://www.jr2.ox.ac.uk/bandolier/booth/painpag/wisdom/c14.html (Oct. 26, 2005) 34 pages.

McQuay, H.J., "Opioid use in chronic pain," Acta Anaesthesiol. Scand. (1997) 41:175-183.

McVerry, B.J. et al., "In vitro and in vivo modulation of vascular barrier integrity by sphingosine 1-phosphate: mechanistic insights," Cellular Signaling (2005) 17:131-139.

Mehr, S.E. et al., "Inhibition by immunophilin ligands of morphine-induced tolerance and dependence in guinea pig ileum," Eur. J. Pharmacol. (2003) 467(1-3):205-210.

Melzig, M.F. et al., "Stimulation of endothelial angiotensin-converting enzyme by morphine via non-opioid receptor mediated processes," Pharmazie. (1998) 53:634-637.

Mickley, G.A. et al., Quaternary naltrexone reverses morphine-induced behaviors. Physiol Behav. Aug. 1985;35(2):249-53.

Miedema, B.W. et al., Methods for decreasing postoperative gut dysmotility. Lancet Oncol. Jun. 2003;4(6):365-72.

Min, D.H. et al., "Chemical screening by mass spectrometery to identify inhibitors of anthrax lethal factor," Nat. Biotechnol. (2004) 22:717-723.

Misra, A.L. et al., Intravenous kinetics and metabolism of [15,16-3H]naltrexonium methiodide in the rat. J Pharm Pharmacol. Mar. 1987;39(3):225-7.

(56) References Cited

OTHER PUBLICATIONS

Mitchell, E. et al., "Structural basis for oligosaccharide-mediated adhesion of Pseudomonas aeruginosa in the lungs of cystic fibrosis patients," Nat. Struct. Biol. (2002) 9:918-921.

Mitchell, R.N. et al., "The link between IFN-γ and allograft arteriopathy: is the answer No?" J. Clin. Invest. (2004) 114:762-764.

Moerman, I. et al., Evaluation of methylnaltrexone for the reduction of postoperative vomiting and nausea incidences. Acta Anaesthesiol Belg. 1995;46(3-4):127-32.

Moore, T., "Regulation of pulmonary endothelial cell shape by TRP-mediated calcium entry-transient receptor potential," Thomas L. Petty 40th Annual Aspen Lung Conference: Biology and Pathobiology of the Lung Circulation (1998) Chest 114:36S-38S.

Moser, C. et al., "Improved outcome of chronic Pseudomonas aeruginosa lung infection is associated with induction of a Th1-dominated cytokine response," Clin. Exp. Immunol. (2002) 127:206-213.

Moss, J. and Foss, J., "Pain relief without side effects: peripheral opiate antagonists," 33rd ASA Refresher Courses in Anesthesiology, Philadelphia, Lippincott Williams & Wilkins, Schwartz A.J. editor (2006) 175-186.

Moss, J. et al., "Opioid-induced changes in pulmonary barrier integrity may explain heroid-induced pulmonary edema," American Society of Anesthesiologists presentation, Oct. 17, 2007 in San Francisco, CA (Abstract).

Moss, J. et al., Methylnaltrexone prevents morphine-induced CCR5 receptor expression. Anesthesiology. 2003;99. Abstract A-961.

Moss, J. et al., Selective postoperative inhibition of gastrointestinal opioid receptors. N. Engl. J. Med. 2002;346(6):455.

Mucha, R.F., Is the motivational effect of opiate withdrawal reflected by common somatic indices of precipitated withdrawal? A place conditioning study in the rat. Brain Res. Aug. 25, 1987;418(2):214-20.

Mucha, R.F., Taste aversion involving central opioid antagonism is potentiated in morphine-dependent rats. Life Sci. 1989;45(8):671-8.

Murohara, T. et al., "Nitrix oxide synthase modulates angiogenesis in response to tissue ischemia," J. Clin. Invest. (1998) 101(11):2567-2578.

Murono, K. et al., "Molecular comparison of bacterial isolates from blood with strains colonizing pharynx and intestine in immunocompromised patients with sepsis," J. Med. Microbiol. (2003) 52:527-530.

Murphey, E.D. et al., "Diminished bacterial clearance is associated with decreased IL-12 and interferon-gamma production but a sustained proinflammatory response in a murine model of postseptic immunosuppression," Shock (2004) 21:415-425.

Murphy, D.B. et al., "Pharmacokinetic of epidural administered methylnaltrexone a novel peripheral opioid antagonist," American Society of Anesthesiologists 1999 annual meeting. Dallas, Texas, USA. Oct. 9-13, 1999. ASA Abstracts, Anesthesiology, Sep. 1999;91(3A Suppl):A349.

Murphy, D.B. et al., Opioid antagonist modulation of ischaemia-induced ventricular arrhythmias: a peripheral mechanism. J Cardiovasc Pharmacol. Jan. 1999;33(1):122-5.

Murphy, D.B. et al., Opioid-induced delay in gastric emptying: a peripheral mechanism in humans. Anesthesiology. Oct. 1997;87(4):765-70.

Murphy, D.B. et al., Pharmacokinetic profile of epidurally administered methylnaltrexone, a novel peripheral opioid antagonist in a rabbit model. Br J Anaesth. Jan. 2001;86(1):120-2.

Naranjo, J.R. et al., Evidence for a central but not adrenal, opioid mediation in hypertension induced by brief isolation in the rat. Life Sci. May 26, 1986;38(21):1923-30.

Nazli, A. et al., "Epithelia under metabolic stress perceive commensal bacteria as a threat," Am. J. Pathol. (2004) 164:947-957.

Nelson, C.J., "Morphine modulation of the contact hypersensitivity response: a pharmacological and immunological characterization," Dissertation Abstracts International, (2001) (62/03-B), p. 1635 (Abstract).

Nemeth-Lefkowitz, D. et al., "Hematological and immunological effects of methadone administration in mice," Research Communications in Substance Abuse (1980) 1(2): 177-83.

Neuhauser, M.M. et al., "Antibiotic resistance among gram-negative bacilli in U.S. intensive care units: implications for fluoroquinolone use," JAMA (2003) 289:885-888.

Neumann, P.B. et al., "Plasma morphine concentrations during chronic oral administration in patients with cancer pain," Pain (1982) 13:247-252.

Neves, F.O. et al., "Overexpression of a synthetic gene encoding human alpha interferon in *Escherichia coli*," Protein Expr. Purif. (2004) 35:353-359.

Noddin, L. et al., MEDSCAPE, "Irritable bowel syndrome and functional dyspepsia: different diseases or a single disorder with different manifestations?" http://www.medscape.com/viewarticle/506798_5 (Nov. 6, 2007) 3 pages—from Medscape General Medicine (2005) 7(3):17.

Nusrat, A. et al., "Molecular physiology and pathophysiology of tight junctions. IV. Regulation of tight junctions by extracellular stimuli: nutrients, cytokines, and immune cells," Am. J. Physiol. Gastrointest. Liver Physiol. (2000) 279:G851-857.

Odio, M. et al., Central but not peripheral opiate receptor blockade prolonged pituitary-adrenal responses to stress. Pharmacol Biochem Behav. Apr. 1990;35(4):963-9.

Ojielo, C.I. et al., "Defective phagocytosis and clearance of Pseudomonas aeruginosa in the lung following bone marrow transplantation," J. Immunol. (2003) 171:4416-4424.

Olanders, K. et al., "The effect of intestinal ischemia and reperfusion injury on ICAM-1 expression, endothelial barrier function, neutrophil tissue influx, and protease inhibitor levels in rats," Shock (2002) 18:86-92.

Osinski, J. et al., Determination of methylnaltrexone in clinical samples by solid-phase extraction and high-performance liquid chromatography for a pharmacokinetics study. J Chromatogr B Analyt Technol Biomed Life Sci. Nov. 25, 2002;780(2):251-9.

Osmon, S. et al., "Hospital mortality for patients with bacterimia due to *Staphylococcus aureus* or Pseudomonas aeruginosa," Chest (2004) 125:607-616.

O'Toole, G.A. et al., "Initiation of biofilm formation in pseudomonas fluorescens WCS 365 proceeds via multiple, convergent signaling pathways: a genetic analysis," Mol. Microbiol. (1998) 28:449-461.

Papapetropoulos, A. et al., Nitric oxide synthase inhibitors attenuate transforming-growth-factor-beta 1-stimulated capillary organization in vitro. Am J Pathol. May 1997;150(5):1835-44.

Pappagallo, M., Incidence, prevalence, and management of opioid bowel dysfunction. Am J Surg. Nov. 2001;182(5A Suppl):11S-18S.

Parkins, M.D. et al., "Pseudomonas aeruginosa GacA, a factor in multihost virulence, is also essential for biofilm formation," Mol. Microbiol. (2001) 40:1215-1226.

Parsek, M.R. et al., "Acyl-homoserine lactone quorum sensing in gram-negative bacteria: a signaling mechanism involved in associations with higher organisms," Proc. Natl. Acad. Sci. USA (2000) 97:8789-8793.

Parsek, M.R. et al., "Quorum sensing signals in development of Pseudomonas aeruginosa biofilms," Methods Enzymol. (1999) 310:43-55.

Pasi, A. et al., "Angiogenesis: modulation with opioids," Gen. Pharmacol. (1991) 22(6):1077-1079.

Pastores, S.M. et al., "Splanchnic ischemia and gut mucosal injury in sepsis and the multiple organ dysfunction syndrome," Am. J. Gastroenterol. (1996) 91:1697-1710.

Patel, H.H. et al., "COX-2 and iNOS in opioid-induced delayed cardioprotection in the intact rat," Life Sci. (2004) 75:129-140.

Paulson, D.M. et al., "Alvimopan: an oral, peripherally acting, mu-opioid receptor antagonist for the treatment of opioid-induced bowel dysfunction—a 21-day treatment—randomized clinical trial,"J. Pain. (2005) 6(3):184-192.

Pearson, J.P. et al., "Roles of pseudomonas aeruginosa las and rhl quorum-sensing systems in control of elastase and rhamnolipid biosynthesis genes,"J. Bacteriol. (1997) 179:5756-5767.

Peart, J.N. et al., "Opioid-induced preconditioning: recent advances and future perspectives," Vasc. Pharmacol. (2005) 42:211-218.

(56) References Cited

OTHER PUBLICATIONS

Pennisi, E., "Infectious disease. Cholera strengthened by trip through gut," Science (2002) 296:1783-1784.
Pham, P.T.K. et al., Drugs of Abuse: Chemistry, Pharmacology, Immunology and AIDS; National Institute of Drug Research 96: Monograph Series. U.S. Department of Health and Human Services (1990) 1-243.
Podsypanina, K. et al., "An inhibitor of mTOR reduces neoplasia and normalizes p70/S6 kinase activity in Pten+/− mice," Proc. Natl. Acad. Sci. USA (2001) 98(18):10320-10325.
Polak, J.M. et al., Enkephalin-like immunoreactivity in the human gastrointestinal tract. Lancet. May 7, 1977;1(8019):972-4.
Polakiewicz, R.D. et al., "μ-opioid receptor activates signaling pathways implicated in cell survival and translational control," J. Biol. Chem. (1998) 273(36):23534-23541.
Polte, T. et al., "Cyclic AMP mediates endothelial protection by nitric oxide," Biochem. Biophys. Res. Commun. (1998) 251:460-465.
Poonawala, T. et al., "Opioids heal ischemic wounds in the rat," Wound Repair Regen. (2005) 13(2):165-174.
Popov, I., "Systemic treatment of colorectal cancer in Serbia: what have we done and what can offer in the new century?" Acta Chir. Iugosl. (2004) 51(2):117-121.
Powell, K.J. et al., Paradoxical effects of the opioid antagonist naltrexone on morphine analgesia, tolerance, and reward in rats. J Pharmacol Exp Ther. Feb. 2002;300(2):588-96.
Progenics Pharmaceuticals, Inc., "Progenics achieves enrollment target in pivotal phase 3 clinical trial of methylnaltrexone for opioid-induced constipation," Press Release, Dec. 3, 2004.
Progenics Pharmaceuticals, Inc., "Progenics announces positive top-line results from pivotal phase 3 clinical trial of MNTX in opioid-induced constipation," Press Release, Mar. 10, 2005.
Progenics Pharmaceuticals, Inc., "Progenics initiates second phase 3 clinical trial of methylnaltrexone in opioid-induced constipation," Press Release, Jan. 13, 2004.
Pugsley, M.K. et al., "Cardiovascular actions of the κ-agonist U-50,488H in the absence and presence of opioid receptor blockade," Br. J. Pharmacol. (1992) 105:521-526.
Qiao, J. et al., "PKA inhibits RhoA activation: a protection mechanism against endothelial barrier dysfunction," Am. J. Physiol. Lung Cell Mol. Physiol. (2003) 284:L972-L980.
Quang-Contagrel, N.D. et al., Long-term methadone treatment: effect on CD4+ lymphocyte counts and HIV-1 plasma RNA level in patients with HIV infection. Eur J Pain. 2001;5(4):415-20.
Quock, R.M. et al, Microwave facilitation of methylnaltrexone antagonism of morphine-induced analgesia in mice. J Bioelect. 1986;5(1):35-46.
Quock, R.M. et al., Narcotic antagonist potentiation of apomorphine drug effect: a stereospecific, centrally mediated drug action. Prog Neuropsychopharmacol Biol Psychiatry. 1985;9(3):239-43.
Quock, R.M. et al., Narcotic antagonist-induced hypotension in the spontaneously hypertensive rat. Life Sci. Sep. 2, 1985;37(9):819-26.
Raje, N. et al., "Combination of the mTOR inhibitor rapamycin and CC-5013 has synergistic activity in multiple myeloma," Blood (2004) 104(13):4188-4193.
Ramabadran, K., Effects of N-methylnaloxone and N-methylnaltrexone on nociception and precipitated abstinence in mice. Life Sci. Sep. 20-27, 1982;31(12-13):1253-6.
Reimmann et al., "The global activator GacA of pseudomonas aeruginosa PAO positively controls the production of the autoinducer N-butyryl-homoserine lactone and the formation of the virulence factors pyocyanin, cyanide, and lipase," Mol. Microbiol. (1997) 24:309-319.
Remington's Pharmaceutical Sciences, 15th Edition, Mack Publishing Co., (1995) 1614-1615.
Resnick, J. et al., Delayed gastric emptying and postoperative ileus after nongastric abdominal surgery: part I. Am J Gastroenterol. May 1997;92(5):751-62.
Resnick, J. et al., Delayed gastric emptying and postoperative ileus after nongastric abdominal surgery: part II. Am J Gastroenterol. Jun. 1997;92(6):934-40.
Risdahl, J.M. et al., "Opiates and infection," J. Neuroimmunol. (1998) 83:4-18.
Rivière, P.J.M. et al., Fedotozine reverses ileus induced by surgery or peritonitis: action at peripheral kappa-opioid receptors. Gastroenterology. Mar. 1993;104(3):724-31.
Robinson, B.A. et al., Oral naloxone in opioid-associated constipation. Lancet. Aug. 31, 1991;338(8766):581-2.
Rocha, F. et al., "Surgical stress shifts the intestinal *Escherichia coli* population to that of a more adherent phenotype: role in barrier regulation," Surgery (2001) 130:65-73.
Roger, Th. et al., Colonic motor responses in the pony: relevance of colonic stimulation by opiate antagonists. Am J Vet Res. Jan. 1985;46(1):31-5.
Rojas, M. et al., "A dot-blot assay for adhesive components relative to probiotics," Methods Enzymol. (2001) 336:389-402.
Roy, S. et al., "Morphine modulates NF κ B activation in macrophages," Biochem. Biophys. Res. Commun. (1998) 245:392-396.
Russell, J. et al., Antagonism of gut, but not central effects of morphine with quaternary narcotic antagonists. Eur J Pharmacol. Mar. 12, 1982;78(3):255-61.
Sachs, D. et al., "Peripheral analgesic blockade of hypernociception: activation of arginine/NO/cGMP/protein kinase G/ATP-sensitive K + channel pathway," Proc. Natl. Acad. Sci. USA (2004) 101(10):3680-3685.
Sakurada, S. et al., Differential antagonism of endomorphin-1 and endomorphin-2 supraspinal antinociception by naloxonazine and 3-methylnaltrexone. Peptides. May 2002;23(5):895-901.
Sala, R. et al., "Protection by N-acetylcysteine against pulmonary endothelial cell damage induced by oxidant injury," Eur. Respir. J. (1993) 6:440-446.
Sanchez-Plumed, J.A. et al., "Sirolimus, the first mTOR inhibitor," Nefrologia (2006) 26:21-32.
Sandner-Keisling, A. et al., Pharmacology of opioid inhibition to noxious uterine cervical distension. Anesthesiology. Oct. 2002;97(4):966-71.
Sansonetti, P., "Host-pathogen interactions: the seduction of molecular cross talk," Gut (2002) 50 Suppl. 3:iii2-8.
Sawa, T. et al., "In vitro cellular toxicity predicts Pseudomonas aeruginosa virulence in lung infections," Infect. Immun. (1998) 66:3242-3249.
Schaefer, G.J. et al., Effects of opioid antagonists and their quaternary derivatives on locomotor activity and fixed ratio responding for brain self-stimulation in rats. Pharmacol Biochem Behav. Nov. 1985;23(5):797-802.
Schang, J.C. et al., Beneficial effects of naloxone in a patient with intestinal pseudoobstruction. Am J Gastroenterol. Jun. 1985;80(6):407-11.
Schang, J.C. et al., How does morphine work on colonic motility? An electromyographic study in the human left and sigmoid colon. Life Sci. Feb. 24, 1986;38(8):671-6.
Schiller, L.R. et al., Studies of the mechanism of the antidiarrheal effect of codeine. J Clin Invest. Nov. 1982;70(5):999-1008.
Schmidhammer, H. et al., Synthesis and biological evaluation of 14-alkoxymorphinans. Part 10[1]. 14-O-methyl derivatives of 5-methylnalthrexone and 5-methylnaloxone. Helv Chim Acta. 1994; 77(6):1585-9.
Schmidhammer, H. et al., Synthesis and biological evaluation of 14-alkoxymorphinans. Part 9[1]. 14-O-ethyl-5-methylnaltrexone, an opioid antagonist with unusual selectivity. Helv Chim Acta. 1993;(1):476-80.
Schmidt, W.K., "Alvimopan (ADL 8-2698) is a novel peripheral opioid antagonist," Am. J. Surg. (2001) 182(5A Suppl):11S-18S.
Schmith, V.D. et al., "Alvimopan pharmacokinetics (PK) and Pharmacodynamics (PD) in patients with chronic constipation (CC)," Clinical Pharmacology & Therapeutics (2005) 77(2) P49.
Scholz, M., Managing constipation that's opioid-induced. 2000; 63(6):103.

(56) References Cited

OTHER PUBLICATIONS

Schreier, W.A. et al., Central regulation of intestinal function: morphine withdrawal diarrhea. Proc West Pharmacol Soc. 1982;25:151-4.
Schubert-Zsilavecz, V.M. et al., Das reizdarmsyndrom irritable bowel syndrome. Deutsche apotheker zeitung. Aug. 22, 2002; 142(34): 40-9.
Schultz, M.J. et al., "Endogenous interferon-gamma impairs bacterial clearance from lungs during Pseudomonas aeruginosa pneumonia," Eur. Cytokine Netw. (2001) 12:39-44.
Schuster, M. et al., "Identification, timing, and signal specificity of Pseudomonas aeruginosa quorum-controlled genes: a transcriptome analysis," J. Bacteriol. (2003) 185:2066-2079.
Schuster, M. et al., "Promoter specificity in pseudomonas aeruginosa quorum sensing revealed by DNA binding of purified LasR," Proc. Natl. Acad. Sci. USA (2004) 101(45):15833-15839.
Schuster, M. et al., "The Pseudomonas aeruginosa RpoS regulon and its relationship to quorum sensing," Mol. Microbiol. (2004) 51:973-985.
Schwartzentruber, D.J. et al., "Specific release of granulocyte-macrophage colony-stimulating factor, tumor-necrosis factor-α, and IFN-γ by human tumor-infiltrating lymphocytes after autologous tumor stimulation,"J. Immunol. (1991) 146:3674-3681.
Sezen, S.F. et al., "Renal excretory responses produced by the delta opioid agonist, BW373U86, in conscious rats," J. Pharmacol. Exp. Ther. (1998) 287:238-245.
Shahbazian, A. et al., "Involvement of μ- and κ-, but not δ-, opiod receptors in the peristaltic motor depression caused by endogenous and exogenous opiods in the guinea pig intestine," Br. J. Pharmacol. (2002) 135:741-750.
Shapira, M. et al., "The mTOR inhibitor rapamycin down-regulates the expression of the ubiquitin ligase subunit Skp2 in breast cancer cells," Breast Cancer Res. (2006) 8:R46.
Shavit, Y. et al., Effects of a single administration of morphine or footshock stress on natural killer cell cytotoxicity. Brain Behav Immun. Dec. 1987;1(4):318-28.
Shi, E. et al., "Cardioprotective effects of morphine on rat heart suffering from ischemia and reperfusion," Chin. Med. J. (Engl) (2003) 116:1059-1062.
Singleton, P.A. et al., "CD44 interaction with ankyrin and IP3 receptor in lipid rafts promotes hyaluronan-mediated Ca2+ signaling leading to nitric oxide production and endothelial cell adhesion and proliferation," Exp. Cell Res. (2004) 295:102-118.
Singleton, P.A. et al., "CD44v10 interaction with Rho-kinase (ROK) activates inositol 1,4,5-triphosphate (IP3) receptor-mediated Ca2+ signaling during hyaluronan (HA)-induced endothelial cell migration," Cell Motility and the Cytoskeleton (2002) 53:293-316.
Singleton, P.A. et al., "Regulation of sphingosine 1-phosphate-induced endothelial cytoskeletal rearrangement and barrier enhancement by S1P1 receptor, PI3 kinase, Tiaml/Racl, and a-actinin," FASEB Journal (2005) 19:1646-1656.
Singleton, P.A. et al., "Methylnaltrexone inhibits opiate and VEGF-induced angiogenesis: role of receptor transactivation," Microvasc. Res. (2006) 72(1-2):3-11.
Singleton, P.A. et al., "Attenuation of vascular permeability by methylnaltrexone. Role of mOP-R and S1P3 transactivation," Am. J. Respir. Cell Mol. Biol. (2007) 37(2):222-231.
Smith, M.G. et al., "Microbial synergy via an ethanol-triggered pathway," Mol. Cell Biol. (2004) 24:3874-3884.
Smith, R.S. et al., "An adenylate cyclase-controlled signaling network regulates Pseudomonas aeruginosa virulence in a mouse model of acute pneumonia," Infect. Immun. (2004) 72:1677-1684.
Smith, R.S. et al., "P. aeruginosa quorum-sensing systems and virulence," Curr. Opin. Microbiol. (2003) 6:56-60.
Soldani, G. et al., Central and peripheral involvement of mu receptors in gastric secretory effects of opioids in the dog. Eur J Pharmacol. Nov. 19, 1985;117(3):295-301.
Solvason, H.B. et al., Naltrexone blocks the expression of the conditioned elevation of natural killer cell activity in BALB/c mice. Brain Behav Immun. Sep. 1989;3(3):247-62.

Sperandio, V. et al., "Bacteria-host communication: the language of hormones," Proc. Natl. Acad. Sci USA (2003) 100:8951-8956.
Srinivasan, A. et al., "An outbreak of Pseudomonas aeruginosa infections associated with flexible bronchoscopes," N. Eng. J. Med. (2003) 348:221-227.
Stanski, D.R. et al., "Kinetics of intravenous and intramuscular morphine," Clin. Pharmacol. Ther. (1978) 24(1):52-59.
Stefano, G.B. et al., "Long-term exposure of human blood vessels to HIV gp120, morphine, and anandamide increases endothelial adhesion of monocytes: uncoupline of nitric oxide release," J. Cardiovasc. Pharmacol. (1998) 31:862-868.
Stefano, G.B. et al., "Morphine enhances nitric oxide release in the mammalian gastrointestinal tract via the micro(3) opiate receptor subtype: a hormonal role for endogenous morphine," J. Physiol. Pharmacol. (2004) 55:279-288.
Stefano, G.B. et al., "Presence of the μ3 opiate receptor in endothelial cells. Coupling to nitric oxide production and vasodilation," J. Biol. Chem. (1995) 270:30290-30293.
Stefano, G.B. et al., "δ-2 opioid receptor subtype on human vascular endothelium uncouples morphine stimulated nitric oxide release," Int. J. Cardiol. (1998) 64(Suppl. 1):543-551.
Steidler, L. et al., "Treatment of murine colitis by Lactococuss lactis secreting interleukin-10," Science (2000) 289:1352-1355.
Steinbrook, R.A. et al., An opioid antagonist for postoperative ileus. N. Engl J Med. Sep. 27, 2001;345(13):988-9.
Stephenson, E.J. et al., "μ opioid receptor stimulates a growth promoting and pro-angiogenic tumor microenvironment by transactivating VEGF receptor-2/Flk-1," Blood (ASH Annual Meeting Abstracts (2005) 106:Abstract 3687.
Stephenson, J. et al., Methylnaltrexone reverses opioid-induced constipation. Lancet Oncol. Apr. 2002;3(4):202.
Sternini, C. et al., "The opioid system in the gastrointestinal tract," Neurogastroenterol Motil. (2004) 16 Suppl 2, 3-16.
Stevens, T. et al., "Mechanisms regulating endothelial cell barrier function," Am. J. Physiol. Lung Cell Mol. Physiol. (2002) 279:L419-L422.
Stiene-Martin, A. et al., "Regional, developmental, and cell cycle-dependent differences in μ, δ, and κ-opioid receptor expression among cultured mouse astrocytes," Glia (1998) 22:249-259.
Stover, C.K. et al., "Complete geome sequence of pseudomonas aeruginosa PAO1, an opportunistic pathogen," Nature (2000) 406:959-964.
Strohmeier, G.R. et al., "Surface expression, polarization, and functional significance of CD73 in human intestinal epithelia," J. Clin. Invest. (1997) 99:2588-2601.
Sun, J. et al., "Bacterial activation of beta-catenin signaling in human epithelia," Am. J. Physiol. Gastrointest. Liver Physiol. (2004) 287:G220-G227.
Sun, Z. et al., "Gut barrier permeability, reticuloendothelial system function and protease inhibitor levels following intestinal ischaemia and reperfusion—effects of pretreatment with N-acetyl-L-cysteine and indomethacin," Dig. Liver Dis. (2002) 34:560-569.
Suzuki, S. et al., "Morphine suppresses lymphocyte spoptosis by blocking p53-mediated death signaling," Biochem. Biophys. Res. Commun. (2003) 308:802-808.
Swan, N.et al., NIDA plays key role in studying links between AIDS and drug abuse. AIDS Research, NIDA Notes. 1995; 10(3):1-6.
Sykes, N.P., "Using oral naloxone in management of opioid bowel dysfunction," Handbook of Opioid Bowel Syndrome, New York, Haworth Medical Press, Yuan, C-S. editor (2005) Chapter 9, 175-195.
Sykes, N.P., Oral naloxone in opioid-associated constipation. Lancet. Jun. 15, 1991;337(8755):1475.
Taguchi, A. et al., "Selective postoperative inhibition of gastrointestinal opioid receptors," N. Engl. J. Med. (2001) 345:935-940.
Talley, N.J. et al., Pharmacologic therapy for the irritable bowel syndrome. Am J Gastroenterol. Apr. 2003;98(4):750-8.
Tan, M.W. et al., "Killing of caenorhabditis elegans by Pseudomonas aeruginosa used to model mammalian bacterial pathogenesis," Proc. Natl. Acad. Sci. USA (1999) 96:715-720.
Tegeder, I. et al., "Opioids as modulators of cell death and survival—unraveling mechanisms and revealing new indications," Pharm. Rev. (2004) 56(3):351-369.

(56) References Cited

OTHER PUBLICATIONS

Thomas, J. et al., "A phase III double-blind placebo-controlled trial of methylnaltrexone (MNTX) for opioid-induced constipation (OIC) in advanced medical illness (AMI)," Abstract No. LBA8003 from the 2005 ASCO Annual Meeting (3 pages).
Thomas, J. et al., Amelioration of peripheral side effects of opioids: clinical experience with methylnaltrexone (MNTX). Proc World Congr Anesth. 2004:107.
Thompson, A.C. et al., Opioid stimulation in the ventral tegmental area facilitates the onset of maternal behavior in rats. Brain Res. Dec. 16, 1996;743(1-2):184-201.
Thompson, W.G. et al., Laxatives: clinical pharmacology and rational use. Drugs. Jan. 1980;19(1):49-58.
Tiruppathi, C. et al., "Endothelial permeability/pulmonary edema," Circ. Res. (2002) 91(1):70-76.
Tomiyasu, S. et al., Analysis of intercostal nerve damage associated with chronic post-thoracotomy pain. Anesthesiology. 2001;95. Abstract A-964.
Trebichavsky, I. et al., "Systemic and local cytokine response of young piglets to oral infection with *Salmonella enterica* serotype Typhimurium," Folia Microbiol. (2003) 48:403-407.
Tryoen-Toth, P. et al., "Regulation of κ-opioid receptor mRNA level by cyclic AMP and growth factors in cultured rat glial cells," Mol. Brain Res. (1998) 55:141-150.
Tsikitis, V.L. et al., "The lectin-like domain of compliment receptor 3 protects endothelial barrier function from activated neutrophils," J. Immuno. (2004) 173:1284-1291.
Turner, J.R. et al., "Physiological regulation of epithelial tight junctions is associated with myosin light-chain phosphorylation," Am. J. Physiol. Cell Physiol. (1997) 273:C1378-C1385.
Uccelletti, D. et al., "Ire-1-dependent transcriptional up-regulation of a lumenal uridine diphosphatase from Caenorhabditis elegans," J. Biol. Chem. (2004) 279:27390-27398.
Ukai, M. et al., Suppression of deprivation-induced water intake in the rat by opioid antagonists: central sites of action. Psychopharmacology (Berl). 1987;91(3):279-84.
Valentino, R.J. et al., Quaternary naltrexone: evidence for the central mediation of discriminative stimulus effects of narcotic agonists and antagonists. J Pharmacol Exp Ther. Jun. 1981;217(3):652-9.
Valentino, R.J. et al., Receptor binding, antagonist, and withdrawal precipitating properties of opiate antagonists. Life Sci. Jun. 20, 1983;32(25):2887-96.
Vallejo, R. et al., "Opioid therapy and immunosuppression: a review," Am. J. Ther. (2004) 11:354-365.
Venturi, V., "Control of rpoS transcription in *Escherichia coli* and Pseudomonas: why so different?" Mol. Microbiol. (2003) 49:1-9.
Viswanathan, V.K. et al., "Microbes and their products—physiological effects upon mammalian mucosa," Adv. Drug Delivery Res. (2004) 56:727-762.
Wagner, V.E. et al., "Microarray analysis of Pseudomonas aeruginosa quorum-sensing regulons: effects of growth phase and environment," J. Bacteriol. (2003) 185:2080-2095.
Waldhoer, M. et al., "Opioid receptors," Annu. Rev. Biochem. (2004) 73:953-990.
Walker, M.J.K. et al., Role of central versus peripheral opioid receptors in analgesia induced by repeated administration of opioid antagonists. Psychopharmacology. 1991;104(2):164-6.
Walsh, D. et al., "The symptoms of advanced cancer: relationship to age, gender, and performance status in 1,000 patients," Support Care Cancer (2000) 8:175-179.
Wang, J. et al., "Morphine negatively regulates interferon-γ promoter activity in activated murine T cells through two distinct cyclic AMP-dependent pathways," J. Biol. Chem. (2003) 278(39):37622-37631.
Wang, J. et al., "The immunosuppressive effects of chronic morphine treatment are partially dependent on corticosterone and mediated by the υ-opioid receptor," J. Leukoc. Biol. (2002) 71:782-790.
Wang, X. et al., "A non-peptide substance P antagonist (CP-96,345) inhibits morphine induced NF-κ B promoter activation in human NT2-N neurons," J. Neurosci. Res. (2004) 75:544-553.
Warren, P.H. et al., Effects of quaternary naltrexone and chlordiazepoxide in squirrel monkeys with enhanced sensitivity to the behavioral effects of naltrexone. J Pharmacol Exp Ther. Nov. 1985;235(2):412-7.
Wei, G. et al., "Effects of subcutaneous methylnaltrexone on morphine-induced gut motility changes: a clinical trial," Abstracts of the 2002 Annual Meeting of the American Society for Clinical Pharmacology and Therapeutics. Atlanta, Georgia, USA. Mar. 24-27, 2002. Clin Pharmacol Ther. Feb. 2002;71(2):MPI-26.
Wei, G. et al., Opioid-induced immunosuppression: is it centrally mediated or peripherally mediated? Biochem Pharmacol. Jun. 1, 2003;65(11):1761-6.
Wei, G. et al., Pharmacokinetics of subcutaneous methylnaltrexone: different route administration comparison. 2001. ASA Annual Meeting Abstracts. Oct. 14-18, 2001. Chicago, IL. Abstract A-962.
West, S.E. et al., "Construction of improved *Escherichia*-Pseudomonas shuttle vectors dervied from pUC18/19 and sequence of the region required for their replication in Pseudomonas aeruginosa," Gene (1994) 148(1):81-86.
Westerman, B.A. et al., "C2360, a nuclear protein expressed in human proliferative cytotrophoblasts, is a representative member of a novel protein family with a conserved coiled coil-helix-coiled coil-helix domain," Genomics (2004) 83:1094-1104.
Wetzker, R. et al., "Transactivation joins multiple tracks to the ERK/MAPK cascade," Nat. Rev. (2003) 4:651-657.
Whistler, C.A. et al., "The two-component regulators GacS and GacA influence accumulation of the stationary-phase sigma factor sigmaS and the stress response in Pseudomonas fluorescens Pf-5," J. Bacteriol. (1998) 180:6635-6641.
Whistler, J.L. et al., "Functional dissociation of μ opioid receptor signaling and endocytosis: implications for the biology of opiate tolerance and addiction," Neuron (1999) 23:737-746.
Whistler, J.L. et al., "Modulation of postendocytic sorting of G protein-coupled receptors," Science (2002) 297:615-620.
White, F.A. et al., "Chemokines: integrators of pain and inflammation," Nature Rev. Drug Discovery (2005) 4:834-844.
Whiteley, M. et al., "Idenfitication of genes controlled by quorum sensing in Pseudomonas aeruginosa," Proc. Natl. Acad. Sci USA (1999) 96:13904-13909.
Whiteley, M. et al., "Promoter specificity elements in Pseudomonas aeruginosa quorum-sensing-controlled genes," J. Bacteriol. (2001) 183:5529-5534.
Whiteley, M. et al., "Regulation of quorum sensing by RpoS in Pseudomonas aeruginosa," J. Bacteriol. (2000) 182:4356-4360.
Willett, C.G. et al., "Direct evidence that the VEGF-specific antibody bevacizumab has antivascular effects in human rectal cancer," Nature Med. (2004) 10(2):145-147.
Willette, R.N. et al., "Evidence for anticholinergic effects of naltrexone methylbromide," Res Comm Subst Abuse (1983) 4(4):325-37.
Wilmore, D.W. et al., Can we minimize the effects of opioids on the bowel and still achieve adequate pain control? Am J Surg. Nov. 2001;182(5A Suppl):1S-2S.
Winzer, K. et al., "LuxS: its role in central metabolism and the in vitro synthesis of 4-hydroxy-5-methyl-3(2H)-furanone," Microbiology (2002) 148:909-922.
Winzer, K. et al., "Quorum sensing and the regulation of virulence gene expression in pathogenic bacteria," Int. J. Med. Microbiol. (2001) 291:131-143.
Winzer, K. et al., "The Pseudomonas aeruginosa lectins PA-IL and PA-IIL are controlled by quorum sensing and by RpoS," J. Bacteriol. (2000) 182:6401-6411.
Wittert, G. et al., "Tissue distribution of opioid receptor gene expression in the rat," Biochem. Biophys. Res. Commun. (1996) 218:887-881.
Wolff, B.G. et al., "Alvimopan, a novel, peripherally acting μ opioid antagonist. Results of a multicenter, randomized, double-blind, placebo-controlled, phase III trial of major abdominal surgery and postoperative ileus," Ann. Surg. (2004) 240(4):728-735.

(56) References Cited

OTHER PUBLICATIONS

Wolfgang, M.C. et al., "Coordinate regulation of bacterial virulence genes by a novel adenylate cyclase-dependent signaling pathway," Dev. Cell (2003) 4:253-263.
Wu, L. et al., "Highmolecular-weight polyethylene glycol prevents lethal sepsis due to intestinal Pseudomonas aeruginosa," Gastroenterology (2004) 126:488-498.
Wu, L. et al., "Pseudomonas aeruginosa expresses a lethal virulence determinant, the PA-I lectin/adhesin, in the intestinal tract of a stressed host: the role of epithelia cell contact and molecules of the quorum sensing signaling system," Ann. Surg. (2003) 238:754-764.
Wu, L.R. et al., "Surgical injury and metabolic stress enhance the virulence of the human opportunistic pathogen Pseudomonas aeruginosa," Surgical Infections (2005) 6(2):185-195.
Wybran, J. et al., Suggestive evidence for receptors for morphine and methionine-enkephalin on normal human blood T lymphocytes. J Immunol. Sep. 1979;123(3):1068-70.
Xie, P. et al., "Activation of NF-κ B by bradykinin through a G-$\alpha_q$- and Gβ γ-dependent pathway that involves phosphoinositide 3-kinase and Akt," J. Biol. Chem. (2000) 275(32):24907-24914.
Xu, D.Z. et al., "The effect of hypoxia/reoxygenation on the cellular function of intestinal epithelial cells," J. Trauma (1999) 46:280-285.
Xu, J. et al., "Message from a human gut symbiont: sensitivity is a prerequisite for sharing," Trends Microbiol. (2004) 21-28.
Yarwood, J.M. et al., "Quorum sensing in *Staphylococcus aureus* biofilms," J. Bacteriol. (2004) 186:1838-1850.
Yoshida, S. et al., "Effect of surgical stress on endogenous morphine and cytokine levels in the plasma aafter laparoscopic or open cholecystectomy," Surg. Endosc. (2000) 14:137-140.
Yu, H. et al., "Innate lung defenses and compromised Pseudomonas aeruginosa clearance in the malnourished mouse model of respiratory infections in cystic fibrosis," Infect. Immun. (2000) 68:2142-2147.
Yuan, C.S. et al., "Methylnaltrexone for reversal of constipation due to chronic methadone use," JAMA (2000) 283(3):367-372.
Yuan, C.S. et al., "Tolerability, gut effects, and pharmacokinetics of methylnaltrexone following repeated intravenous administration in humans," J. Clin. Pharmacol (2005) 45:538-546.
Yuan, C.S. et al., Antagonism of chronic opioid-induce gut effects. Anesth Analg. 2000;90:S1-523. Abstract S479.
Yuan, C.S. et al., Antagonism of gastrointestinal opioid effects. Reg Anesth Pain Med. Nov.-Dec. 2000;25(6):639-42.
Yuan, C.S. et al., Dose-related effects of oral acetaminophen on cold-induced pain: a double-blind, randomized, placebo-controlled trial. Clin Pharmacol Ther. Mar. 1998;63(3):379-83.
Yuan, C.S. et al., Effects of enteric-coated methylnaltrexone in preventing opioid-induced delay in oral-cecal transit time. Clin Pharmacol Ther. Apr. 2000;67(4):398-404.
Yuan, C.S. et al., Effects of intravenous methylnaltrexone on opioid-induced gut motility and transit time changes in subjects receiving chronic methadone therapy: a pilot study. Pain. Dec. 1999;83(3):631-5.
Yuan, C.S. et al., Effects of low-dose morphine on gastric emptying in healthy volunteers. J Clin Pharmacol. Nov. 1998;38(11):1017-20.
Yuan, C.S. et al., Effects of methylnaltrexone on chronic opioid induced gut motility and transit time changes. Br J Anaesth. 1998;81(1):94.
Yuan, C.S. et al., Effects of methylnaltrexone on chronic opioid-induced gut motility and transit time changes. University of Leicester—Abstracts from the Eighth International Symposium on Pain, Anaesthesia and Endocrinology. Sep. 18-19, 1997.
Yuan, C.S. et al., Effects of methylnaltrexone on morphine-induced inhibition of contraction in isolated guinea-pig ileum and human intestine. Eur J Pharmacol. Mar. 24, 1995;276(1-2):107-11.
Yuan, C.S. et al., Effects of methylnaltrexone on morphine-induced inhibition of contractions in isolated guinea-pig and human intestine. Anesthesiology. Sep. 1995; 83(3A). Abstract A358.
Yuan, C.S. et al., Effects of subcutaneous methylnaltrexone on morphine-induced peripherally mediated side effects: a double-blind randomized placebo-controlled trial. J Pharmacol Exp Ther. Jan. 2002;300(1):118-23.
Yuan, C.S. et al., Efficacy of orally administered methylnaltrexone in decreasing subjective effects after intravenous morphine. Drug Alcohol Depend. Oct. 1, 1998;52(2):161-5.
Yuan, C.S. et al., Gastric effects of methylnaltrexone on mu, kappa, and delta opioid agonists induced brainstem unitary responses. Neuropharmacology. Mar. 1999;38(3):425-32.
Yuan, C.S. et al., Gastric effects of mu-, delta- and kappa-opioid receptor agonists on brainstem unitary responses in the neonatal rat. Eur J Pharmacol. Oct. 24, 1996;314(1-2):27-32.
Yuan, C.S. et al., Gut and brain effects of American ginseng root on brainstem neuronal activities in rats. Amer J Chin Med. 1998; 26: 47-55.
Yuan, C.S. et al., Gut motility and transit changes in patients receiving long-term methadone maintenance. J Clin Pharmacol. Oct. 1998;38(10):931-5.
Yuan, C.S. et al., Methylnaltrexone (MNTX) for chronic opioid-induced constipation. 2002 ASCO Annual Meeting. Proc Am Soc Clin Oncol. 2002;21:376a. Abstract 1501.
Yuan, C.S. et al., Methylnaltrexone (MNTX) reverses chronic opioid constipation: a double-blind, randomized, placebo-controlled trial. Anesthesiology. Sep. 1999; 91 (3A). Abstract A973.
Yuan, C.S. et al., Methylnaltrexone changes gut motility and transit time in chronic methadone-maintained subjects. Anesth Analg. 1999;88: S1-424. Abstract S404.
Yuan, C.S. et al., Methylnaltrexone effects on morphine-induced inhibition in isolated guinea-pig and human intestine. Clin Pharm & Therapeut. Feb. 1995;57:138. Abstract PI-11.
Yuan, C.S. et al., Methylnaltrexone prevents morphine-induced delay in oral-cecal transit time without affecting analgesia: a double-blind randomized placebo-controlled trial. Clin Pharmacol Ther. Apr. 1996;59(4):469-75.
Yuan, C.S. et al., Methylnaltrexone prevents morphine-induced kaolin intake in the rat. Anesthesiology. 2003;99. Abstract A-922.
Yuan, C.S. et al., Methylnaltrexone reduces oral-cecal transit time in humans. Dig Dis Week Abstr. 2003:A-578. Abstract T1840.
Yuan, C.S. et al., Methylnaltrexone reverses morphine-induced changes in gastrointestinal motility: a clinical study. Anesthesiology Sep. 1995; 83(3A): Abstract A360.
Yuan, C.S. et al., Methylnaltrexone: investigation of clinical applications. Drug Develop Res. 2000;50(2):133-41.
Yuan, C.S. et al., Opioid analgesia without gut side effects: effects of methylnaltrexone as a novel peripheral opioid antagonist. Assoc Univ Anesth Abst. 2003: PD2.
Yuan, C.S. et al., Oral methylnaltrexone for opioid-induced constipation. JAMA. Sep. 20, 2000;284(11):1383-4.
Yuan, C.S. et al., Oral methylnaltrexone reverses chronic opioid-induced constipation. Anesthesiology. Sep. 2000;93(3A). Abstract A-872.
Yuan, C.S. et al., Oral methylnaltrexone reverses morphine-induced changes in gastrointestinal motility. Anesthesiology. Sep. 1995;85(3A). Abstract A335.
Yuan, C.S. et al., Pain control without side effects: clinical studies on methylnaltrexone as a novel peripheral opioid antagonist. 7th America-Japan Anesth Congr. Yamanashi, Japan. 2002:41.
Yuan, C.S. et al., Pharmacokinetics of intravenous vs. oral methylnaltrexone: evidence for direct gut effects. Anesth Analg. 2001;92: S1-363. Abstract S274.
Yuan, C.S. et al., Safety and tolerance of oral methylnaltrexone in healthy volunteers. Anesth Analg. 1997;84:S1-599. Abstract S574.
Yuan, C.S. et al., Subcutaneous methylnaltrexone prevents morphine-induced delay in gut transit time: a clinical trial. Anesthesiology. 2001;95. Abstract A-963.
Yuan, C.S. et al., The safety and efficacy of oral methylnaltrexone in preventing morphine-induced delay in oral-cecal transit time. Clin Pharmacol Ther. Apr. 1997;61(4):467-75.
Yuan, C.S., "Clinical status of methylnaltrexone: a new agent to prevent and manage opioid-induced side effects," J. Support Oncol. (2004) 2:111-122.

(56) References Cited

OTHER PUBLICATIONS

Yuan, C-S. et al., "Methylnaltrexone, a novel peripheral opiod receptor antagonist for the treatment of opiod side effects," Exp. Opin. Investig. Drugs (2006) 15(5):541-552.
Zagon, I.S. et al., "Opioid antagonists inhibit the growth of metastatic murine neuro blastoma," Cancer Letts. (1983) 21(1):89-94.
Zagon, I.S. et al., "Opioid growth factor regulates the cell cycle of human neoplasias," Int. J. Oncol. (2000) 17(5):1053-1061.
Zagon, I.S. et al., "Opioids and differentiation in human cancer cells," Neuropeptides (2005) 39:495-505.
Zagon, I.S. et al., "Opioids and the apoptotic pathway in human cancer cells," Neuropeptides (2003) 37:79-88.
Zaugg, M. et al., "Anaesthetics and cardiac preconditioning. Part I. Signalling and cytoprotective mechanisms," Br. J. Anaesth. (2003) 91(4):551-565.
Zeng, H. et al., "Heterotrimeric $G\alpha_q/G\alpha_{11}$ proteins function upstream of vascular endothelial growth factor (VEGF) receptor-2 (KDR) phosphorylation in vascular permeability factor/VEGF signaling," J. Biol. Chem. (2003) 278:20738-20745.
Zhang, H. et al., "LPS induces permeability injury in lung microvascular endothelium via AT1 receptor," Biochem. Biophys. (2005) 441:75-83.
Zhang, Y. et al., "Effect of the endogenous ? opioid agonist dynorphin A(1-17) on cocaine-evoked increases in striatal dopamine levels and cocaine-induced place preference in C57BL/6J mice," Psychopharmacology (2004) 172:422-429.
Asai, T., "The specific anti-newborn blood vessel activity of rapamycin and application to cancer therapy," Pharmacia, 2006, vol. 42, No. 2, pp. 173-174 (English Abstract Attached).
Zimmerman, D.M. et al., Discovery of a potent, peripherally selective trans-3,4-dimethyl-4-(3-hydroxyphenyl) piperidine opioid antagonist for the treatment of gastrointestinal motility disorders. J Med Chem. Jul. 22, 1994, 37(15):2262-5.
International Search Report and Written Opinion for Application No. PCT/US2009/037825 dated Oct. 30, 2009 (13 pages).
Office Action from United States Patent and Trademark Office for U.S. Appl. No. 12/933,784 dated Jul. 18, 2012 (9 pages).
Office Action from United States Patent and Trademark Office for U.S. Appl. No. 12/933,784 dated Oct. 30, 2012 (18 pages).
Final Rejection from United States Patent and Trademark Office for U.S. Appl. No. 12/933,784 dated May 17, 2013 (21 pages).
Japanese Patent Office Action for Application No. 2011-500985 dated Sep. 3, 2013 (11 pages).
Canadian Patent Office Action for Application No. 2,719,134 dated Apr. 11, 2014 (2 pages).
European Patent Office Action for Application No. 09723085.8 dated Feb. 12, 2014 (6 pages).
Australian Patent Examination Report No. 1 for Application No. 2013205002 dated Apr. 7, 2015 (4 pages).
Japanese Patent Office Action for Application No. 2014-226368 dated Sep. 29, 2015 (5 pages) English translation.
European Patent Office Action for Application No. 09723085.8 dated Jan. 12, 2016 (6 pages).
Australian Patent Examination Report for Application No. 2013205002 dated Apr. 26, 2016.

* cited by examiner

A. Dose-Response Graph of MNTX Inhibition of VEGF-induced Akt Serine (473) Phosphorylation

B. Dose-Response Graph of MNTX Inhibition of VEGF-induced Akt Threonine (308) Phosphorylation

A.

B.

A. MNTX Inhibition of VEGF-induced Proliferation Synergy is Regulated by Tyrosine Phosphatase Activity

B. MNTX Inhibition of VEGF-induced Migration Synergy is Regulated by Tyrosine Phosphatase Activity

TREATMENT WITH OPIOID ANTAGONISTS AND MTOR INHIBITORS

CROSS-REFERENCE TO RELATED APPLICATIONS

This application is a continuation of U.S. application Ser. No. 12/933,784, filed on Oct. 14, 2010, now U.S. Pat. No. 8,685,995, which is a national stage filing under 35 U.S.C. 371 of International Application No. PCT/US2009/037825, filed on Mar. 20, 2009, which claims the benefit under 35 U.S.C. §119(e) of U.S. Provisional Application No. 61/038,577, filed on Mar. 21, 2008, the complete disclosures of which are incorporated herein by reference in their entireties.

STATEMENT REGARDING FEDERALLY SPONSORED RESEARCH OR DEVELOPMENT

Not applicable.

INTRODUCTION

Cell growth and proliferation are normal ongoing processes in all living organisms, involving numerous factors and signals that are delicately balanced to maintain regular cell cycles. Whether or not mammalian cells will grow and divide is determined by a variety of feedback control mechanisms, such as the availability of space in which a cell can grow, and the secretion of specific stimulatory and inhibitory factors in the immediate environment.

mTOR is a large polypeptide serine/threonine kinase of the phosphatidylinositol 3-kinase (PI3K)-related kinase (PIKK) family. mTOR lies downstream from the PI3K pathway, and functions as an intermediary in a variety of cell signalling events to regulate cell growth and proliferation. mTOR activity is regulated by the serine/threonine kinase Akt, and recent evidence indicates that these kinases interact through a complex feedback inhibition pathway. mTOR modulates cell replication by controlling translation of key proteins that are required for progression of the cell cycle through the G1 to the S phase. That is, mTOR controls the translation of specific mRNAs via regulation of the phosphorylation state of several proteins involved in the translation of mRNA, mainly 4E-PB1, P70S6K and eEFZ.

The mTOR pathway, with its PI3K and Akt constituents, is a critical regulator of the proliferation of cells that responds to nutrients, hormones and growth factors, such as VEGF. Growth factors can activate PI3K signaling by binding to cognate cell surface receptors, thereby initiating a signaling cascade through Akt that results in the activation of mTOR. Recent studies have demonstrated that mTOR inhibitors have antiproliferative and antiangiogenic effects by inhibiting both growth factor-mediated signaling and growth factor translation.

In cancer cells, multiple dysregulation mechanisms within the PI3K pathway upstream of mTOR have been documented as causing increased mTOR activity, and consequently, increasing tumor growth. Thus, dysregulation of the mTOR signaling pathway has been implicated in the progression of cancer, and inhibitors of mTOR are currently being investigated as cancer therapeutic agents. mTOR inhibitors are also potent immunosuppressive agents. One such agent, sirolimus, is currently being used for the prophylaxis of organ rejection. Other mTOR inhibitors that are currently marketed or under development include temsirolimus (Torisel™; Wyeth), RAD001 (everolimus; Novartis), MK-8669 (deforolimus; Merck & Ariad pharma), FK506 (tacrolimus; Astellas), TOP216 (Toptarget A/S), OSI-027 (OSI Pharma), TAFA93 (Isotechnika), and nab-rapamycin (APP Pharma). Many of these mTOR inhibitors are rapamycin or rapamycin derivatives.

In addition to their development as organ transplant rejection prophylaxis and anti-cancer agents, mTOR inhibitors are also being developed for the treatment of rheumatoid arthritis, autoimmune disorders, psoriasis, multiple sclerosis, Parkinson's disease, stroke and peripheral neuropathies. For example, the mTOR inhibitor rapamycin has been shown to have efficacy in several animal models of autoimmunity such as experimental allergic encephalomyelitis, insulin-dependent diabetes mellitus, murine lupus and adjuvant arthritis, and has been proposed as a potential therapy in rheumatoid diseases. As to the latter, antibodies from individuals with rheumatoid or Graves' disease activate fibroblasts through the mTOR pathway, which can be inhibited with rapamycin, suggesting that an mTOR blockade would be of value in limiting inflammation in these diseases. Rapamycin was also found to reduce collagen mRNA levels in human fibroblasts, suggesting that mTOR positively regulates collagen type I synthesis. Thus, mTOR blockade may also be of benefit in fibrotic diseases such as scleroderma, where fibrotic lesions disrupt normal tissue architecture and contribute to organ failure. Protein expression of the CCR5 chemokine receptor utilized by HIV-1 to enter CD4 T cells and macrophages is also inhibited by rapamycin, suggesting a clinical utility for blockade of CCR5-mediated viral entry in immune cells. Recently, rapamycin treatment was shown to significantly reduce clinical disease in a patient with dermatomyositis, an autoimmune condition that affects muscle and skin. mTOR inhibitors also have potent neuroprotective and neuroregenerative properties in culture and animal models.

However, several adverse reactions have been observed with mTOR inhibitors in clinical studies. These include rash, asthenia, mucositis, anorexia, peripheral edema, hypertriglyceridemia, hypertension, hypercholesterolemia, hypercreatinemia, constipation, abdominal pain, diarrhea, headache, fever, urinary tract infection, anemia, nausea, arthralgia, pain, and thrombocytopenia. At least a subset of these adverse reactions appear to be dose dependent.

BRIEF DESCRIPTION

Methods and pharmaceutical combinations embodying the principles of embodiments of the invention include co-administering mTOR inhibitors with a class of compounds generally described as μ-opioid receptor antagonists. The inventors have found that a μ-opioid receptor antagonist, such as methylnaltrexone, can be co-administered with mTOR inhibitors in a synergistic manner that permits reducing the therapeutically effective dosing of the mTOR inhibitors. As noted above, at least a subset of the adverse reactions that are associated with mTOR inhibitors appear to be dose-dependent, and thus, the co-administration of a μ-opioid receptor antagonist allows for the use of decreased doses of these mTOR inhibitors and the concomitant reduction in the incidence and/or severity of adverse reactions. The inventors have demonstrated that methylnaltrexone inhibits the activation of the kinase Akt, which is an upstream event in the activation of mTOR. Akt and mTOR are involved in a complex regulatory feedback loop, and simultaneous targeting of both Akt and mTOR in accordance with embodiments of the invention has a synergistic effect.

The use of µ-opioid receptor antagonists in combination with mTOR inhibitors may greatly increase the anticancer and immunosuppressive efficacy of these inhibitors and allow for their use at lower doses, thus lessening the occurrence/severity of adverse effects. Moreover, use of µ-opioid receptor antagonists, such as methylnaltrexone, to increase the efficacy of these mTOR inhibitors with a resultant decrease in dosing required for a therapeutic effect would also greatly decrease the high cost of treatment associated with mTOR inhibitors. A method of improving the therapeutic index or utility of an mTOR inhibitor by co-administering a synergistically effective amount of an mTOR inhibitor and a µ-opioid receptor antagonist is further contemplated.

Methods embodying the principles of embodiments of the invention include attenuating, e.g., inhibiting or reducing, cell proliferation and migration, particularly endothelial cell proliferation and migration, using a combination of mTOR inhibitors and µ-opioid receptor antagonists, including, but not limited to, those that are peripherally-restricted antagonists. According to an aspect of the invention, a method of treatment is provided that includes administering to a subject with a disorder characterized by unwanted migration and/or proliferation of cells, a synergistically effective amount of an mTOR inhibitor and a µ-opioid receptor antagonist. The treatment may inhibit one or both of migration and proliferation, and the cells may suitably be endothelial cells, and of particular interest, vascular endothelial cells. Thus, in another embodiment, this disorder characterized by unwanted migration or proliferation of vascular endothelial cells is unwanted angiogenesis. In other words, a method of treating unwanted angiogenesis is contemplated.

According to another aspect, methods of attenuating migration and/or proliferation of cells of a tumor or cancer are provided, including contacting the cells with an antimigratory or antiproliferative amount of an mTOR inhibitor and a µ-opioid receptor antagonist. In attenuating abnormal cell proliferation, activation of the mTOR/Akt signaling pathway is inhibited in a mammal by administering to the mammal a synergistic therapeutically effective amount of an mTOR inhibitor and a µ-opioid receptor antagonist. Thus, in accordance with an embodiment of the invention, a method of inhibiting mTOR/Akt pathway signaling in cells, e.g., endothelial cells, is also provided, which method includes contacting the cells with a synergistically effective amount of an mTOR inhibitor and a µ-opioid receptor antagonist. Another embodiment of the invention further includes a method of treating cancerous tissue in a subject including, administering to the subject an amount of an mTOR inhibitor and a µ-opioid receptor antagonist sufficient to inhibit mTOR/Akt pathway-mediated effects in the cancerous tissue, as well as a method including contacting a tissue or a population of cells with a composition or combination including an amount of at least one of an mTOR inhibitor and at least one of a µ-opioid receptor antagonist under conditions effective to synergistically inhibit mTOR/Akt pathway-induced cell proliferation and migration.

In a further aspect, a method of treating a disorder or disease characterized by hyperproliferation of cells is provided, which method includes co-administering to a subject suffering thereof, a synergistically effective amount of an mTOR inhibitor and a µ-opioid receptor antagonist. Yet another embodiment of the invention includes a method of treating cancer, e.g., a method of inhibiting growth of a tumor in a subject in need thereof, which method includes co-administering a synergistically effective amount of an mTOR inhibitor and a µ-opioid receptor antagonist.

A further embodiment of the invention provides a method of treating abnormal proliferation of cells expressing a growth factor receptor in a mammal by administering to the mammal a synergistic therapeutically effective amount of an mTOR inhibitor and a µ-opioid receptor antagonist. In particular embodiments, the growth factor receptor is vascular endothelial growth factor receptor (VEGF-R), epidermal growth factor receptor (EGF-R) or insulin-like growth factor receptor (IGF-R). Thus, in accordance with other embodiments of the invention, a method of inhibiting growth factor signaling in endothelial cells is also provided. In specific embodiments, the growth factor is VEGF, EGF or IGF.

By administering the synergistic combination of mTOR inhibitors and µ-opioid antagonists, in accordance with embodiments of the invention, methods of treatment of autoimmune diseases, psoriasis, neurodegenerative diseases, CCR5-mediated viral entry into immune cells, and nausea and emesis are also contemplated.

Pharmaceutical combinations and packages of mTOR inhibitors and µ-opioid receptor antagonists as well as accompanying instructions for co-administration are also provided in accordance with embodiments of the invention.

mTOR inhibitors for use in the methods in accordance with embodiments of the invention generally include compounds that inhibit cell replication by blocking progression of the cell cycle from G1 to S by inhibiting phosphorylation of serine 389 of p70S6 kinase by mTOR. Known mTOR inhibitors include rapamycin and rapamycin derivatives. Several other small molecule inhibitors of mTOR activity have also been identified. Use of more than one mTOR inhibitor in the combination therapy in accordance with embodiments of the inventions is also contemplated.

In some embodiments, the µ-opioid receptor antagonist may be a peripheral µ-opioid receptor antagonist. Peripherally-restricted µ-opioid receptor antagonists are generally heterocyclic amine compounds that also belong to several different classes of compounds. For example, one class is quaternary derivatives of morphinan, and in particular, quaternary derivatives of noroxymorphone. In one embodiment, the quaternary derivative of noroxymorphone is suitably, e.g., N-methylnaltrexone (or simply methylnaltrexone), N-methylnaloxone, N-methylnalorphine, N-diallylnormorphine, N-allyllevallorphan, or N-methylnalmefene. Another class of peripherally-restricted antagonists is N-substituted piperidines. In one embodiment, the N-piperidine is a piperidine-N-alkylcarbonylate, such as alvimopan. Other classes of compounds that may be of value in embodiments of the invention are quaternary derivatives of benzomorphans, quaternary derivatives of normorphanin and polymer conjugates of tertiary derivatives of morphanin, benzomorphan and normorphanin.

Embodiments of the invention also encompass administration of more than one µ-opioid receptor antagonist in therapeutic combinations. Antagonist combinations may include combinations of µ-antagonists and combinations of µ- and κ-antagonists, for example, a combination of methylnaltrexone and alvimopan, or a combination of naloxone and methylnaltrexone.

Other µ-opioid receptor antagonists that may be of use in the methods in accordance with embodiments of the invention may include tertiary derivatives of morphinan, and in particular, tertiary derivatives of noroxymorphone which include, e.g., naloxone.

BRIEF DESCRIPTION OF THE DRAWINGS

Embodiments of the invention may be better understood and appreciated by reference to the detailed description presented herein in conjunction with the accompanying drawings of which.

DETAILED DESCRIPTION

Figure 1:
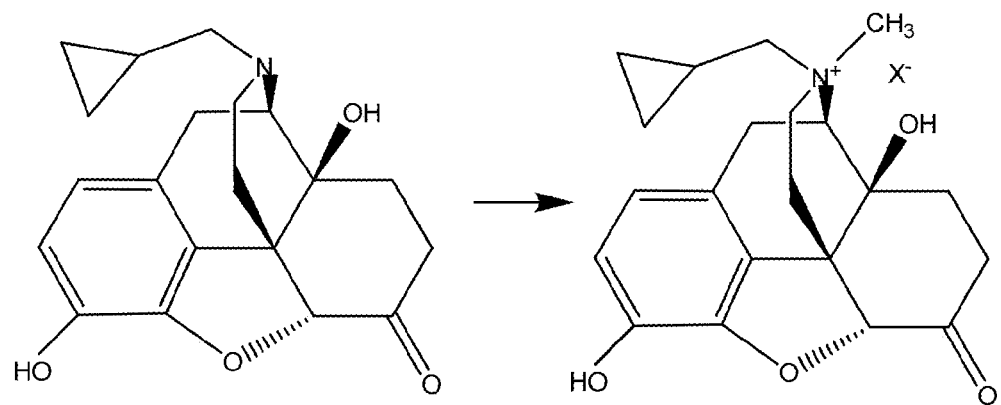
FIG. 1 depicts the chemical structures of naltrexone and methylnaltrexone, and the conversion reaction of naltrexone to methylnaltrexone.

According to the principles manifest in embodiments of the invention, pharmaceutical combinations and methods are provided utilizing a combination of mTOR inhibitors and μ-opioid receptor antagonists. Methods in accordance with embodiments of the invention include treating a disorder characterized by unwanted and undesired cell proliferation and migration, particularly unwanted and undesired endothelial cell proliferation and/or migration, by co-administering an mTOR inhibitor and a μ-opioid receptor antagonist. As explained in the Examples below, combinations of an mTOR inhibitor and a μ-opioid receptor antagonist, such as methylnaltrexone (MNTX), provide an unexpected synergy in reducing unwanted cell proliferation and migration, e.g., VEGF-induced proliferation and migration of endothelial cells.

Before explaining at least one embodiment of the invention, it is to be understood that the invention is not limited in its application to the details set forth in the following description and as exemplified by the Examples. Such description and Examples are not intended to limit the scope of the invention as set forth in the appended claims. The invention is capable of other embodiments or of being practiced or carried out in various ways. While the following detailed description and Examples describe the invention through reference to embodiments utilizing rapamycin, temsirolimus and methylnaltrexone as suitable drugs, it should be understood that other mTOR inhibitors and μ-opioid receptor antagonists may also be suitable for use in accordance with the principles of the invention.

Further, no admission is made that any reference, including any patent or patent document, cited in this specification constitutes prior art. In particular, it will be understood that, unless otherwise stated, reference to any document herein does not constitute an admission that any of these documents form part of the common general knowledge in the art in the United States or in any other country. Any discussion of the references states what their authors assert, and the applicant reserves the right to challenge the accuracy and pertinency of any of the documents cited herein.

Throughout this disclosure, various aspects of this invention may be presented in a range format. It should be understood that the description in range format is merely for convenience and brevity, and should not be construed as an inflexible limitation on the scope of the invention. Accordingly, as will be understood by one skilled in the art, for any and all purposes, particularly in terms of providing a written description, all ranges disclosed herein also encompass any and all possible subranges and combinations of subranges thereof, as well as all integral and fractional numerical values within that range. As an example, a range of 20% to 40% can be broken down into ranges of 20% to 32.5% and 32.5% to 40%, 20% to 27.5% and 27.5% to 40%, etc., all of which are understood to be expressly enumerated in this specification. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third, and upper third, etc.

As will also be understood by one skilled in the art, all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio. These are only examples of what is specifically intended. Further, the phrases "ranging/ranges between" a first indicate number and a second indicate number and "ranging/ranges from" a first indicate number "to" a second indicate number are used herein interchangeably.

Further, the use of "comprising," "including," "having," and variations thereof herein is meant to encompass the items listed thereafter and equivalents thereof as well as additional items, e.g., other steps and/or ingredients. These terms encompass the terms "consisting of" and "consisting essentially of." The use of "consisting essentially of" means that the composition or method may include additional ingredients and/or steps, but only if the additional ingredients and/or steps do not materially alter the basic and novel characteristics of the claimed composition or method.

Unless otherwise defined, all scientific and technical terms are used herein according to conventional usage and have the same meaning as commonly understood by one of ordinary skill in the art to which the invention belongs. However, as used herein, the following definitions may be useful in aiding the skilled practitioner in understanding the invention:

"Subject" refers to mammals, e.g., humans, mice, dogs, cats, rats.

"Alkyl" refers to a univalent aliphatic hydrocarbon group which is saturated and which may be straight, branched, or cyclic having from 1 to about 10 carbon atoms in the chain, and all combinations and subcombinations of chains therein. Exemplary alkyl groups include, but are not limited to, methyl, ethyl, n-propyl, isopropyl, butyl, isobutyl, sec-butyl, tert-butyl, pentyl, cyclopropyl, cyclobutyl, cyclopentyl, and cyclohexyl.

"Lower alkyl" refers to an alkyl group having 1 to about 6 carbon atoms.

"Alkenyl" refers to a univalent aliphatic hydrocarbon group containing at least one carbon-carbon double bond and having from 2 to about 10 carbon atoms in the chain, and all combinations and subcombinations of chains therein. Exemplary alkenyl groups include, but are not limited to, vinyl, propenyl, butynyl, pentenyl, hexenyl, and heptnyl.

"Alkynyl" refers to a univalent aliphatic hydrocarbon group containing at least one carbon-carbon triple bond and having from 2 to about 10 carbon atoms in the chain, and combinations and subcombinations of chains therein. Exemplary alkynyl groups include, but are not limited to, ethynyl, propynyl, butynyl, pentynyl, hexynyl, and heptynyl.

"Alkylene" refers to a divalent aliphatic hydrocarbon group having from 1 to about 6 carbon atoms, and all combinations and subcombinations of chains therein. The alkylene group may be straight, branched, or cyclic. There may be optionally inserted along the alkylene group one or more oxygen, sulfur, or optionally substituted nitrogen atoms, wherein the nitrogen substituent is an alkyl group as described previously.

"Alkenylene" refers to a divalent alkylene group containing at least one carbon-carbon double bond, which may be straight, branched, or cyclic. Exemplary alkenylene groups include, but are not limited to, ethenylene (—CH=CH—) and propenylene (—CH=CHCH$_2$—).

"Cycloalkyl" refers to a saturated monocyclic or bicyclic hydrocarbon ring having from about 3 to about 10 carbons, and all combinations and subcombinations of rings therein. The cycloalkyl group may be optionally substituted with one or more cycloalkyl-group substituents. Exemplary cycloalkyl groups include, but are not limited to, cyclopropyl, cyclobutyl, cyclopentyl, cyclohexyl, and cycloheptyl.

"Acyl" means an alkyl-CO group wherein alkyl is as previously described. Exemplary acyl groups include, but are not limited to, acetyl, propanoyl, 2-methylpropanoyl, butanoyl, and palmitoyl.

"Aryl" refers to an aromatic carbocyclic radical containing from about 6 to about 10 carbons, and all combinations and subcombinations of rings therein. The aryl group may be optionally substituted with one or two or more aryl group substituents. Exemplary aryl groups include, but are not limited to, phenyl and naphthyl.

"Aryl-substituted alkyl" refers to a linear alkyl group, preferably a lower alkyl group, substituted at a terminal carbon with an optionally substituted aryl group, preferably an optionally substituted phenyl ring. Exemplary aryl-substituted alkyl groups include, for example, phenylmethyl, phenylethyl, and 3(4-methylphenyl)propyl.

"Heterocyclic" refers to a monocyclic or multicyclic ring system carbocyclic radical containing from about 4 to about 10 members, and all combinations and subcombinations of rings therein, wherein one or more of the members of the ring is an element other than carbon, for example, nitrogen, oxygen, or sulfur. The heterocyclic group may be aromatic or nonaromatic. Exemplary heterocyclic groups include, for example, pyrrole and piperidine groups.

"Halo" refers to fluoro, chloro, bromo, or iodo.

"Co-administration" or "co-administering" is meant to refer to a combination therapy in which two or more agents are administered to a patient or subject by any administration route. Co-administration of agents may also be referred to as combination therapy or combination treatment. The agents may be in the same dosage formulation or separate formulations. For combination treatment with more than one active agent, where the active agents are in separate dosage formulations, the active agents can be administered concurrently, or they each can be administered at separately staggered times. The agents of a combination treatment may be administered simultaneously or sequentially (e.g., one agent may directly follow administration of the other or the agents may be given episodically, e.g., one can be given at one time followed by the other at a later time, e.g., within a week), as long as they are given in a manner sufficient to allow both agents to achieve effective concentrations in the body. The agents may also be administered by different routes, e.g., one agent may be administered intravenously while a second agent is administered intramuscularly, intravenously, or orally.

The terms "peripheral," or "peripherally-restricted" or "peripherally-acting" in reference to μ-opioid receptor antagonists, designate μ-opioid receptor antagonists that act primarily on physiological systems and components external to the central nervous system. In other words, they exhibit reduced or substantially no central nervous system (CNS) activity. For example, they do not readily cross the blood-brain barrier in an amount effective to inhibit the central effects of opioids, i.e., they do not effectively inhibit the analgesic effects of opioids when administered peripherally, that is, they do not reduce the analgesic effect of the opioids. The peripheral μ-opioid receptor antagonist compounds employed in the embodiments of the invention suitably exhibit less than about 5-15% of their pharmacological activity in the CNS, with about 0% (i.e., no) CNS activity, being most suitable. The non-centrally acting characteristic of a peripheral μ-opioid receptor antagonist is often related to charge, polarity, and/or size of the molecule or species. For example, peripherally-acting quaternary amine μ-opioid receptor antagonists as described herein are positively charged while the central-acting tertiary amine μ-opioid receptor antagonists are neutral molecules.

As used herein, the term "mTOR inhibitor" means a compound or ligand, or a pharmaceutically acceptable salt thereof, which inhibits cell replication by blocking the progression of the cell cycle from G1 to S by modulating mTOR activity or expression. The term includes the neutral tricyclic compound rapamycin (sirolimus) and other rapamycin compounds, including, e.g., rapamycin derivatives, rapamycin analogues, and other macrolide compounds as well as other structurally distinct small molecules, e.g. fused bicyclic compounds, that inhibit mTOR activity. These include compounds with a structural similarity to rapamycin, e.g., compounds with a similar macrocyclic structure that have been modified to enhance therapeutic benefit. mTOR inhibitors, including rapamycin derivatives, are described hereinafter.

The terms "treating" or "treatment" used herein include any means of control of a medical or pathological condition such as prevention, care, relief of the condition, attenuation, alleviation, a reduction of the condition or symptoms of the condition, and inhibition or arrest of progression of the condition.

As used herein, the term "side effect" is meant to refer to an effect other than the purpose or desired effect of a drug. Side effects may be beneficial or undesirable, i.e., adverse. In the instant case, undesirable effects often occur after the administration of an mTOR inhibitor. Such side effects include rash, asthenia, mucositis, anorexia, peripheral edema, hypertriglyceridemia, hypertension, hypercholesterolemia, increased creatinine, constipation, abdominal pain, diarrhea, headache, fever, urinary tract infection, anemia, nausea, arthralgia, pain, and thrombocytopenia.

The term "solvate" refers to a compound provided herein or a salt thereof, which further includes a stoichiometric or non-stoichiometric amount of solvent bound by non-covalent intermolecular forces. Where the solvent is water, the solvate is a hydrate.

As used herein, the term "potency" refers to the ability or capacity of an anticancer agent to treat cancer in a subject suffering from cancer. Potency may also be expressed as the dose of a drug required to produce a specific effect of a given intensity.

In certain embodiments, the term "unwanted" in connection with cell proliferation and migration, e.g., "unwanted proliferation" or "unwanted migration," is meant to refer to "abnormal or pathological or dysregulated or undesirable or inappropriate" proliferation, division, growth or migration of cells that is not part of normal cell turnover, metabolism, growth or propagation, and generally is occurring more rapidly or to a significantly greater extent than typically occurs in a normally functioning cell of the same type and does not serve normal function. Unwanted proliferation and unwanted migration is manifest in disorders that are hyperproliferative in nature and include, but are not limited to, cancers, such as melanoma, lung cancer, breast cancer, pancreatic cancer, prostate cancer, colon cancer or ovarian cancer, psoriasis, rheumatoid arthritis, epidermolytic by perkeratosis, restratosis, restenosis, endometriosis and abnormal wound healing.

In describing an optically active compound, the prefixes R and S are used to denote the absolute configuration of the molecule about its chiral center(s). The symbols (+) and (−) are used to denote the optical rotation of the compound, i.e., the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

In the following description of the methods of the invention, process steps are carried out at room temperature and atmospheric pressure unless otherwise specified.

In one aspect, an embodiment of the invention relates to methods of attenuating abnormal or undesirable cellular processes, for example, unwanted cell migration and/or proliferation, particularly unwanted endothelial cell migration and/or proliferation. Methods include administering one or more mTOR inhibitors and one or more µ-opioid receptor antagonists in a synergistically effective amount to cells of, e.g., a tissue or an organ of a patient or subject, particularly endothelial cells of a tissue or organ of a patient, to inhibit cell migration and/or proliferation, e.g., endothelial cell migration and/or proliferation.

µ-opioid receptor antagonists have been shown to inhibit unwanted proliferation and migration induced by opioids, endogenous or exogenous, and growth factors, such as VEGF, PDGF, S1P etc. Peripheral µ-opioid receptor antagonists, in particular, have shown a substantial efficacy in inhibiting opioid and growth factor-induced proliferation and migration of endothelial cells as disclosed in co-pending U.S. patent application Ser. No. 11/908,058. The peripheral µ-opioid receptor antagonist methylnaltrexone (MNTX) inhibits both opioid and growth factor-induced proliferation and migration in a concentration dependent manner. Furthermore, it has now been discovered that µ-opioid receptor antagonists, and the peripheral µ-opioid receptor antagonist MNTX in particular, inhibit agonist-induced endothelial cell (EC) proliferation and migration via inhibition of Akt. The agonists can be opioids, exogenous and/or endogenous, angiogenic factors (e.g., VEGF), and other proliferation and/or migration stimulating factors (e.g., PDGF, S1P, $S1P_3$ receptor, RhoA, etc).

µ-opioid receptor antagonists have also been shown to inhibit the ability of viruses to infect target cells. Peripheral µ-opioid receptor antagonists, in particular, have shown a substantial efficacy in inhibiting the viral entry of HIV and the expression of CCR5, the cell surface receptor of this virus, as disclosed in the co-pending U.S. patent application Ser. No. 10/163,482 incorporated herein by reference.

Embodiments of the invention demonstrate that µ-opioid receptor antagonists co-administered with mTOR inhibitors give rise to a significantly enhanced antiproliferative effect on cancerous cells, and thus provide an increased therapeutic effect, e.g., administering peripheral µ-opioid receptor antagonists to certain tumors can potentiate tumor response to mTOR inhibitors. As illustrated in the Examples below, a significantly increased antiproliferative and antimigratory effect is obtained with the above disclosed co-administered combinations utilizing lower concentrations of the mTOR inhibitor and the µ-opioid receptor antagonist compared to the treatment regimes in which the drugs are used alone. For example, co-administration of a µ-opioid receptor antagonist with an mTOR inhibitor in accordance with embodiments of the invention may reduce the dose of the mTOR inhibitor or increase potency or efficacy or both. Further, the co-administration of a µ-opioid receptor antagonist and an mTOR inhibitor in accordance with embodiments of the invention may also have prophylactic value.

There is also the potential to provide therapy wherein adverse side effects associated with mTOR inhibitors are considerably reduced compared to those normally observed with the mTOR inhibitors used alone in larger doses. These side effects include rash, asthenia, mucositis, anorexia, peripheral edema, hypertriglyceridemia, hypertension, hypercholesterolemia, increased creatinine, constipation, abdominal pain, diarrhea, headache, fever, urinary tract infection, anemia, nausea, arthralgia, pain, and thrombocytopenia. At least a subset of these adverse reactions are dose dependent. The potential for lower dosing is achieved utilizing embodiments in accordance with the invention.

There is the further potential to provide therapy wherein the high costs associated with mTOR inhibitor therapy are considerably reduced compared to those normally observed with the mTOR inhibitors used alone in larger doses. In addition, the co-administration of a μ-opioid receptor antagonist with an mTOR inhibitor can considerably increase the efficacy and potency of the mTOR inhibitor compared to that normally observed with the mTOR alone.

Methods embodying the principles manifest in embodiments of the invention include attenuating, e.g., inhibiting or reducing, unwanted cell proliferation and migration, particularly endothelial cell proliferation and migration, using mTOR inhibitors and μ-opioid receptor antagonists, including, but not limited to, those that are peripherally-restricted antagonists. According to one aspect of the invention, a method of treatment is provided that involves administering to a subject with a disorder characterized by unwanted migration or proliferation of endothelial cells, a synergistically effective amount of an mTOR inhibitor and a μ-opioid receptor antagonist. The treatment may inhibit one or both of migration and proliferation. In a further embodiment, the unwanted migration or proliferation is unwanted migration or proliferation of vascular endothelial cells that is treated with a synergistic amount of an mTOR inhibitor and a μ-opioid receptor antagonist. In another embodiment, the disorder characterized by unwanted migration or proliferation of vascular endothelial cells is unwanted angiogenesis. Thus, a method of treating unwanted angiogenesis is contemplated.

According to yet another aspect, methods of attenuating migration and/or proliferation of cells of a tumor or cancer are provided, which methods include contacting the cells with an antimigratory or antiproliferative amount of mTOR inhibitor and a μ-opioid receptor antagonist. In attenuating cell proliferation, a method of treating abnormal cell proliferation of cells that exhibit increased activation of the mTOR/Akt signaling pathway in a mammal is provided, which method includes administering to the mammal a synergistic therapeutically effective amount of an mTOR inhibitor and a μ-opioid receptor antagonist. Thus, a method of inhibiting mTOR/Akt pathway signaling in endothelial cells is also provided. Methods involve contacting the cells with a synergistically effective amount of an mTOR inhibitor and a μ-opioid receptor antagonist. A method of treating cancerous tissue in a subject is also provided, which method includes administering to the subject an amount of an mTOR inhibitor and a μ-opioid receptor antagonist sufficient to inhibit mTOR/Akt pathway-mediated effects in the cancerous tissue, as well as a method including contacting a tissue or a population of cells with a composition or combination including an amount of at least one of an mTOR inhibitor and at least one of a μ-opioid receptor antagonist under conditions effective to inhibit mTOR/Akt pathway-induced proliferation and migration.

In yet another embodiment, a method of treating abnormal proliferation of cells that express a growth factor receptor in a mammal is provided, which method includes administering to the mammal a synergistic therapeutically effective amount of an mTOR inhibitor and a μ-opioid receptor antagonist. In particular embodiments, the growth factor receptor is vascular endothelial growth factor receptor (VEGF-R), epidermal growth factor receptor (EGF-R) or insulin-like growth factor receptor (IGF-R). Thus, a method of inhibiting growth factor signaling in endothelial cells is also provided. In specific embodiments, the growth factor is VEGF, EGF or IGF. Methods involve contacting the cells with a synergistically effective amount of an mTOR inhibitor and a μ-opioid receptor antagonist. A method of treating cancerous tissue in a subject is also provided, which method includes administering to the subject an amount of an mTOR inhibitor and a μ-opioid receptor antagonist sufficient to inhibit growth factor-induced effects in the cancerous tissue, as well as a method including contacting a tissue or a population of endothelial cells with a composition or combination including an amount of at least one of an mTOR inhibitor and at least one of a μ-opioid receptor antagonist under conditions effective to inhibit growth factor-induced proliferation and migration. It is particularly contemplated that these effects in cancerous tissue are VEGF-, EGF- or IGF-induced.

In yet a further embodiment, a method of treating abnormal cell proliferation of cells that express a hormone receptor in a mammal is provided, which method includes administering to the mammal a synergistic therapeutically effective amount of an mTOR inhibitor and a μ-opioid receptor antagonist. In particular embodiments, the hormone receptor is estrogen receptor (ER), progesterone receptor (PR) or androgen receptor (AR). Thus, a method of inhibiting hormone signaling in endothelial cells is also provided. In specific embodiments, the hormone is estrogen, progesterone or androgen. Methods involve contacting the cells with a synergistically effective amount of an mTOR inhibitor and a μ-opioid receptor antagonist. A method of treating cancerous tissue in a subject is also provided, which method includes administering to the subject an amount of an mTOR inhibitor and a μ-opioid receptor antagonist sufficient to inhibit hormone-induced effects in the cancerous tissue, as well as a method including contacting a tissue or a population of endothelial cells with a composition or combination including an amount of at least one of an mTOR inhibitor and at least one of a μ-opioid receptor antagonist under conditions effective to inhibit hormone-induced proliferation and migration. It is particularly contemplated that these effects in cancerous tissue are estrogen-, progesterone- or androgen-induced.

In yet a further aspect, a method of treating a disorder or disease characterized by hyperproliferation of cells is provided, which method includes co-administering to a subject suffering thereof a synergistically effective amount of an mTOR inhibitor and a μ-opioid receptor antagonist. Yet another embodiment of the invention is a method of treating cancer in a subject in need thereof, comprising co-administering a synergistically effective amount of an mTOR inhibitor and a μ-opioid receptor antagonist. A further embodiment of the invention is a method of inhibiting growth of a tumor in a subject in need thereof, comprising co-administering a synergistically effective amount of an mTOR inhibitor and a μ-opioid receptor antagonist.

In a further aspect, a method of treating an autoimmune disease in a patient is provided, which method includes co-administering a synergistically effective amount of an mTOR inhibitor and a μ-opioid receptor antagonist. Autoimmune diseases of the invention include, but are not limited to, allergic encephalomyelitis, insulin-dependent diabetes mellitus, lupus, rheumatoid arthritis, multiple sclerosis, dermatomyositis, Grave's disease and adjuvant arthritis.

Yet another aspect of the invention provides a method of treating psoriasis in a patient, including co-administering a synergistically effective amount of an mTOR inhibitor and a μ-opioid receptor antagonist. In a particular embodiment, the synergistically effective amount of an mTOR inhibitor and a μ-opioid receptor antagonist is applied topically.

A further embodiment of the invention is a method of treating a neurodegenerative disease, which method includes the co-administration of a synergistically effective amount of an mTOR inhibitor and a μ-opioid receptor antagonist. In particular embodiments, the neurodegenerative disease is Parkinson's disease or multiple sclerosis.

Yet a further embodiment of the invention is a method of inhibiting CCR5-mediated viral entry into immune cells which includes the co-administration of a synergistically effective amount of an mTOR inhibitor and a μ-opioid receptor antagonist. The inhibition of CCR5-mediated HIV entry into immune cells is particularly contemplated. Further, a method of treating HIV/AIDS which includes co-administering to a subject suffering thereof a synergistically effective amount of an mTOR inhibitor and a μ-opioid receptor antagonist is provided.

In another aspect, nausea and emesis, induced by treatment of cancer with mTOR inhibitor, may be alleviated by co-administering a μ-opioid receptor antagonist, such as the peripheral μ-opioid receptor antagonist methylnaltrexone.

As noted above, mTOR inhibitors include compounds or ligands, or pharmaceutically acceptable salts thereof, which inhibit cell replication by blocking the progression of the cell cycle from G1 to S through the modulation of mTOR activity or expression. mTOR inhibitors that are currently available or under development, include temsirolimus (Torisel™; Wyeth), RAD001 (everolimus; Novartis), MK-8669 (deforolimus; Merck & Ariad pharma), TOP216 (Toptarget A/S), OSI-027 (OSI Pharma), TAFA93 (Isotechnika), nab-rapamycin (APP Phama) and tacrolimus (FK506; Astellas).

mTOR inhibitors include rapamycin and related compounds. Rapamycin is a macrolide produced by *Streptomyces*. Rapamycins are potent immunosuppressive agents and are used clinically to prevent rejection of transplanted organs. Rapamycin and related compounds are also currently under development as anti-cancer therapuetic agents. The rapamycins useful in embodiments of the invention include compounds that are chemically or biologically modified as derivatives of the rapamycin nucleus, while still retaining immunosuppressive or anti-cancer properties. Accordingly, rapamycins include rapamycin itself, and esters, ethers, carbamates, oximes, hydrazones, and hydroxylamines of rapamycin, as well as rapamycins in which functional groups on the rapamycin nucleus have been modified, for example through reduction or oxidation.

Specifically, the structure of rapamycin is given as formula (A) shown below:

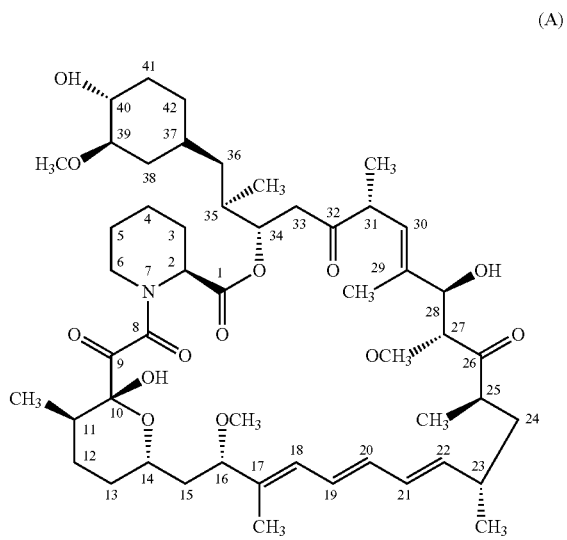

(A)

Many of the rapamycin derivatives disclosed above in current use or development have the basic rapamycin structure with substitutions at the C-40 position. If the substituent at position 40 is designated as R, then the following substitutions and corresponding compounds are: R=—OP(O)(Me)$_2$, AP23573 (International Patent Publication Nos. WO 98/02441 and WO 2001/14387); R=—OC(O)C(CH$_3$)(CH$_2$OH), temsirolimus (U.S. Pat. No. 5,362,718); R=—OCH$_2$CH$_2$OH, everolimus (U.S. Pat. No. 5,665,772); R=—OCH$_2$CH$_2$OEt, biolimus; R=-tetrazole, ABT-578 (International Patent Publication No. WO 99/15530). All patents and applications are hereby incorporated by reference.

Many other rapamycin derivatives include substitutions in the C-40 and/or C-16 and/or C-32 positions. Esters and ethers of rapamycin are described in the following patents, which are all hereby incorporated by reference: alkyl esters (U.S. Pat. No. 4,316,885); aminoalkyl esters (U.S. Pat. No. 4,650,803); fluorinated esters (U.S. Pat. No. 5,100,883); amide esters (U.S. Pat. No. 5,118,677); carbamate esters (U.S. Pat. Nos. 5,118,678; 5,411,967; 5,434,260; 5,480,988; 5,480,989; 5,489,680); silyl esters (U.S. Pat. No. 5,120,842); aminodiesters (U.S. Pat. No. 5,162,333); sulfonate and sulfate esters (U.S. Pat. No. 5,177,203); esters (U.S. Pat. No. 5,221,670); alkoxyesters (U.S. Pat. No. 5,233,036); O-aryl, -alkyl, -alkenyl, and -alkynyl ethers (U.S. Pat. No. 5,258,389); carbonate esters (U.S. Pat. No. 5,260,300); arylcarbonyl and alkoxycarbonyl carbamates (U.S. Pat. No. 5,262,423); carbamates (U.S. Pat. No. 5,302,584); hydroxyesters (U.S. Pat. No. 5,362,718); hindered esters (U.S. Pat. No. 5,385,908); heterocyclic esters (U.S. Pat. No. 5,385,909); gem-disubstituted esters (U.S. Pat. No. 5,385,910); amino alkanoic esters (U.S. Pat. No. 5,389,639); phosphorylcarbamate esters (U.S. Pat. No. 5,391,730); amidino carbamate esters (U.S. Pat. No. 5,463,048); hindered N-oxide esters (U.S. Pat. No. 5,491,231); biotin esters (U.S. Pat. No. 5,504,091); O-alkyl ethers (U.S. Pat. No. 5,665,772); and PEG esters of rapamycin (U.S. Pat. No. 5,780,462); 32-esters and ethers (U.S. Pat. No. 5,256,790). The preparation of these esters and ethers is disclosed in the patents listed above. All patents and applications are hereby incorporated by reference.

Also included are oximes, hydrazones, and hydroxylamines of rapamycin as disclosed in U.S. Pat. Nos. 5,373,014, 5,378,836, 5,023,264, and 5,563,145. The preparation of these oximes, hydrazones, and hydroxylamines is disclosed in the above-listed patents. The preparation of 40-oxorapamycin is disclosed in U.S. Pat. No. 5,023,263. All these patents are hereby incorporated by reference.

Other small molecule inhibitors of mTOR include fused bicyclic compounds (International Patent Publication Nos. WO 2007/61737, WO 2007/87395 and WO 2007/64993), heteroaromatic amines (International Patent Publication No. WO 2001/19828), pyrrolopyrimidine compounds (International Patent Publication No. WO 2005/47289), diphenyl-dihydro-indol-2-one derivatives (International Patent Publication No. WO 2005/97107), and trimethyl-dodeca-triene derivatives (US Patent Publication No. 2007/037887). All of these patents are hereby incorporated by reference.

The μ-opioid receptor antagonists in accordance with embodiments of the invention may include both centrally and peripherally acting μ-opioid receptor antagonists. However, it is contemplated that those antagonists of particular value are suitably the peripherally-restricted μ-opioid receptor antagonists.

μ-opioid receptor antagonists form a class of compounds that can vary in structure while maintaining their antagonist properties. These compounds include tertiary and quaternary morphinans, in particular noroxymorphone derivatives, N-substituted piperidines, and in particular, piperidine-N-alkylcarboxylates, and tertiary and quaternary benzomorphans, and tertiary and quaternary normorphinan derivatives, in particular 6-corboxy-normorphinan derivatives. Tertiary compound antagonists are fairly lipid soluble and cross the blood-brain barrier easily. Examples of μ-opioid receptor antagonists that cross the blood-brain barrier and are centrally (and peripherally) active include, e.g., naloxone (which is commercially available from Baxter Pharmaceutical Products, Inc.), and nalmefene (available, e.g., from DuPont Pharma). Peripherally-restricted antagonists, on the other hand, are typically charged, polar, and/or of high molecular weight, each of which impedes their crossing the blood-brain barrier. Methylnaltrexone is a quaternary derivative of the tertiary μ-opioid receptor antagonist, naltrexone. Addition of the methyl group to naltrexone forms a compound with greater polarity and lower lipid solubility. Thus, methylnaltrexone does not cross the blood-brain barrier and has the potential for blocking the undesired adverse effects which are typically mediated by peripherally located receptors.

A peripheral μ-opioid receptor antagonist for use in embodiments of the invention may be a compound which is a quaternary morphinan derivative, and in particular, a quaternary noroxymorphone of formula (I):

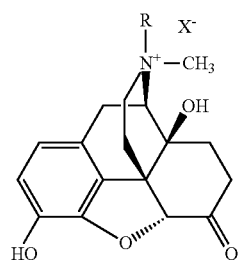

(I)

a single enantiomer, a mixture of enantiomers, an individual diastereomer, or a mixture of diastereomers thereof; or a pharmaceutically acceptable salt, solvate, or prodrug thereof, wherein R is alkyl, alkenyl, alkynyl, aryl, cycloalkyl-substituted alkyl, or arylsubstituted alkyl, and X⁻ is an anion, especially a chloride, bromide, iodide, carbonate or methylsulfate anion. The noroxymorphone derivatives of formula (I) can be prepared, for example, according to the procedure in U.S. Pat. No. 4,176,186, which is incorporated herein by reference; see also, U.S. Pat. Nos. 4,719,215; 4,861,781; 5,102,887; 5,972,954; and 6,274,591; U.S. Patent Application Nos. 2002/0028825 and 2003/0022909; and PCT publication Nos. WO 99/22737 and WO 98/25613, all of which are hereby incorporated by reference.

A compound of formula (I) of particular value is N-methylnaltrexone (or simply methylnaltrexone), wherein R is cyclopropylmethyl as represented in formula (II):

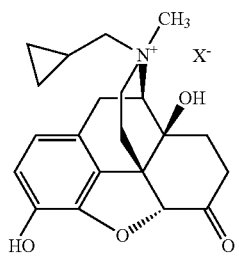

(II)

a single enantiomer, a mixture of enantiomers, an individual diastereomer, or a mixture of diastereomers thereof; or a pharmaceutically acceptable salt, solvate, or prodrug thereof, wherein X⁻ is as described above. Methylnaltrexone is a quaternary derivative of the μ-opioid receptor antagonist naltrexone. Methylnaltrexone exists as a salt (e.g., N-methylnaltrexone bromide) and the terms "methylnaltrexone" or "MNTX", as used herein, therefore embrace such salts. "Methylnaltrexone" or "MNTX" thus specifically includes, but is not limited to, bromide salts, chloride salts, iodide salts, carbonate salts, and methylsulfate salts of methylnaltrexone. Names used for the bromide salt of MNTX in the literature, for example, include: methylnaltrexone bromide; N-methylnaltrexone bromide; naltrexone methobromide; naltrexone methyl bromide; SC-37359; MRZ-2663-BR; and N-cyclopropylmethylnoroxy-morphine-methobromide.

Thus, herein, the term "methylnaltrexone" should be understood to mean any appropriate form of methylnaltrexone, e.g., N-methylnaltrexone or any pharmaceutically acceptable salt thereof, any prodrug thereof, enantiomers thereof, epimers thereof (the latter of which are described hereinafter).

The compounds of formulas (I) and (II), e.g., methylnaltrexone, may have chiral centers and can, therefore, occur as stereochemical isomers by virtue of the substituent placement on those chiral centers. Such stereochemical isomers, e.g., enantiomers, diastereomers, are within the scope of the compounds contemplated for use in embodiments of the invention. In the compositions and methods of embodiments of the invention, compounds employed may be individual stereoisomers, as well as mixtures of stereoisomers, e.g., mixtures of enantiomers, mixtures of diastereomers. In certain aspects, methods are provided that utilize compounds which are substantially pure stereoisomers. All tautomers are also intended to be encompassed within the compositions of the invention.

For example, the R and S configurations of methynaltrexone are known, and in some embodiments, isolated R—N isomers of methylnaltrexone may be utilized in formulations and methods. As used herein, the designation of "R—N-isomer" of methylnaltrexone refers to such compounds in the (R) configuration with respect to the nitrogen. Isolated isomer compounds include, but are not limited to, R—N isomer methylnaltrexone compounds described in U.S. patent application Ser. No. 11/441,395, and Patent Cooperation Treaty published application WO2006/127899, incorporated herein by reference. In some embodiments, the active compound is an R—N isomer methylnaltrexone, or a salt thereof. The R—N isomer of methylnaltrexone, described in U.S. Ser. No. 11/441,395, is an opioid antagonist.

In some embodiments, isolated S—N isomers of methylnaltrexone may be utilized in formulations and methods. As used herein, the designation of "S—N-isomer" of methylnaltrexone refers to such compounds in the (S) configuration with respect to the nitrogen. Isolated isomer compounds include, but are not limited to, S—N isomer of methylnaltrexone compounds described in U.S. patent application Ser. No. 11/441,452, and Patent Cooperation Treaty published application WO2006/127898, incorporated herein by reference. In some embodiments, the active compound is an S—N isomer methylnaltrexone, or a salt thereof. The S—N isomer of methylnaltrexone, described in U.S. Ser. No. 11/441,452, is an opioid agonist.

In certain embodiments, the methylnaltrexone utilized in formulations or dosage preparations described herein is a mixture of stereoisomers characterized in that it has an overall opioid antagonistic effect. For example, the methylnaltrexone may be a mixture of R—N and S—N methylnaltrexone such that a mixture itself acts as an antagonist and would be useful for methods of use described herein for opioid antagonists. In certain embodiments, R—N methylnaltrexone is used which is substantially free of S—N methylnaltrexone.

In certain embodiments of the invention, at least about 99.6%, 99.7%, 99.8%, 99.85%, 99.9%, or 99.95% of methylnaltrexone is in the (R) configuration with respect to nitrogen. Methods for determining the amount of (R)—N-isomer, present in a sample as compared to the amount of (S)—N-isomer present in that same sample, are described in detail in WO2006/127899, the entirety of which is hereby incorporated herein by reference. In other embodiments, methylnaltrexone contains 0.15%, 0.10%, or less (S)—N-isomer.

It will be understood by those skilled in the art that, where reference is made herein to amounts of methylnaltrexone utilized in formulations, dosage preparations, or methods, those amounts may refer to total amount of methylnaltrexone (or salt thereof), or to amount of relevant active form of methylnaltrexone for a particular purpose (e.g., opioid antagonism), whether or not other forms of methylnaltrexone are also present. Furthermore, as indicated herein, dosages or amounts are sometimes defined with reference to a particular form of methylnaltrexone (e.g., N-methylnaltrexone bromide). Where a different form or salt of methylnaltrexone is used, those of ordinary skill in the art will appreciate that such dosages or amounts may be adjusted to a dose or amount that provides an equivalent amount of active methylnaltrexone.

Methylnaltrexone is commercially available from, e.g., Mallinckrodt Pharmaceuticals, St. Louis, Mo. Methylnaltrexone is provided as a white crystalline powder, freely soluble in water, typically as the bromide salt. The compound as provided is 99.4% pure by reverse phase HPLC, and contains less than 0.011% unquaternized naltrexone by the same method. Methylnaltrexone can be prepared as a sterile solution at a concentration of, e.g., about 5 mg/mL.

Other peripheral μ-opioid receptor antagonists may include N-substituted piperidines, and in particular, piperidine-N-alkylcarboxylates as represented by formula (III):

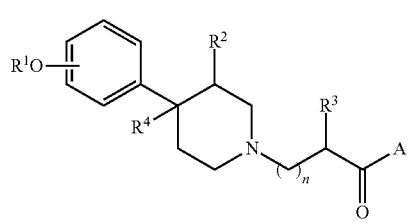

(III)

wherein $R^1$ is hydrogen or alkyl; $R^2$ is hydrogen, alkyl, or alkenyl; $R^3$ is hydrogen, alkyl, alkenyl, aryl, cycloalkyl, cycloalkenyl, cycloalkyl-substituted alkyl, cycloalkenyl-substituted alkyl, or aryl-substituted alkyl; $R^4$ is hydrogen, alkyl, or alkenyl; A is $OR^5$ or $NR^6R^7$; wherein $R^5$ is hydrogen, alkyl, alkenyl, cycloalkyl, cycloalkenyl, cycloalkyl-substituted alkyl, cycloalkenyl-substituted alkyl, or aryl-substituted alkyl; $R^6$ is hydrogen or alkyl; $R^7$ is hydrogen, alkyl, alkenyl, aryl, cycloalkyl, cycloalkenyl, cycloalkyl-substituted alkyl, cycloalkenyl-substituted alkyl or aryl-substituted alkyl, or alkylene-substituted B or together with the nitrogen atom to which they are attached, $R^6$ and $R^7$ form a heterocyclic ring selected from pyrrole and piperidine; B is

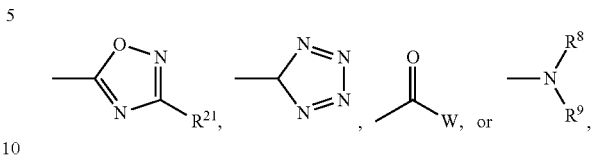

wherein $R^8$ is hydrogen or alkyl; $R^9$ is hydrogen, alkyl, alkenyl, aryl, cycloalkyl, cycloalkenyl, cycloalkyl-substituted alkyl, cycloalkenyl-substituted alkyl or aryl-substituted alkyl or together with the nitrogen atom to which they are attached, $R^8$ and $R^9$ form a heterocyclic ring selected from pyrrole and piperidine; W is $OR^{10}$, $NR^{11}R^{12}$, or OE; wherein $R^{19}$ is hydrogen, alkyl, alkenyl, cycloalkyl, cycloalkenyl, cycloalkyl-substituted alkyl, cycloalkenyl-substituted alkenyl, or aryl-substituted alkyl; $R^{11}$ is hydrogen or alkyl; $R^{12}$ is hydrogen, alkyl, alkenyl, aryl, cycloalkyl, cycloalkenyl, cycloalkyl-substituted alkyl, cycloalkenyl-substituted alkyl, aryl-substituted alkyl, or alkylene-substituted C(=O)Y or, together with the nitrogen atom to which they are attached, $R^{11}$ and $R^{12}$ form a heterocyclic ring selected from pyrrole and piperidine;

E is

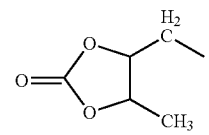

alkylene-substituted (C=O)D, or —$R^{13}$OC(=O)$R^{14}$; wherein $R^{13}$ is alkyl-substituted alkylene; $R^{14}$ is alkyl; D is $OR^{15}$ or $NR^{16}R^{17}$; wherein $R^{15}$ is hydrogen, alkyl, alkenyl, cycloalkyl, cycloalkenyl, cycloalkyl-substituted alkyl, cycloalkenyl substituted alkyl, or aryl-substituted alkyl; $R^{16}$ is hydrogen, alkyl, alkenyl, aryl, aryl-substituted alkyl, cycloalkyl, cycloalkenyl, cycloalkyl substituted alkyl, or cycloalkenyl-substituted alkyl; $R^{17}$ is hydrogen or alkyl or, together with the nitrogen atom to which they are attached, $R^{16}$ and $R^{17}$ form a heterocyclic ring selected from the group consisting of pyrrole or piperidine;

Y is $OR^{18}$ or $NR^{19}R^{20}$; wherein $R^{18}$ is hydrogen, alkyl, alkenyl, cycloalkyl, cycloalkenyl, cycloalkyl-substituted alkyl, cycloalkenyl-substituted alkyl, or aryl-substituted alkyl; $R^{19}$ is hydrogen or alkyl; $R^{20}$ is hydrogen, alkyl, alkenyl, aryl, cycloalkyl, cycloalkenyl, cycloalkylsubstituted alkyl, cycloalkenyl-substituted alkyl, or aryl-substituted alkyl or, together with the nitrogen atom to which they are attached, $R^{19}$ and $R^{20}$ form a heterocyclic ring selected from pyrrole and piperidine; $R^{21}$ is hydrogen or alkyl; and n is 0 to 4.

Particular piperidine-N-alkylcarbonylates which may be of value are N-alkylamino-3,4,4 substituted piperidines, such as alvimopan represented below as formula (IV):

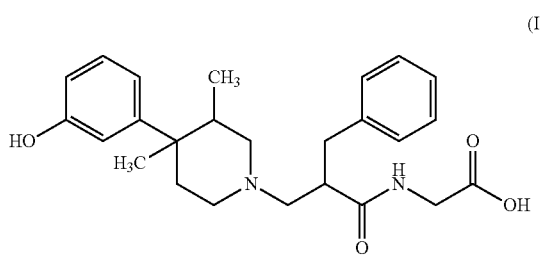

(IV)

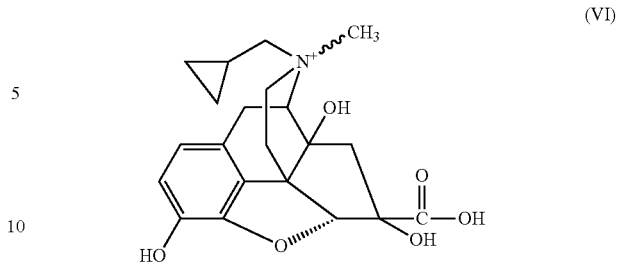

(VI)

N-substituted piperidines may be prepared as disclosed in U.S. Pat. Nos. 5,270,328; 6,451,806; 6,469,030, all of which are hereby incorporated by reference. Alvimopan is available from Adolor Corp., Exton, Pa. Such compounds have moderately high molecular weights, a zwitterion form, and a polarity that prevent penetration of the blood-brain barrier.

Still other peripheral μ-opioid receptor antagonist compounds may include quaternary benzomorphan compounds. Quaternary benzomorphan compounds, which may be employed in embodiments of the invention, have the following formula (V):

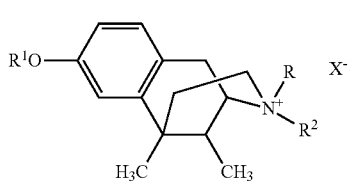

(V)

wherein $R^1$ is hydrogen, acyl, or acetoxy; and $R^2$ is alkyl or alkenyl; R is alkyl, alkenyl, or alkynyl and $X^-$ is an anion, especially a chloride, bromide, iodide, or methylsulfate anion.

Specific quaternary derivatives of benzomorphan compounds that may be employed in embodiments of the invention include the following compounds of formula (V): 2'-hydroxy-5,9-dimethyl-2,2-diallyl-6,7-benzomorphanium-bromide; 2'-hydroxy-5,9-dimethyl-2-n-propyl-2-allyl-6,7-benzomorphanium-bromide; 2'-hydroxy-5,9-dimethyl-2-n-propyl-2-propargyl-6,7-benzomorphanium-bromide; and 2'-acetoxy-5,9-dimethyl-2-n-propyl-2-allyl-6,7-benzomorphanium-bromide.

Other quaternary benzomorphan compounds that may be employed in embodiments of the invention are described, for example, in U.S. Pat. No. 3,723,440, the entire disclosure of which is incorporated herein by reference.

Other peripheral opioid antagonists may include 6-carboxy-normorphinan derivatives, particularly N-methyl-C-normorphinan derivatives, as described in U.S. Pat. No. 7,501,434, entitled "6-Carboxy-Normorphinan Derivatives, Synthesis and Uses Thereof," incorporated in its entirety herein by reference and including the compound having the following formula (VI):

Peripheral opioid antagonists may also include polymer conjugates of opioid antagonists, as described in U.S. patent application Ser. No. 11/332,964, hereby incorporated by reference. Specific polymer conjugates include PEGylated naloxone and naltrexone.

Embodiments of the invention also encompass administration of more than one μ-opioid receptor, including combinations of μ-opioid receptor antagonists and combinations of mu and kappa antagonists, for example, a combination of methylnaltrexone and alvimopan.

The compounds employed in embodiments of the invention may exist in prodrug form. As used herein, "prodrug" is intended to include any covalently bonded carriers which release the active parent drug or compounds that are metabolized in vivo to an active drug or other compounds employed in embodiments of the invention in vivo when such prodrug is administered to a mammalian subject. Since prodrugs are known to enhance numerous desirable qualities of pharmaceuticals (e.g., solubility, bioavailability, manufacturing, etc.), the compounds employed in some embodiments of the invention may, if desired, be delivered in prodrug form. Thus, embodiments of the invention contemplate methods of delivering prodrugs. Prodrugs of the compounds employed in embodiments of the invention may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively. Other examples include, but are not limited to, acetate, formate, and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

As noted, the compounds employed in embodiments of the invention may be prepared in a number of ways well known to those skilled in the art. All preparations disclosed in embodiments of the invention are contemplated to be practiced on any scale, including milligram, gram, multigram, kilogram, multikilogram, or commercial pharmaceutical scale.

As noted above for methylnaltrexone, compounds employed in embodiments of the invention may contain one or more asymmetrically-substituted carbon atoms, and may be isolated in optically active or racemic form. Thus, all chiral, diastereomeric, racemic form, epimeric form, and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic form, normal, reverse-phase, and chiral chromatography, preferential salt formation, recrystallization, and the like, or by chiral synthesis either from chiral starting materials or by deliberate synthesis of target chiral centers.

Methods of embodiments of the invention, generally speaking, may be practiced using any mode of administration that is medically acceptable, e.g., any mode that produces effective levels of the active compounds without causing clinically unacceptable adverse effects. Such modes of administration include oral, rectal, topical (as by powder, ointment, drops, transdermal patch, or iontophoretic device), transdermal, sublingual, intramuscular, infusion, intravenous, pulmonary, intramuscular, intracavity, as an aerosol, aural (e.g., via eardrops), intranasal, inhalation, intraocular, or subcutaneous.

Additionally, the compounds in accordance with embodiments of the invention may be administered as an enterically coated tablet or capsule. In some embodiments, the μ-opioid receptor antagonist is administered by a slow infusion method or by a time-release or controlled-release method or as a lyophilized powder.

Further, the compounds in accordance with embodiments of the invention may be administered topically. Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

When administered, the compounds of embodiments of the invention are given in pharmaceutically acceptable amounts and in pharmaceutically acceptable compositions or preparations. Such preparations may routinely contain salts, buffering agents, preservatives, and optionally other therapeutic ingredients.

When used in medicine, pharmaceutically acceptable salts of the compounds in accordance with embodiments of the invention may be used, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulfuric, nitric, phosphoric, maleic, acetic, salicylic, p-toluenesulfonic, tartaric, citric, methanesulfonic, formic, succinic, naphthalene-2-sulfonic, pamoic, 3-hydroxy-2-naphthalenecarboxylic, and benzene sulfonic.

Buffering agents and preservatives may also be included in preparations in accordance with embodiments of the invention. Suitable buffering agents may include, but are not limited to, acetic acid and salts thereof (1-2% w/v); citric acid and salts thereof (1-3% w/v); boric acid and salts thereof (0.5-2.5% w/v); and phosphoric acid and salts thereof (0.8-2% w/v). Suitable preservatives may include, but are not limited to, benzalkonium chloride (0.003-0.03% w/v); chlorobutanol (0.3-0.9% w/v); parabens (0.01-0.25% w/v); and thimerosal (0.004-0.02% w/v).

For ease of administration, a pharmaceutical composition in accordance with embodiments of the invention may also contain one or more pharmaceutically acceptable excipients, such as lubricants, diluents, binders, carriers, and disintegrants. Other auxiliary agents may include, e.g., stabilizers, wetting agents, emulsifiers, salts for influencing osmotic pressure, coloring, flavoring, and/or aromatic active compounds.

A pharmaceutically acceptable carrier or excipient refers to a non-toxic solid, semi-solid or liquid filler, diluent, encapsulating material, or formulation auxiliary of any type. For example, suitable pharmaceutically acceptable carriers, diluents, solvents, or vehicles include, but are not limited to, water, salt (buffer) solutions, alcohols, gum arabic, mineral and vegetable oils, benzyl alcohols, polyethylene glycols, gelatin, carbohydrates such as lactose, amylose or starch, magnesium stearate, talc, silicic acid, viscous paraffin, vegetable oils, fatty acid monoglycerides and diglycerides, pentaerythritol fatty acid esters, hydroxyl methylcellulose, polyvinyl pyrrolidone, etc. Proper fluidity may be maintained, for example, by the use of coating materials such as lecithin or by the maintenance of the required particle size in the case of dispersions and by the use of surfactants. Prevention of the action of microorganisms may be ensured by the inclusion of various antimicrobial, e.g., antibacterial and antifungal, agents such as paraben, chlorobutanol, phenol, sorbic acid and the like.

If a pharmaceutically acceptable solid carrier is used, the dosage form of the compounds suitable for use in embodiments of the invention may be tablets, capsules, powders, suppositories, or lozenges. If a liquid carrier is used, soft gelatin capsules, transdermal patches, aerosol sprays, topical cream, syrups or liquid suspensions, emulsions, or solutions may be the dosage form.

For parenteral application, particularly suitable are injectable, sterile solutions, preferably nonaqueous or aqueous solutions, as well as dispersions, suspensions, emulsions, or implants, including suppositories. Ampoules are often convenient unit dosages. Injectable depot-form may also be suitable and may be made by forming microencapsule matrices of the drug in biodegradable polymers such as polylactide-polyglycolide, poly(orthoesters), and poly(anhydrides). Depending upon the ratio of drug to polymer and the nature of the particular polymer employed, the rate of drug release can be controlled.

For enteral application, particularly suitable are tablets, dragees, liquids, drops, suppositories, or capsules such as soft gelatin capsules. A syrup, elixir, or the like can be used wherein a sweetened vehicle is employed.

As noted, other pharmaceutical delivery systems may include time-release, delayed-release, or sustained-release delivery systems. Such systems can avoid repeated administrations of the compounds of the invention, increasing convenience to the patient and the physician and maintaining sustained plasma levels of compounds. Many types of controlled-release delivery systems are available and known to those of ordinary skill in the art.

For example, compounds of embodiments of the invention may be combined with pharmaceutically acceptable sustained-release matrices, such as biodegradable polymers, to form therapeutic compositions. A sustained-release matrix, as used herein, is a matrix made of materials, usually polymers, which are degradable by enzymatic or acid-base hydrolysis or by dissolution. Once inserted into the body, the matrix is acted upon by enzymes and body fluids. A sustained-release matrix may be desirably chosen from biocompatible materials such as liposomes; polymer-based system such as polylactides (polylactic acid), polyglycolide (polymer of glycolic acid), polylactide co-glycolide (copolymers of lactic acid and glycolic acid), polyanhydrides, poly(ortho)esters, polysaccharides, polyamino acids, hyaluronic acid, collagen, chondroitin sulfate, polynucleotides, polyvinyl propylene, polyvinyl pyrrolidone, and silicone; nonpolymer system such as carboxylic acids, fatty acids, phospholipids, amino acids, and lipids such as sterols;

hydrogel release systems; silastic systems; peptide-based systems; implants and the like. Specific examples include, but are not limited to: (a) an erosional system in which the polysaccharide is contained in a form within a matrix, found in U.S. Pat. Nos. 4,452,775, 4,675,189, and 5,736,152 (herein incorporated by reference in their entireties), and (b) a diffusional system in which an active component permeates at a controlled rate from a polymer such as described in U.S. Pat. Nos. 3,854,480, 5,133,974, and 5,407,686 (herein incorporated by reference in their entireties). In addition, a pump-based hard-wired delivery system can be used, some of which are adapted for implantation. Suitable enteric coatings are described in PCT publication No. WO 98/25613 and U.S. Pat. No. 6,274,591, both incorporated herein by reference. Sustained- or controlled-release compositions may also be formulated as those wherein the active compound is protected with differentially degradable coatings, such as by microencapsulation, multiple coatings, etc.

Respecting methylnaltrexone specifically, aqueous formulations may include a chelating agent, a buffering agent, an anti-oxidant and, optionally, an isotonicity agent, preferably pH adjusted to between 3.0 and 3.5. Formulations that are stable to autoclaving and long term storage are described in U.S. patent application Ser. No. 10/821,811, published as 2004/0266806, entitled "Pharmaceutical Formulation," the disclosure of which is incorporated herein by reference. Formulations of methylnaltrexone with increased shelf-life are also described in International Patent Publication No. WO 2008/19115, entitled "Formulations for Parenteral Delivery of Compounds and Uses Thereof," hereby incorporated by reference. Lyophilized formulations of methylnaltrexone are described in U.S. patent application Ser. No. 11/899,724 and formulations comprising particles containing methylnaltrexone are described in U.S. Pat. No. 6,419,959, which is incorporated herein by reference. Formulations suitable for transdermal delivery of methylnaltrexone are described in International Patent Publication No. 2007/41544, hereby incorporated by reference.

Compounds in accordance with embodiments of the invention, mTOR inhibitors and µ-opioid receptor antagonists, are provided in combination in a synergistic antiproliferative and antimigratory effective amount. It will be understood, however, that the total dosage of the compounds and compositions of the invention will be decided by the attending physician within the scope of sound medical judgment. The specific therapeutically-effective dose level for any particular patient will depend upon a variety of factors including the disorder being treated and the severity of the disorder; activity of the specific compound employed; the specific composition employed; the age, body weight, general health, sex, and diet of the patient; the time of administration; the route of administration; the rate of excretion of the specific compound employed; the duration of the treatment; drugs used in combination or coincidental with the specific compound employed and like factors well known in the medical arts. For example, one technique is to start doses of the compound at levels lower than those required to achieve the desired therapeutic effect and to gradually increase the dosage until the desired effect is achieved.

If desired, an effective daily dose may be divided into multiple doses for purposes of administration. Consequently, single dose compositions may contain such amounts or submultiples thereof to make up a daily dose. As noted, those of ordinary skill in the art can readily optimize effective doses and co-administration regimens (as described herein) as determined by good medical practice and the clinical condition of the individual patient.

Generally, oral doses of the µ-opioid receptor antagonists, particularly peripheral antagonists, will range from about 0.01 to about 80 mg/kg body weight per day. It is expected that oral doses in the range from 1 to 20 mg/kg body weight will yield the desired results. Generally, parenteral administration, including intravenous and subcutaneous administration, will range from about 0.001 to 5 mg/kg body weight. It is expected that doses ranging from 0.05 to 0.5 mg/kg body weight will yield the desired results. Dosages may be adjusted appropriately to achieve desired drug levels, local or systemic, depending on the mode of administration. For example, it is expected that the dosage for oral administration of the µ-opioid receptor antagonists in an enterically coated formulation would be from 10 to 30% of the non-coated oral dose. In the event that the response in a patient is insufficient with such doses, even higher doses (or effectively higher than 30% dosage by a different, more localized delivery route) may be employed to the extent that the patient tolerance permits. Multiple doses per day are contemplated to achieve appropriate systemic levels of compounds. Appropriate system levels can be determined by, for example, measurement of the patient's plasma level of the drug using routine HPLC methods known to those skilled in the art.

In embodiments of the invention, an mTOR inhibitor compound may be administered as appropriate, e.g. in dosages which are known for compounds of embodiments of the invention, by any administration route, for example, enterally, (e.g., orally), or parenterally or topically. A variety of oral and parental dosage forms are known for the mTOR inhibitors. Oral daily dosages may range from 0.1 mg to 25 mg, in the form, e.g., of dispersible tablets. A weekly dosage may include up to 70 mg, depending on the disease being treated. For parental administration, including intravenous administration, an initial intravenous dosage will be between about 0.1 and 100 mg/m$^2$ when administered on a daily dosage regimen (daily for five days, every two to three weeks), and more suitably, between 0.1 and 1000 mg/m$^2$ when administered on a once weekly dosage regimen. For example, everolimus may be administered orally, in daily dosages from 0.1 mg up to 25 mg or 0.1 mg to 15 mg, including 0.1 mg, 0.25 mg, 0.5 mg, 0.75 mg, 1 mg, 2.5 mg, 5 mg, or 10 mg, e.g., in the form of dispersible tablets or in the form of a solid dispersion, depending on the disease being treated. Everolimus may be administered in a weekly dosage that may include up to 70 mg, such as 10 to 70 mg, or 30 to 50 mg, depending on the disease being treated. For further example, tacrolimus (Protopic) may be administered as an ointment of 0.03% to 0.1% (w/w) in an ointment base. Other mTOR inhibitors may be administered analogously, e.g. in similar dosage ranges.

In illustrated embodiments of the invention, the µ-opioid receptor antagonists are co-administered with an mTOR inhibitor. In other words, the co-administration of the µ-opioid receptor antagonist compound with an mTOR inhibitor, is suitably considered a pharmaceutical combination which contains an µ-opioid receptor antagonist and an mTOR inhibitor, the combination being adapted for the administration of the peripheral µ-opioid receptor antagonist on a daily or intermittent basis, and the administration of the mTOR inhibitor on a daily or intermittent basis. Thus, the µ-opioid receptor antagonists may be administered prior to, concomitant with, or after administration of the mTOR inhibitor. In an exemplary regimen, patients will receive a 30-minute intravenous infusion of the mTOR inhibitor, followed immediately or preceded by administration of the μ-opioid receptor antagonists. After one or more treatment cycles, the dosages can be adjusted upwards or downwards depending on the results obtained and any side effects observed. In an illustrated embodiment, particularly suitable is administration of the μ-opioid receptor antagonist prior to administration of the mTOR inhibitor.

Co-administrable agents in accordance with embodiments of the invention also may be formulated as an admixture, as, for example, in a single formulation or single tablet. These formulations may be parenteral or oral, such as the formulations described, e.g., in U.S. Pat. Nos. 6,277,384; 6,261,599; 5,958,452 and PCT Publication No. WO 98/25613, each hereby incorporated by reference.

Methods in accordance with embodiments of the invention can be used alone or in conjunction with other treatments to control the growth or migration of endothelial cells in connection with the various conditions described above. The mTOR inhibitor and the peripheral μ-opioid receptor antagonist may be co-administered with another therapeutic agent that is not an opioid or μ-opioid receptor antagonist or an mTOR inhibitor. Such suitable therapeutic agents include other anticancer agents.

Embodiments of the invention also include the treatment of cancer. The types of cancer that may be treated is limited only the involvement of mTOR. Thus, it is contemplated that a wide variety of tumors may be treated using these therapies, including cancers of the brain, lung, liver, spleen, kidney, lymph node, pancreas, small intestine, blood cells, colon, stomach, breast, endometrium, prostate, testicle, ovary, skin, head and neck, esophagus, bone marrow, blood or other tissue.

In many contexts, it is not necessary that the tumor cell be killed or induced to undergo normal cell death or "apoptosis." Rather, to accomplish a meaningful treatment, all that is required is that the tumor growth be slowed to some degree. It may be that the tumor growth is completely blocked, however, or that some tumor regression is achieved. Clinical terminology such as "remission" and "reduction of tumor" burden also are contemplated given their normal usage.

Embodiments of the invention are further explained by the following examples, which should not be construed by way of limiting the scope of the present invention.

EXAMPLES

Example 1

Inhibition of VEGF-Induced Akt Activation

Figure 2:
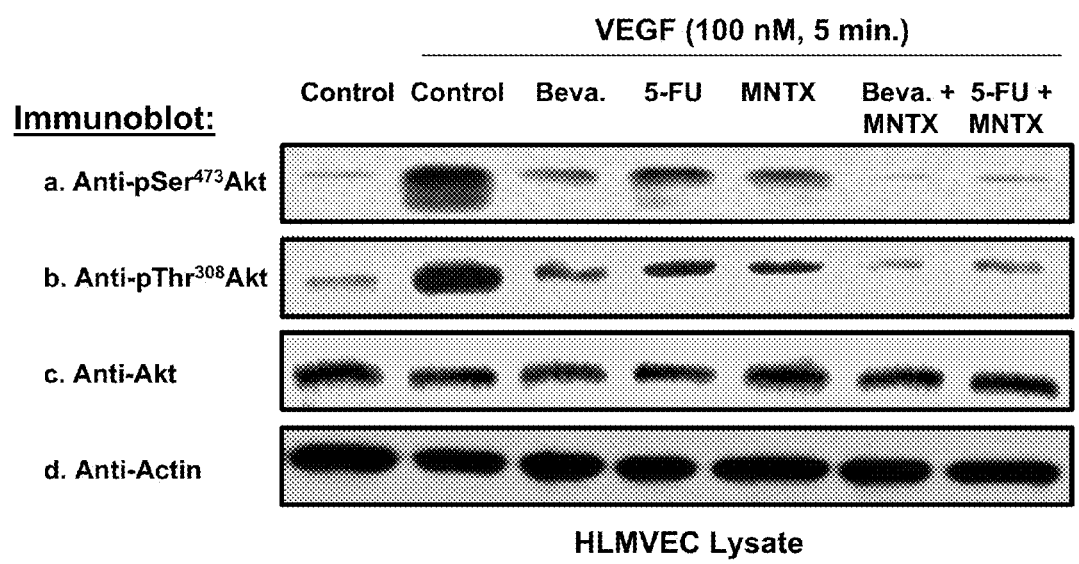
FIG. 2 is an immunoblot demonstrating VEGF-induced phosphorylation (activation) of Akt at serine$^{473}$ and threonine$^{308}$ using anti-phospho-serine$^{473}$-Akt, anti-phospho-threonine$^{308}$-Akt and anti-Akt specific antibodies in human endothelial cells in the presence of bevacizumab, 5-FU, methylnaltrexone, a combination of bevacizumab and methylnaltrexone and a combination of 5-FU and methylnaltrexone.
Figure 3:
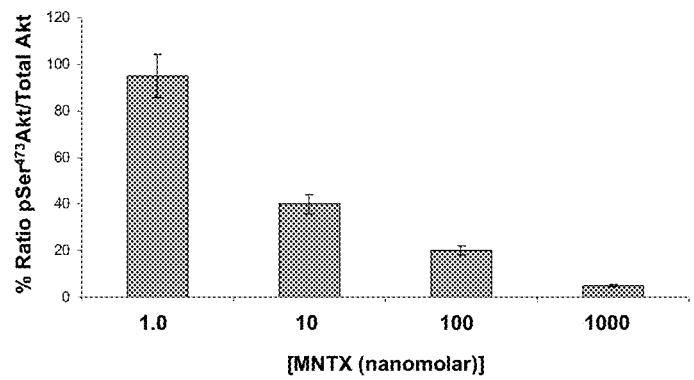
FIG. 3 is a graph depicting dose-related effects of inhibition of VEGF-induced phosphorylation of Akt at serine$^{473}$ (A) and threonine$^{308}$ (B) by methylnaltrexone.
Figure 3:
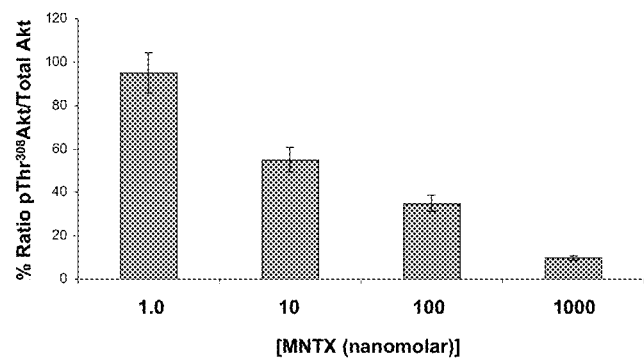

To assess the effects of methylnaltrexone (MNTX) on the VEGF-induced activation of the serine/threonine kinase Akt, a well-characterized endothelial cell line, human pulmonary microvascular endothelial cells (HPMVEC), was used. HPMVEC were serum starved for one hour and either untreated (control) or treated with VEGF (100 nM, 5 minutes) with or without pre-treatment (1 hour) with 100 nM MNTX, 100 ng/ml bevacizumab, 100 μM 5-FU, 100 nM MNTX+100 ng/ml bevacizumab or 100 nM MNTX+100 μM 5-FU. Cell lysates were obtained, run on SDS-PAGE and immunoblotted with anti-pSer$^{473}$Akt, anti-pThr$^{308}$Akt, anti-Akt or anti-actin antibody. The results indicated that methylnaltrexone abrogated VEGF-induced phosphorylation of Akt at the serine and threonine at positions 473 and 308, respectively (FIG. 2). Furthermore, methylnaltrexone in combination with bevacizumab and 5-FU synergistically inhibited Akt activation. The effects of various concentrations of MNTX (1.0, 10, 100, 1000 nM) on inhibition of VEGF-induced pSer$^{473}$Akt (FIG. 3A) and pThr$^{308}$Akt (FIG. 3B) immunoreactivity demonstrated that this inhibition is dose-dependent.

Cell Culture and Reagents—

Human pulmonary microvascular EC were obtained from Cambrex (Walkersville, Md.) and cultured as previously described (Singleton et al. (2006), Microvasc. Res. 72(1-2): 3-11; Singleton et al. (2007), Am. J. Respir. Cell Mol. Biol. 37(2):222-231) in EBM-2 complete medium (Cambrex) at 37° C. in a humidified atmosphere of 5% $CO_2$, 95% air, with passages 6-10 used for experimentation. Unless otherwise specified, reagents were obtained from Sigma (St. Louis, Mo.). Vascular endothelial growth factor (VEGF) was purchased from R&D Systems (Minneapolis, Minn.). Methylnaltrexone bromide (MNTX) was purchased from Mallinckrodt Specialty Chemicals (Phillipsburg, N.J.). Bevacizumab was purchased from Genentech (South San Francisco, Calif.). 5-fluorouracil (5-FU) was purchased from Abraxis Pharmaceutical Products (Schaumburg, Ill.). Naltrexone and rapamycin were purchased from Sigma (St. Louis, Mo.). Reagents for SDS-PAGE electrophoresis were purchased from Bio-Rad (Richmond, Calif.) and Immobilon-P transfer membrane was purchased from Millipore (Millipore Corp., Bedford, Mass.). Rabbit anti-pSer$^{473}$Akt, rabbit anti-pThr$^{308}$Akt and rabbit anti-Akt antibodies were purchased from Cell Signaling Technologies (Danvers, Mass.). Mouse anti-β-actin antibody was purchased from Sigma (St. Louis, Mo.). Secondary horseradish peroxidase (HRP)-labeled antibodies were purchased from Amersham Biosciences (Piscataway, N.J.).

SDS-PAGE and Immunoblotting—

Cellular materials from treated or untreated HPMVEC were incubated with IP buffer (50 mM HEPES (pH 7.5), 150 mM NaCl, 20 mM $MgCl_2$, 1% Nonidet P-40 (NP-40), 0.4 mM $Na_3VO_4$, 40 mM NaF, 50 μM okadaic acid, 0.2 mM phenylmethylsulfonyl fluoride, 1:250 dilution of Calbiochem protease inhibitor mixture 3), subjected to SDS-PAGE in 4-15% polyacrylamide gels, transferred onto Immobilon™ membranes, and developed with specific primary and secondary antibodies. Visualization of immunoreactive bands was achieved using enhanced chemiluminescence (Amersham Biosciences). In order to investigate the relative amount of activated Akt, the pSer$^{473}$Akt and pThr$^{308}$Akt immunoreactive band intensities were divided by total Akt immunoreactive band intensity.

Example 2

Figure 4:
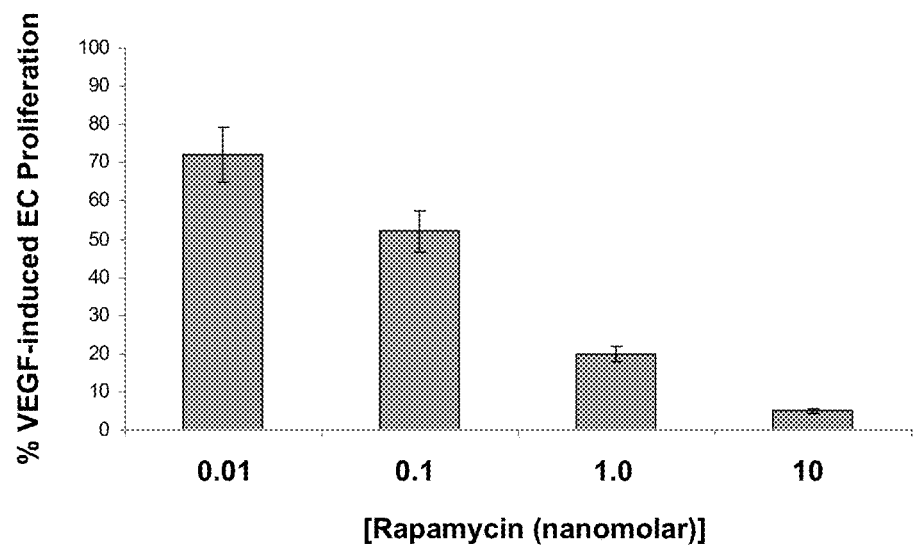
FIG. 4 is a graph depicting dose-related effects on inhibition of VEGF-induced endothelial cell proliferation by rapamycin.
Figure 5:
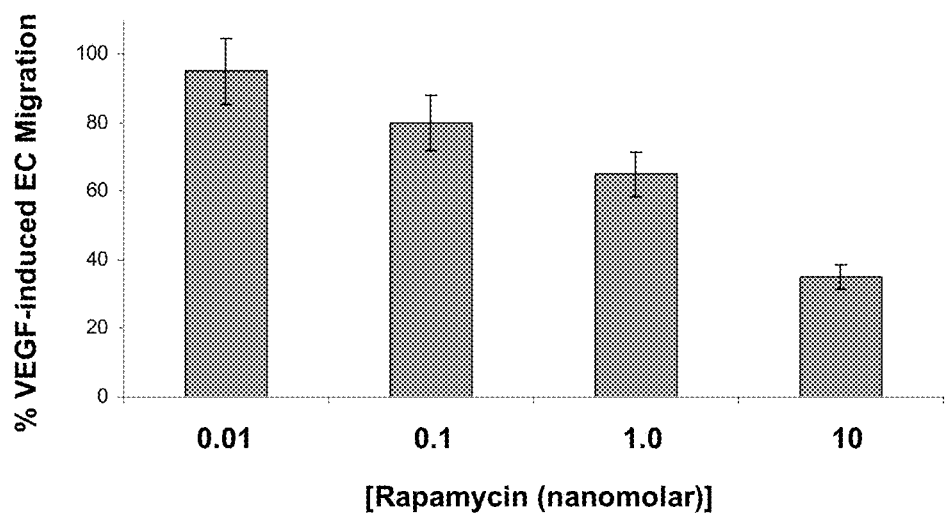
FIG. 5 is a graph depicting dose-related effects on inhibition of VEGF-induced endothelial cell migration by rapamycin.

Effect of Rapamycin on VEGF-Induced Endothelial Cell Migration and Proliferation To investigate the role of mTOR in cellular migration and proliferation, the effect of rapamycin on HPMVEC migration and proliferation assays was determined. Human EC were assayed for VEGF (100 nM)-induced profileration (FIG. 4) and migration (FIG. 5) in the presence or absence of 0.01, 0.1, 1.0 or 10 nM rapamycin. The results demonstrate that inhibition of mTOR by rapamycin results in a dose-dependent inhibition of endothelial cell proliferation and migration. This is in agreement with previous studies demonstrating that mTOR is involved in these processes.

Human Pulmonary Microvascular EC Migration Assay—

Twenty-four transwell units with 8 μM pore size were used for monitoring in vitro cell migration. HPMVEC (~1×10$^4$ cells/well) were plated with various treatments to the upper chamber and VEGF (100 nM) was added to the lower chamber. Cells were allowed to migrate for 18 hours. Cells from the upper and lower chamber were quantitated using the CellTiter96™ MTS assay (Promega, San Luis Obispo, Calif.) and read at 492 nm. Percent migration was defined as the # of cells in the lower chamber divided by the number of cells in both the upper and lower chamber. Each assay was set up in triplicate, repeated at least five times and analyzed statistically by Student's t test (with statistical significance set at P<0.05).

Human Pulmonary Microvascular EC Proliferation Assay—

For measuring cell growth, HPMVEC [5×10$^3$ cells/well] pretreated with various agents were incubated with 0.2 ml of serum-free media containing 100 nM VEGF for 24 h at 37° C. in 5% $CO_2$/95% air in 96-well culture plates. The in vitro cell proliferation assay was analyzed by measuring increases in cell number using the CellTiter96™ MTS assay (Promega, San Luis Obispo, Calif.) and read at 492 nm. Each assay was set up in triplicate, repeated at least five times and analyzed statistically by Student's t test (with statistical significance set at P<0.05).

Statistical Analysis—

Student's t test was used to compare the means of data from two or more different experimental groups. Results are expressed as means±S.E.

Example 3

Figure 6:
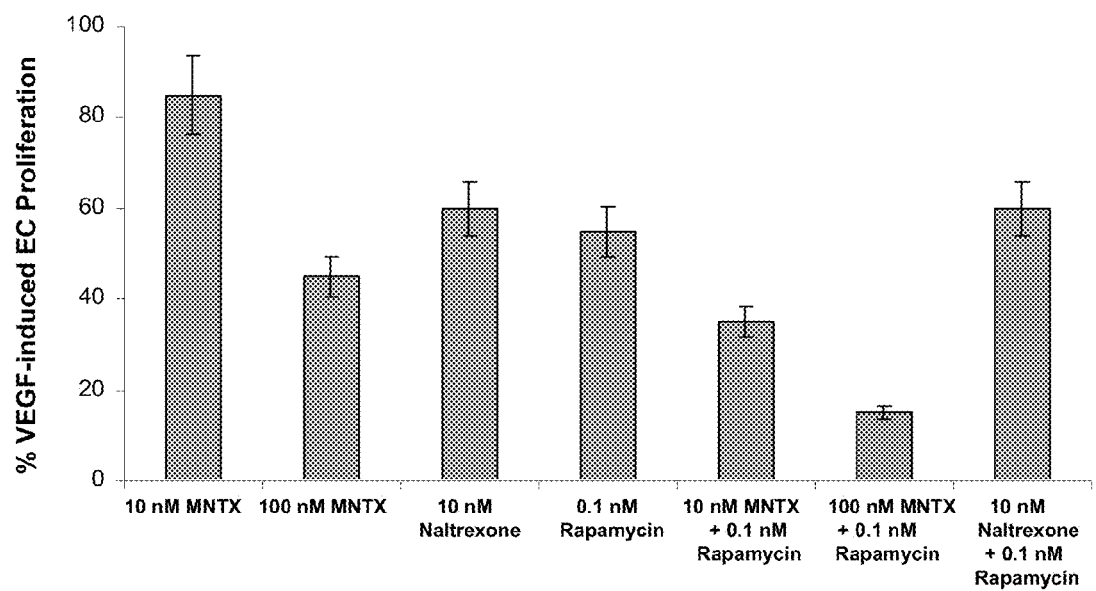
FIG. 6 is a graph depicting synergistic inhibition of VEGF-induced endothelial cell proliferation with a combination of methylnaltrexone and rapamycin.
Figure 7:
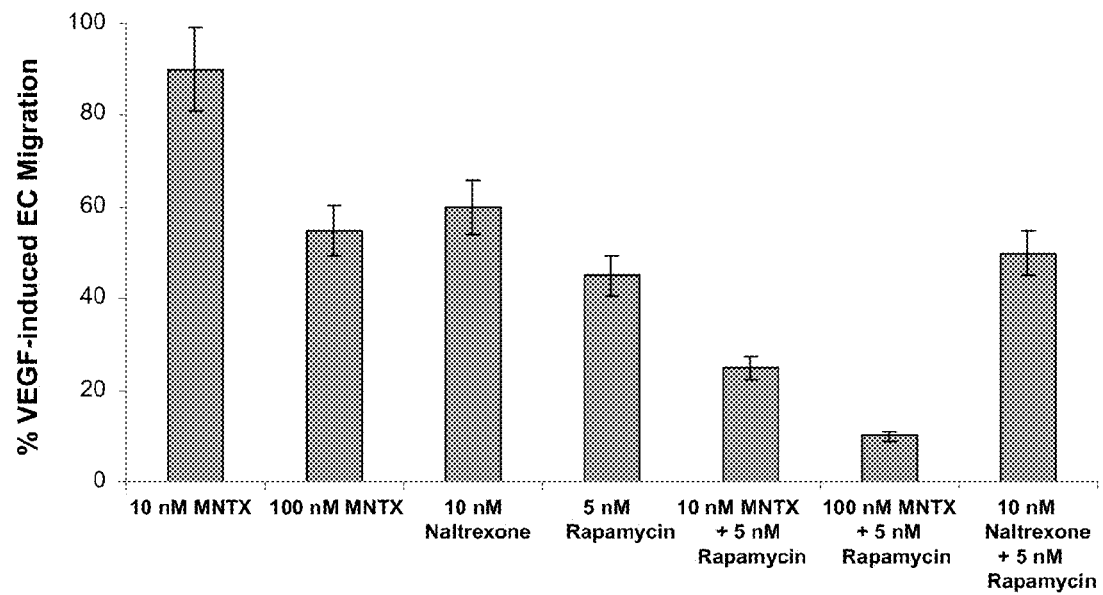
FIG. 7 is a graph depicting synergistic inhibition of VEGF-induced endothelial cell migration with a combination of methylnaltrexone and rapamycin.
Figure 10:
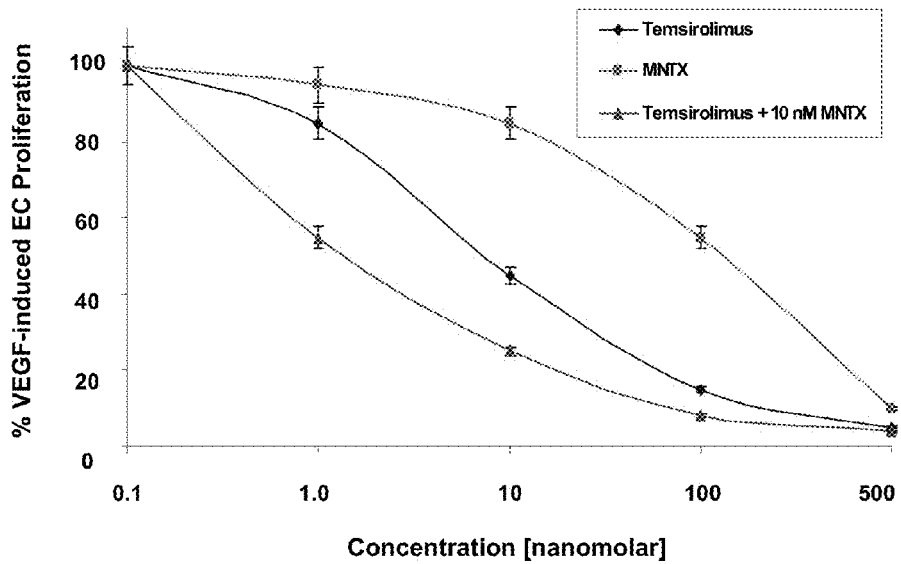
FIG. 10 provides graphs depicting (A) synergistic inhibition of VEGF-induced endothelial cell proliferation with a combination of methylnaltrexone and temsirolimus and (B) synergistic inhibition of VEGF-induced endothelial cell migration with a combination of methylnaltrexone and temsirolimus.
Figure 10:
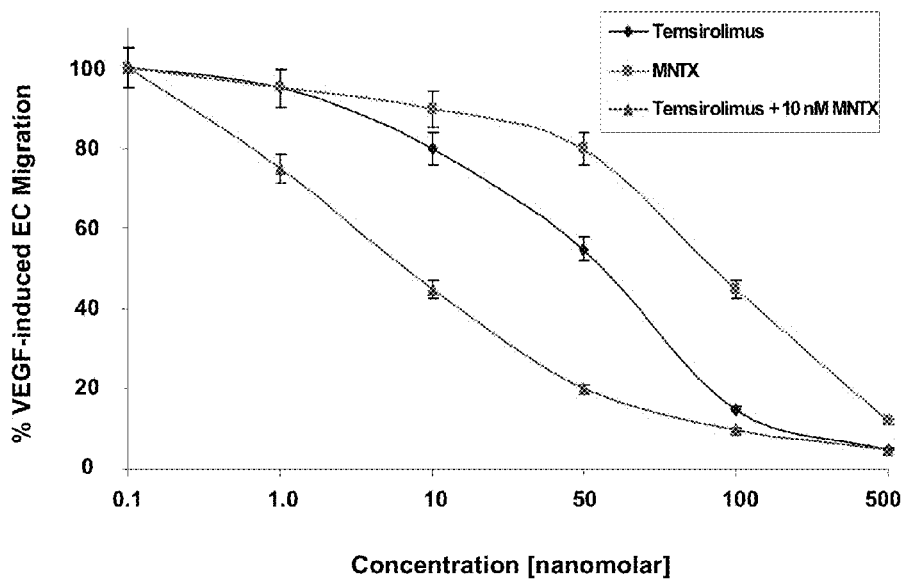

Synergistic Effect of Methylnaltrexone and mTOR Inhibitors on VEGF-Induced Endothelial Cell Migration and Proliferation Given the complex feedback inhibition signaling network that exists between Akt and mTOR, the migration and proliferation assays described above were used to determine whether the simultaneous inhibition of mTOR activation using rapamycin and inhibition of Akt using methylnaltrexone produced a synergistic effect on these processes. Human endothelial cells were assayed for VEGF (100 nM)-induced profileration (FIG. 6) and migration (FIG. 7) in the presence or absence of 10 or 100 nM MNTX, 10 nM naltrexone, 0.1 nM rapamycin, 100 nM MNTX+0.1 nM rapamycin or 10 nM naltrexone+0.1 nM rapamycin. Similar results were obtained with methylnaltrexone in combination with temsirolimus (FIG. 10).

Figure 8:
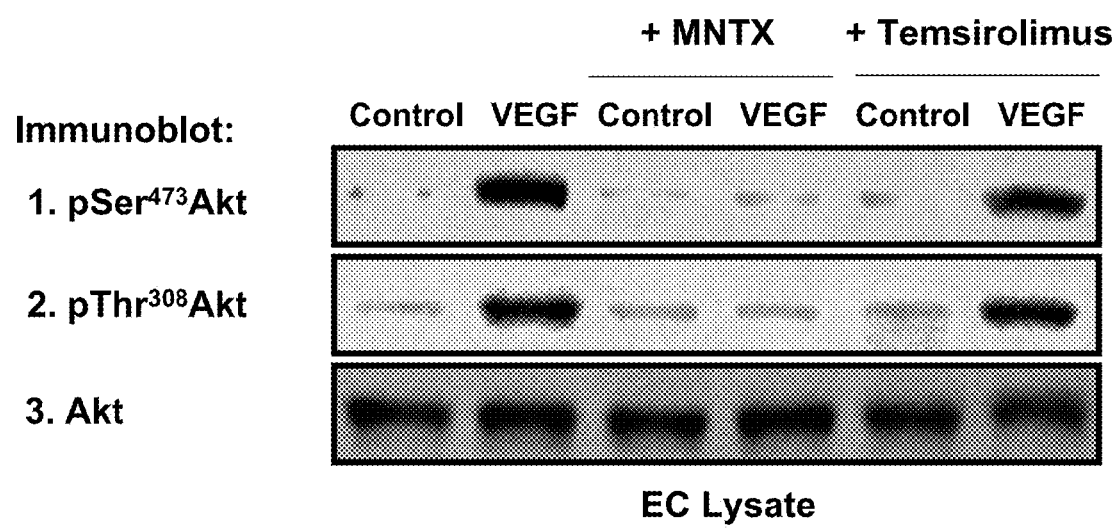
FIG. 8 is an immunoblot demonstrating the effect of methylnaltrexone and temsirolimus on VEGF-induced phosphorylation (activation) of Akt at serine$^{473}$ and threonine$^{308}$ using anti-phospho-serine$^{473}$-Akt, anti-phospho-threonine$^{308}$-Akt and anti-Akt specific antibodies in human endothelial cells.
Figure 9:
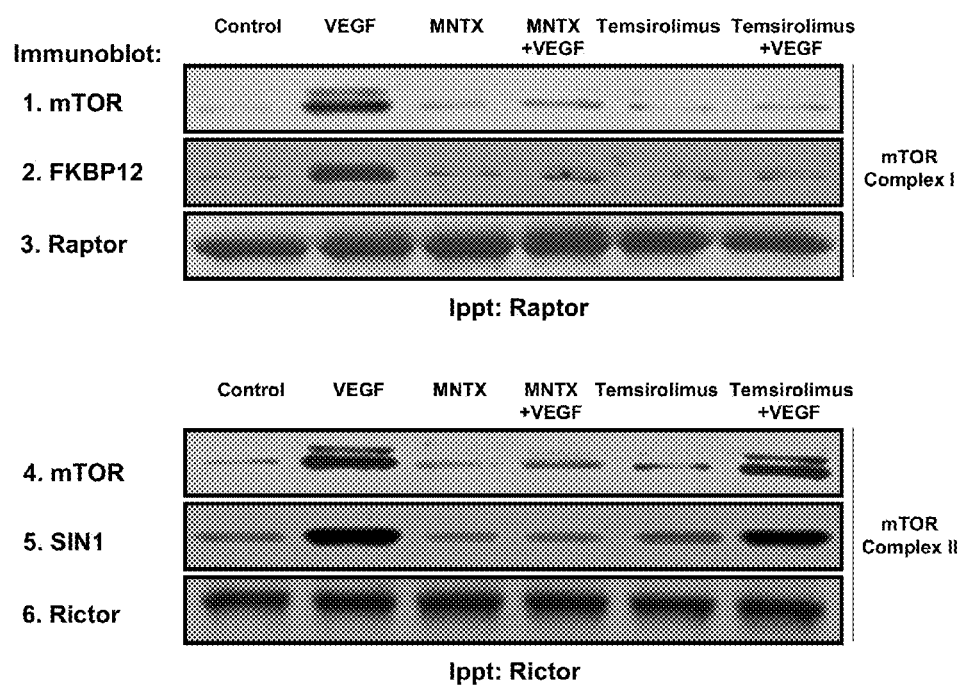
FIG. 9 shows immunoblots demonstrating (A) the effect of methylnaltrexone and temsirolimus on the VEGF-induced formation of mTOR Complex 1 and mTOR Complex 2 and (B) the effect of PI3 kinase inhibition, Src depletion and Rictor depletion on VEGF-induced phosphorylation (activation) of Akt at serine$^{473}$ and threonine$^{308}$ using anti-phospho-serine$^{473}$-Akt, anti-phospho-threonine$^{308}$-Akt and anti-Akt specific antibodies in human endothelial cells.
Figure 9:
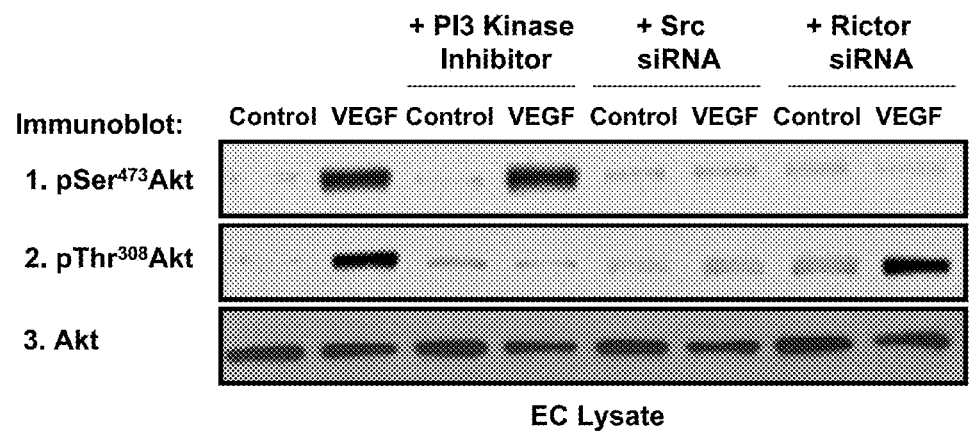
Figure 12:
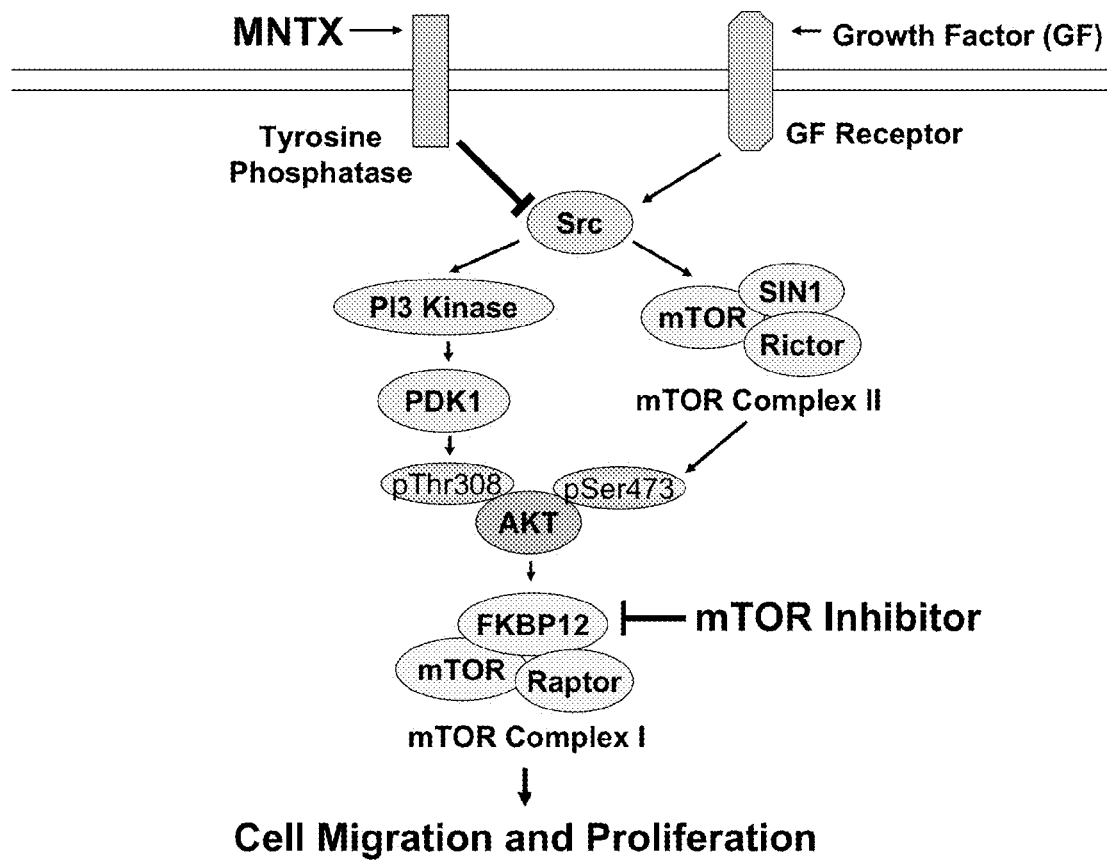
FIG. 12 is a schematic representation of a molecular basis of the synergistic activity of methylnaltrexone and mTOR inhibitors.

The results demonstrate that methylnaltrexone and mTOR inhibitors synergistically inhibit the migration and proliferation of endothelial cells. Unlike the results observed for methylnaltrexone, treatment of human endothelial cells with temsirolimus did not inhibit VEGF-induced activation of Akt (FIG. 8). This indicates that the observed synergistic effect of methylnaltrexone in combination with mTOR inhibitors is likely due to inhibition of the mTOR signaling pathway at two distinct points, with methylnaltrexone-induced inhibition occurring upstream of Akt activation and inhibition by mTOR inhibitors occurring downstream of Akt activation (FIG. 12). This hypothesis is bolstered by the fact that methylnaltrexone inhibits VEGF-induced formation of mTOR Complex I and mTOR Complex II, while temsirolimus inhibits the formation of mTOR complex II only (FIG. 9A).

Figure 11:
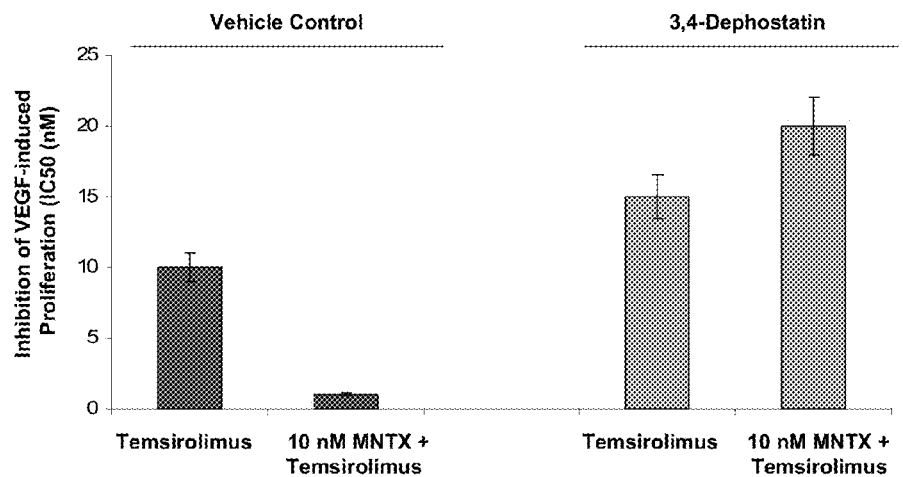
FIG. 11 provides graphs demonstrating that the synergistic inhibition of endothelial cell (A) proliferation and (B) migration with a combination of methylnaltrexone and temsirolimus is regulated by tyrosine phosphatase activity.
Figure 11:
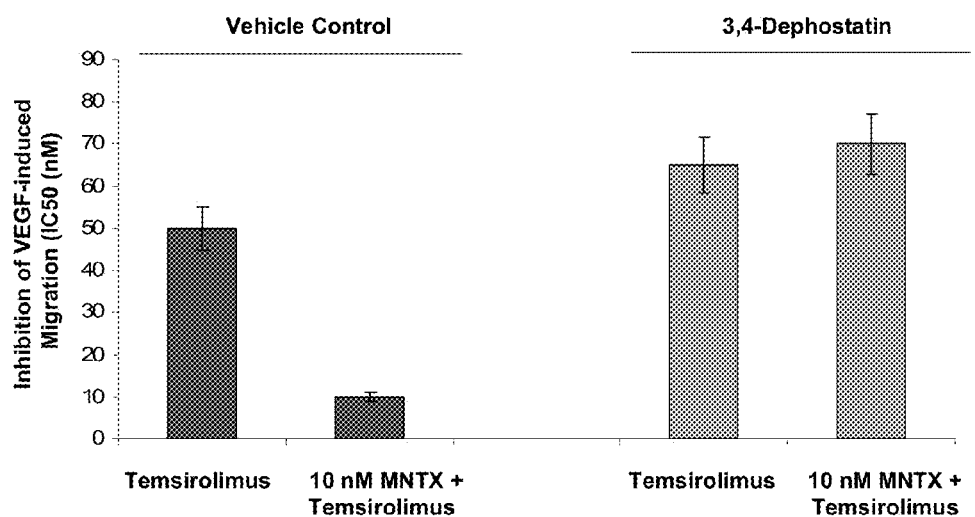

To further elucidate the mechanism of VEGF-induced Akt activation, human endothelial cells treated with VEGF with or without pretreatment with the PI3 kinase inhibitor, LY294002, Src siRNA or Rictor (mTOR complex II component) siRNA. Lysates were immunoblotted with anti-pSer$^{473}$Akt, anti-pThr$^{308}$Akt or anti-Akt antibody (FIG. 9B). PI3 kinase inhibitor inhibits VEGF-induced Akt threonine 308 phosphorylation. Inhibiting mTOR Complex 2 formation (Rictor siRNA) blocks VEGF-induced Akt serine 473 phosphorylation. Inhibiting Src expression (siRNA) blocks both Akt serine 473 and Akt threonine 308 phosphorylation. Further, the central role of tyrosine phosphatase (PTP) in the synergistic effect of methylnaltrexone in combination with mTOR inhibitors on human endothelial cell proliferation and migration was demonstrated using the potent PTP inhibitor 3,4-dephostatin, which inhibited these VEGF-induced pro-angiogenic events (FIG. 11).

MNTX and Temsirolimus Regulation of Akt Phosphorylation—

Human EC were serum starved for one hour and either untreated (control) or treated with VEGF (100 nM, 5 minutes) with or without pretreatment (1 hour) with 100 nM MNTX or 100 nM temsirolimus. EC lysates were obtained, run on SDS-PAGE and immunoblotted with anti-pSer$^{473}$Akt, anti-pThr$^{308}$Akt or anti-Akt antibody.

Analysis of mTOR Complex Formation and Regulation of Akt Phosphorylation—

Human EC were serum starved for one hour and either untreated (control) or treated with VEGF (100 nM, 5 minutes) with or without pretreatment (1 hour) with 100 nM MNTX or 100 nM Temsirolimus. EC lysates were obtained and immunoprecipitated with anti-Raptor (mTOR Complex 1 component) or anti-Rictor (mTOR complex 2 component) antibody. The immunoprecipitated material was run on SDS-PAGE and immunoblotted with either anti-mTOR, anti-FKBP12, anti-Raptor, anti-SIN1 or anti-Rictor antibody. To investigate the regulation of Akt phosphorylation, human EC were serum starved for one hour and either untreated (control) or treated with VEGF (100 nM, 5 minutes) with or without pretreatment with the PI3 kinase inhibitor, LY294002 (10 µM, 1 hour), Src siRNA or Rictor (mTOR complex 2 component) siRNA. EC lysates were obtained, run on SDS-PAGE and immunoblotted with anti-pSer$^{473}$Akt, anti-pThr$^{308}$Akt or anti-Akt antibody.

Synergistic Effects of MNTX with Temsirolimus on Inhibition of VEGF-Induced Human EC Proliferation and Migration.

Inhibition curves of human EC assayed for VEGF (100 nM)-induced proliferation and migration (24 hours) in the presence or absence of 0.1, 1.0, 10, 100 or 500 nM MNTX, Temsirolimus or 10 nM MNTX+Temsirolimus. MNTX inhibited EC VEGF-induced proliferation with an IC50 of ~100 nM. Adding 10 nM MNTX to EC shifted the IC50 of Temsirolimus inhibition of VEGF-induced proliferation from ~10 nM to ~1 nM. Experiments were performed in triplicate. Error bars=standard deviation.

MNTX Synergy with Temsirolimus is Regulated by Tyrosine Phosphatase Activity.

Human EC were assayed for VEGF (100 nM)-induced proliferation and migration (24 hours) in the presence of 10 nM or 15 nM Temsirolimus (IC50 concentrations for inhibition of proliferation in the absence or presence of 3,4-Dephostatin, respectively) with or without 10 nM MNTX. Experiments were performed in triplicate. Error bars=standard deviation.

While not wishing to be limited by any particular theory, FIG. 12 depicts a possible mechanism for the synergy demonstrated by the results of the Examples.

Example 4

Treatment of Mammalian Subjects with mTOR Inhibitors in Combination with Methylnaltrexone In a first set of experiments, mice are induced to develop tumors by transformation, inbreeding or transplantation of tumor cells. Forty-eight mice, each bearing tumors having a volume of at least 60 mm³, are randomly divided into four groups. The first group receives a control substance comprising neither an opioid antagonist nor an mTOR inhibitor. The second group receives the peripheral opioid antagonist methylnaltrexone administered via an acceptable route to contact the tumor with a therapeutically effective amount of methylnaltrexone, e.g., oral administration at a dose of 5 mg/kg/day. The third group receives the mTOR inhibitor, such as rapamycin, administered via an acceptable route to contact the tumor with a therapeutically effective amount of mTOR inhibitor, e.g., injection of rapamycin at a dose of 1 mg/kg/day. The forth group receives a combination of methylnaltrexone and mTOR inhibitor.

Differences in the rate of tumor growth, tumor size, angiogenesis within the tumor and mortality between each group of mice are recorded. Additional experiments will be performed using varied treatment doses of mTOR inhibitors, such as rapamycin, to determine the reduction in therapeutic dose of the mTOR inhibitor resulting from co-administration with methylnaltrexone.

Example 5

Treatment of Mammalian Subjects with mTOR Inhibitors in Combination with Alvimopan In a first set of experiments, mice are induced to develop tumors by transformation, inbreeding or transplantation of tumor cells. Forty-eight mice, each bearing tumors having a volume of at least 60 mm³, are randomly divided into four groups. The first group receives a control substance comprising neither an opioid antagonist nor an mTOR inhibitor. The second group receives the peripheral opioid antagonist alvimopan administered via an acceptable route to contact the tumor with a therapeutically effective amount of alvimopan. The third group receives the mTOR inhibitor, such as rapamycin, administered via an acceptable route to contact the tumor with a therapeutically effective amount of mTOR inhibitor, e.g., injection at a dose of 1 mg/kg/day. The forth group receives a combination of alvimopan and mTOR inhibitor.

Differences in the rate of tumor growth, tumor size, angiogenesis within the tumor and mortality between each group of mice are recorded. Additional experiments will be performed using varied treatment doses of mTOR inhibitors, such as rapamycin, to determine the reduction in therapeutic dose of the mTOR inhibitor resulting from co-administration with alvimopan.

In summary, methods in accordance with embodiments of the invention are provided for treating a disease or disorder associated with proliferation and migration of cells, including cancer and other hyperproliferative diseases as well as autoimmune disease, which methods include co-administration of an mTOR inhibitor and a μ-opioid receptor antagonist.

The invention has now been described with reference to various specific embodiments and techniques. However, it should be understood that many variations and modifications may be made while remaining within the spirit and scope of the invention.

All publications, patents, and patent applications are herein expressly incorporated by reference to the same extent as if each individual publication, patent, or patent application was specifically and individually indicated by reference. In case of conflict between the present disclosure and the incorporated patents, publications and references, the present disclosure should control.

The invention claimed is:

1. A pharmaceutical combination comprising an mTOR inhibitor and a peripheral mu-opioid receptor antagonist in a pharmaceutically acceptable dosage form and in synergistically effective amounts to inhibit unwanted migration and/or proliferation of cells in a subject in need thereof with the proviso that the mTOR inhibitor is not FK506 and wherein the peripheral mu-opioid receptor antagonist is a compound of formula (II):

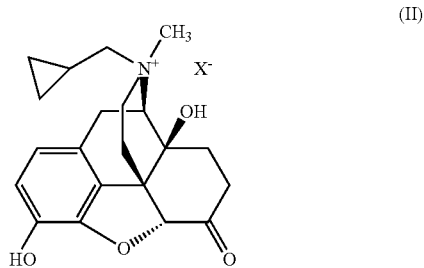

(II)

a single enantiomer, a mixture of enantiomers, a single diastereomer or a mixture of diastereomers thereof, or a pharmaceutically acceptable salt, solvate or prodrug thereof, wherein and X⁻ is chloride, bromide, iodide, carbonate or methylsulfate anion; and wherein the mTOR inhibitor is selected from the group consisting of TOP216, OSI-027, or a rapamycin derivative which is temsirolimus, everolimus, deforolimus, TAFA93, AP23573, ABT-578, or nab-rapamycin.

2. The combination of claim 1, wherein the unwanted migration and/or proliferation of cells is agonist-induced.

3. The combination of claim 1, wherein the mTOR inhibitor is temsirolimus.

4. The combination of claim 3, wherein the peripheral mu-opioid antagonist is methylnaltrexone.

5. The combination of claim 4 wherein, at the cells having unwanted proliferation and migration, the synergistically effective amount of temsirolimus is a concentration of ranging from 0.1 nM to 100 nM and a concentration of methylnaltrexone ranging from 0.1 to 100 nM.

* * * * *